US010081635B2

(12) United States Patent
Kim et al.

(10) Patent No.: US 10,081,635 B2
(45) Date of Patent: Sep. 25, 2018

(54) SUBSTITUTED N-(PYRROLIDINE-3-YL)-7H-PYRROLO[2,3-D]PYRIMIDINE-4-AMINE AS JANUS KINASE INHIBITOR

(71) Applicants: YANG JI CHEMICAL CO., LTD., Suwon-si, Gyeonggi-do (KR); HAN WHA PHARMA CO., LTD., Chuncheon-si, Gangwon-do (KR)

(72) Inventors: Jong Hoon Kim, Anyang-si (KR); Chie Yeon Chough, Suwon-si (KR); Hyun Uk Jeong, Suwon-si (KR); Sun Min Lee, Ansan-si (KR); Mi Suk Joung, Suwon-si (KR); Sung Jun Kim, Yongin-si (KR); Tae Wook Kim, Seoul (KR); Sung Il Lee, Yongin-si (KR); Eun Jung Yi, Yongin-si (KR); Kyeoung Ah Kim, Anseong-si (KR); Jae Min Lee, Gunpo-si (KR); Se Mi Yu, Suwon-si (KR); Young Soo Jo, Seoul (KR); Hong Sik Moon, Suwon-si (KR); Kyoung Rak Kim, Seoul (KR)

(73) Assignees: YANG JI CHEMICAL CO., LTD., Suwon-si, Gyeonggi-Do (KR); HAN WHA PHARMA CO., LTD., Gangwon-Do (KR)

( * ) Notice: Subject to any disclaimer, the term of this patent is extended or adjusted under 35 U.S.C. 154(b) by 0 days.

(21) Appl. No.: 15/507,409

(22) PCT Filed: Aug. 25, 2015

(86) PCT No.: PCT/KR2015/008880
§ 371 (c)(1),
(2) Date: Feb. 28, 2017

(87) PCT Pub. No.: WO2016/032209
PCT Pub. Date: Mar. 3, 2016

(65) Prior Publication Data
US 2017/0283421 A1    Oct. 5, 2017

(30) Foreign Application Priority Data

Aug. 29, 2014 (KR) .......................... 10-2014-0114516

(51) Int. Cl.
| | |
|---|---|
| *C07D 487/04* | (2006.01) |
| *A61K 31/519* | (2006.01) |
| *A61P 17/06* | (2006.01) |
| *A61P 35/00* | (2006.01) |
| *A61P 19/02* | (2006.01) |
| *A61P 3/10* | (2006.01) |
| *A61P 37/06* | (2006.01) |
| *A61P 17/00* | (2006.01) |
| *A61P 31/12* | (2006.01) |

(52) U.S. Cl.
CPC .......... *C07D 487/04* (2013.01); *A61K 31/519* (2013.01); *A61P 3/10* (2018.01); *A61P 17/00* (2018.01); *A61P 17/06* (2018.01); *A61P 19/02* (2018.01); *A61P 31/12* (2018.01); *A61P 35/00* (2018.01); *A61P 37/06* (2018.01)

(58) Field of Classification Search
CPC ........................... C07D 487/04; A61K 31/519
See application file for complete search history.

(56) References Cited

U.S. PATENT DOCUMENTS

2014/0336207 A1    11/2014  Zhang et al.

FOREIGN PATENT DOCUMENTS

| WO | WO 01/42246 A2 | 6/2001 |
|---|---|---|
| WO | WO 2005/124342 A2 | 12/2005 |
| WO | WO 2007/012953 A2 | 2/2007 |
| WO | WO 2010/014930 A2 | 2/2010 |
| WO | WO 2012/058645 A1 | 5/2012 |
| WO | WO 2012/125893 A1 | 9/2012 |
| WO | WO 2013/091539 A1 | 6/2013 |
| WO | WO 2014/075393 A1 | 5/2014 |
| WO | WO 2014/101295 A2 | 7/2014 |

OTHER PUBLICATIONS

Flanagan et al.; "Discovery of CP-690,550: A Potent and Selective Janus Kinase (JAK) Inhibitor for the Treatment of Autoimmune Diseases and Organ Transplant Rejection", *J. Med. Chem.* 53, pp. 8468-8484 (Nov. 24, 2010).
Cheng et al.; "Relationship Between the Inhibition Constant ($K_I$) and the Concentration of Inhibitor Which Causes 50 Per Cent Inhibition ($I_{50}$) of an Enzymatic Reaction", *Biochemical Pharmacology*, vol. 22, pp. 3099-3108, Pergamon Press, Great Britain (1973).
Brand et al.; "Collagen-induced arthritis", *Nature Protocols*, vol. No. 5, pp. 1269-1275, (May 17, 2007).
Korean Patent Office, Search Report in International Patent Application No. PCT/KR2015/008880 (dated Jul. 12, 2016).
Benveniste E. et al., "Involvement of the Janus Kinase/Signal Transducer and Activator of Transcription Signaling Pathway in Multiple Sclerosis and the Animal Model of Experimental Autoimmune Encephalomyeliti", *Journal of Interferon & Cytokine Research*, vol. 34, No. 8, 577-588 (2014).
Cetkovic-Cvrlje M. et al. "Targeting Janus tyrosine kinase 3 (JAK3) with an inhibitor induces secretion of TGF-β by CD4+T cells", *Cellular & Molecular Immunology*, 9, 350-360 (2012).
Chiricozzi A. et al., "New topical treatments for psoriasis", *Expert Opinion on Pharmacotherapy*, 15:4, 461-470, DOI: 10.1517/14656566.2014.875159 (2014).

(Continued)

*Primary Examiner* — Susanna Moore
(74) *Attorney, Agent, or Firm* — Leydig, Voit & Mayer

(57) ABSTRACT

A novel substituted N-(pyrrolidin-3-yl)-7H-pyrrolo[2,3-d]pyrimidin-4-amine and a use thereof as a Janus kinase (JAK) inhibitor are provided.

10 Claims, 1 Drawing Sheet
Specification includes a Sequence Listing.

(56) References Cited

OTHER PUBLICATIONS

Hsu L. et al., "JAK Inhibitors: Treatment Efficacy and Safety Profile in Patients with Psoriasis", *Journal of Immunology Research*, vol. 2014, Article ID 283617, 7 pages, http://dx.doi.org/10.1155/2014/283617 (2014).

Kawasaki M. et al., "Possible role of the JAK/STAT pathways in the regulation of T cell-interferon related genes in systemic lupus erythematosus", *Lupus*, 20, 1231-1239 (2011).

Liu Y. et al., "Therapeutic Efficacy of Suppressing the JAK/STAT Pathway in Multiple Models of Experimental Autoimmune Encephalomyelitis", *J. Immunol.*, 192:59-72, doi: 10.4049/jimmunol.1301513 (2014).

Merciris D. et al., "P072 GLPG0634, the first selective JAK1 inhibitor, shows strong activity in the mouse DSS-colitis model", *J. Amer. Acad. Derma.*, vol. 8, Supplement 1, p. S92 (2014).

Neurath M., "New targets for mucosal healing and therapy in inflammatory bowel diseases", *Mucosal Immunology*, vol. 7, No. 1, 6-19 (2014).

Ortiz-Ibáñez K. et al., "Tofacitinib and Other Kinase Inhibitors in the Treatment of Psoriasis", *Actas Dermosifiliogr.*, 104(4):304-310 (2013).

O'Shea J. et al., "Janus kinase inhibitors in autoimmune diseases", *Ann. Rheum Dis.*; 72:ii111-ii115. doi:10.1136/annrheumdis-2012-202576 (2013).

Papp K. et al., "Efficacy and safety of tofacitinib, an oral Janus kinase inhibitor, in the treatment of psoriasis: a Phase 2b randomized placebo-controlled dose-ranging study", *British Joural of Dermatology*, 167, 668-677 (2012).

Patterson H. et al., "Protein kinase inhibitors in the treatment of inflammatory and autoimmune diseases", *Clinical and Experimental Immunology*, 176: 1-10, doi:10.1111/cei.12248 (2013).

Wang S. et al., "Jak/STAT signaling is involved in the inflammatory infiltration of the kidneys in MRL/lpr mice", *Lupus*, 19, 1171-1180 (2010).

Xiao L. et al., "Association of single-nucleotide polymorphisms in the STAT3 gene with autoimmune thyroid disease in Chinese individuals", *Funct. Integr. Genomics*, 13:455-461, DOI 10.1007/s10142-013-0337-0 (2013).

European Patent Office, Extended European Search Report in counterpart European Application No. 15835571.9, dated Mar. 19, 2018.

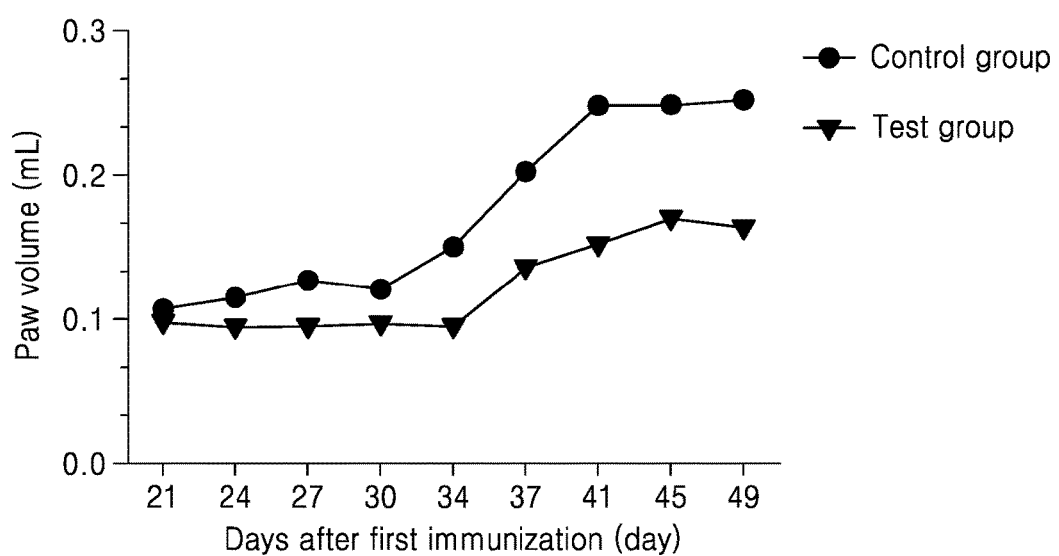

SUBSTITUTED N-(PYRROLIDINE-3-YL)-7H-PYRROLO[2,3-D]PYRIMIDINE-4-AMINE AS JANUS KINASE INHIBITOR

TECHNICAL FIELD

The present disclosure relates to substituted N-(pyrrolidin-3-yl)-7H-pyrrolo[2,3-d]pyrimidin-4-amine and its use as a Janus kinase (JAK) inhibitor.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,384 Byte ASCII (Text) file named "728012_Sequence.txt," created on Feb. 28, 2017.

BACKGROUND ART

Janus kinase (hereinafter, also referred to as "JAK") performs some of the various functions of tyrosine kinases on cytoplasmic protein. A series of various functions of the JAK are carried out through the action of signal transducers and activators of transcription ("STAT"), and are important as a trigger of the cellular signalling system initiated by cytokines.

JAK is widely involved across the overall mechanism of cytokine expression initiation. Four JAK proteins (JAK1, JAK2, JAK3, and tyrosine kinase 2 (TYK2)) and 7 STAT molecules are known initiation factors. In particular, JAK family proteins play important roles in intrinsic and adaptive immune systems. It has been found that in the pathogenesis of rheumatoid arthritis, cytokine receptors containing the common gamma-chain are related to the expression of JAK1 and JAK3 proteins. It has also been found that the expression of a large number of cytokines and hormones are involved in the cytoplasmic signalling system. Pathologically, these facts suggest the likelihood of reduction in the expression of pathogenesis-related cytokines by inhibition of JAK1 and JAK3. Accordingly, compounds that may inhibit JAK proteins such as JAK1 and JAK3 may be useful in the treatment of multiple allergic diseases, inflammation and autoimmune diseases, including rheumatoid arthritis, lupus erythematosus, pauciarticular juvenile rheumatoid arthritis, arthritis, asthma, chronic obstructive pulmonary disease (COPD), tissue fibrosis (for example, myelofibrosis), eosinophilic leukocytosis inflammation, esophagitis, inflammatory bowel disease, organ transplant rejection, graft-versus-host disease, psoriasis, myositis, and multiple sclerosis.

Rheumatoid arthritis is a progressive autoimmune disease that causes intraarticular inflammation, pain, and injury. Inflammatory precursor cytokines (for example, tumor necrosis factors) are secreted by the action of T lymphocytes and B lymphocytes, and JAK (JAK1 and JAK3) relays the action of STAT from the inflammatory precursor cytokines and induces secretion of intracellular cytokines, causing joint inflammation and injury. Of a number of cytokines, IL-1, IL-6, and IL-16 are related to the growth of cells which mediate immune inflammatory responses, and also are likely closely related to the onset of rheumatoid arthritis. Many studies conducted on humans and animals have also revealed that gene expression through the JAK-STAT mechanism plays a significant role in inflammatory response control.

Vandeghinste et al. (WO 2005/124342) discovered that inhibition of JAK1 is a target mechanism useful for the treatment of various diseases, including osteoarthritis. According to an experimental result, JAK1-knockout mice died within 24 hours after birth due to immaturity of lymphocytes, since JAK1 plays an absolutely essential role in the development and maturation of lymphocytes. In JAK1-negative cells, due to non-functioning of type II cytokine receptors, the gamma-c subunit did not function, and consequently, related cytokine receptors, i.e., receptors using the gp130 subunit, did not function.

Among JAK family proteins, JAK2 is particularly related to myeloproliferative disorders. That is, inhibition of JAK2 may likely be helpful in the treatment of myeloproliferative disorders. JAK1, JAK2, and JAK3 proteins are all related to cancer, and were found to be useful for the treatment of tumors, and in particular, myelogenous leukemia (for example, acute myelogenous leukemia (AML)), and lymphoblastic leukemia (for example, acute lymphoblastic leukemia (ALL)).

In rheumatoid arthritis, from the understanding that inflammatory arthritis symptoms may be relieved by inhibiting the expression of STAT1, STAT3, STAT4, and STAT6 in the JAK-STAT signal transduction pathway, inhibition of the JAK-STAT signalling pathway by inhibiting the generation of inflammatory cytokines (for example, TNF-α, IL-1, and IL-6) which may increase manifestation of symptoms was found to be ideal. Targeting multiple signal transduction pathways is effective to inhibit pathological disease symptoms of rheumatoid arthritis.

A perfect therapy for rheumatoid arthritis has not yet been developed, and studies on related mechanisms are ongoing. In the pathogenesis of rheumatoid arthritis, multiple factors related to other immune and inflammatory diseases are involved. For this reason, if a drug for rheumatoid arthritis is developed, the drug may more likely be applicable in other immune and inflammatory diseases (for example, proliferative disease, graft-versus-transplant rejection, cartilage proliferative disorder, dysplasia, and IL-6 and interferon hypersecretion-related diseases). Therefore, through the present invention, it is possible to synthesize, produce, and formulate a material applicable to such diseases and symptoms as described above, and thus develop mass-producible medicines.

DETAILED DESCRIPTION OF THE INVENTION

Technical Problem

The present invention provides a compound of Formula 1, or a pharmaceutically acceptable salt, solvate, or stereoisomer thereof.

The present invention provides a pharmaceutical composition that includes the compound of Formula 1, or a pharmaceutically acceptable salt, solvate, or stereoisomer thereof, and a pharmaceutically acceptable carrier.

The present invention provides a method of regulating the activity of a Janus kinase (JAK) by using the compound of Formula 1, or a pharmaceutically acceptable salt, solvate, or stereoisomer thereof.

The present invention provides a method of treating a disease in a subject by administering a therapeutically effective amount of the compound of Formula 1, or a pharmaceutically acceptable salt, solvate, or stereoisomer thereof, to a subject.

The present invention provides a method of preparing the compound of Formula 1.

Technical Solution

In an aspect of the present disclosure, a compound of Formula 1, or a pharmaceutically acceptable salt, solvate, or stereoisomer thereof, is provided.

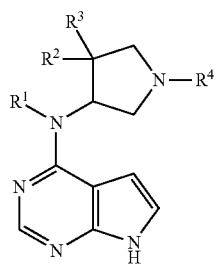

(Formula 1)

In Formula 1, $R^1$ may be $C_{1-6}$ alkyl, $C_{2-6}$ alkenyl, or $C_{2-6}$ alkynyl, $R^2$ and $R^3$ taken together form —($C_{2-6}$ alkyl)- or —($C_{2-6}$ alkenyl)-, $R^4$ may be —$W^1$—$R^6$;

$W^1$ may be absent, or may be —C(=O)—, —C(=S)—, —C(=O)O—, —C(=O)NR$^5$—, —C(=S)NR$^5$—, —S(=O)—, or —S(=O)$_2$—;

$R^5$ may be H or $C_{1-6}$ alkyl;

$R^6$ may be H; halo; CN; NO$_2$; N$_3$; $C_{1-10}$ alkyl; $C_{2-10}$ alkenyl; $C_{2-10}$ alkynyl; $C_{1-6}$ haloalkyl; $C_{5-20}$ aryl optionally substituted with at least one substituent selected from the group consisting of $C_{1-10}$ alkyl, $C_{1-6}$ haloalkyl, halo, CN, NO$_2$, and —O—($C_{1-10}$ alkyl); $C_{3-7}$ cycloalkyl; heterocycloalkyl having 3 to 7 ring atoms, optionally substituted with —C(C=O)($C_{1-6}$ alkyl); heteroaryl having 3 to 7 ring atoms; heteroaryl-($C_{1-10}$ alkyl) having 3 to 7 ring atoms; —($C_{1-10}$ alkyl)-CN; —($C_{1-10}$ alkyl)-N$_3$; —($C_{1-10}$ alkyl)-O—($C_{1-6}$ alkyl); —($C_{1-10}$ alkyl)-C(=O)NR$^a$R$^b$; or —($C_{1-10}$ alkyl)-NR$^a$C(=O)R$^b$ or —($C_{1-10}$ alkyl)-NR$^c$R$^d$, wherein R$^a$, R$^b$, R$^c$, and R$^d$ may each independently be H or $C_{1-6}$ alkyl.

In some embodiments, in Formula 1, $R^1$ may be a linear or branched $C_{1-6}$ alkyl, for example, a linear or branched $C_{1-3}$ alkyl. The $C_{1-6}$ alkyl may be, for example, methyl, ethyl, propyl, isopropyl, butyl, isobutyl, tert-butyl, pentyl, neopentyl, or hexyl. In Formula 1, $R^1$ may also be a linear or branched $C_{2-6}$ alkenyl, for example, $C_{2-3}$ alkenyl. In Formula 1, $R^1$ may be a linear or branched $C_{2-6}$ alkynyl, for example, $C_{2-3}$ alkynyl.

In some embodiments, $R^2$ and $R^3$ taken together may form —($C_{2-6}$ linear or branched alkyl)-. For example, $R^2$ and $R^3$ taken together may form —(CH$_2$)$_n$—, where n may be 2 to 6. For example, $R^2$ and $R^3$ taken together may form —($C_{2-6}$ linear or branched alkenyl)-.

In some embodiments, $W^1$ may be absent, or may be —C(=O)—, —C(=S)—, —C(=O)O—, —C(=O)NR$^5$—, —C(=S)NR$^5$—, or —S(=O)$_2$—.

In some embodiments, $R^6$ may be $C_{1-10}$ alkyl (for example, $C_{1-6}$ alkyl); $C_{2-10}$ alkenyl (for example, $C_{2-6}$ alkenyl); $C_{2-10}$ alkynyl (for example, $C_{2-6}$ alkynyl); $C_{1-6}$ haloalkyl (for example, $C_{1-3}$ haloalkyl); $C_{5-20}$ aryl (for example, $C_{6-12}$ aryl) optionally substituted with at least one substituent selected from the group consisting of $C_{1-10}$ alkyl (for example, $C_{1-6}$ alkyl), $C_{1-6}$ haloalkyl (for example, $C_{1-3}$ haloalkyl), halo, CN, NO$_2$, and —O—($C_{1-10}$ alkyl) (for example, —O—($C_{1-6}$ alkyl)); $C_{3-7}$ cycloalkyl; heterocycloalkyl (for example, piperidinyl) having 3 to 7 ring atoms, optionally substituted with —C(C=O)($C_{1-6}$ alkyl); heteroaryl (for example, furanyl, pyridinyl, or imidazolyl) having 3 to 7 ring atoms; heteroaryl (for example, furanyl, pyridinyl, or imidazolyl)-($C_{1-10}$ alkyl) having 3 to 7 ring atoms; —($C_{1-10}$ alkyl)-CN; —($C_{1-10}$ alkyl)-N$_3$; —($C_{1-10}$ alkyl)-O—($C_{1-6}$ alkyl); ($C_{1-10}$ alkyl)-C(=O)NR$^a$R$^b$; or —($C_{1-10}$ alkyl)-NR$^a$C(=O)R$^b$ or —($C_{1-10}$ alkyl)-NR$^c$R$^d$, wherein R$^a$, R$^b$, R$^c$, and R$^d$ may each independently be H or $C_{1-6}$ alkyl. For example, R$^6$ may be $C_{1-6}$ alkyl; $C_{2-6}$ alkenyl; $C_{2-6}$ alkynyl; $C_{1-3}$ haloalkyl (for example, $C_{1-3}$ trifluoroalkyl); $C_{6-12}$ aryl (for example, phenyl, naphthalenyl, or biphenyl) optionally substituted with at least one substituent selected from the group consisting of $C_{1-6}$ alkyl, $C_{1-3}$ haloalkyl (for example, $C_{1-3}$ trifluoroalkyl), halo, CN, NO$_2$, and —O—($C_{1-6}$ alkyl); $C_{3-7}$ cycloalkyl (for example, cyclopropyl, or cyclohexyl); heterocycloalkyl (for example, piperidinyl) having 3 to 7 ring atoms, optionally substituted with —C(C=O)($C_{1-6}$ alkyl); heteroaryl (for example, furanyl, pyridinyl, or imidazolyl) having 3 to 7 ring atoms; heteroaryl-($C_{1-6}$ alkyl) having 3 to 7 ring atoms (for example, furanyl-($C_{1-6}$ alkyl), pyridinyl-($C_{1-6}$ alkyl), or imidazolyl-($C_{1-6}$ alkyl)); —($C_{1-6}$ alkyl)-CN; —($C_{1-6}$ alkyl)-N$_3$; —($C_{1-6}$ alkyl)-O—($C_{1-3}$ alkyl); ($C_{1-6}$ alkyl)-C(=O)NR$^a$R$^b$; or —($C_{1-6}$ alkyl)-NR$^a$C(=O)R$^b$ or —($C_{1-6}$ alkyl)-NR$^c$R$^d$, wherein R$^a$, R$^b$, R$^c$, and R$^d$ may each independently be H or $C_{1-3}$ alkyl.

In some embodiments, in the compound of Formula 1, or a pharmaceutically acceptable salt, solvate, or stereoisomer thereof, $R^1$ in Formula 1 may be $C_{1-6}$ alkyl, $R^2$ and $R^3$ taken together may form —($C_{2-6}$ alkyl)-, $R^4$ may be —$W^1$—$R^6$, $W^1$ may be absent, or may be —C(=O)—, —C(=S)—, —C(=O)O—, —C(=O)NR$^5$—, —C(=S)NR$^5$—, or —S(=O)$_2$—, $R^5$ may be H or $C_{1-6}$ alkyl, and $R^6$ may be $C_{1-10}$ alkyl; $C_{1-6}$ haloalkyl; $C_{5-20}$ aryl optionally substituted with at least one substituent selected from the group consisting of $C_{1-10}$ alkyl, $C_{1-6}$ haloalkyl, halo, CN, NO$_2$, and —O—($C_{1-10}$ alkyl); $C_{3-7}$ cycloalkyl; heterocycloalkyl having 3 to 7 ring atoms, optionally substituted with —C(C=O)($C_{1-6}$ alkyl); heteroaryl having 3 to 7 ring atoms; heteroaryl-($C_{1-10}$ alkyl) having 3 to 7 ring atoms; —($C_{1-10}$ alkyl)-CN; —($C_{1-10}$alkyl)-N$_3$; ($C_{1-10}$alkyl)-O—($C_{1-6}$ alkyl); ($C_{1-10}$ alkyl)-C(=O)NR$^a$R$^b$; —($C_{1-10}$ alkyl)-NR$^a$C(=O)R$^b$; or —($C_{1-10}$ alkyl)-NR$^c$R$^d$, wherein R$^a$, R$^b$, R$^c$, and R$^d$ may each independently be H or $C_{1-6}$ alkyl.

In some other embodiments, in the compound of Formula 1, or a pharmaceutically acceptable salt, solvate, or stereoisomer thereof, $R^1$ in Formula 1 may be a methyl, $R^2$ and $R^3$ taken together may form —CH$_2$CH$_2$—, $R^4$ may be —$W^1$—$R^6$, $W^1$ may be absent, or may be —C(=O)—, —C(=S)—, —C(=O)O—, —C(=O)NR$^5$—, —C(=S)NR$^5$—, or —S(=O)$_2$—, $R^5$ may be H or $C_{1-6}$ alkyl, and $R^6$ may be $C_{1-10}$ alkyl; $C_{1-6}$ haloalkyl; $C_{5-20}$ aryl optionally substituted with at least one selected from the group consisting of $C_{1-10}$ alkyl, $C_{1-6}$ haloalkyl, halo, CN, NO$_2$, and —O—($C_{1-10}$ alkyl); $C_{3-7}$ cycloalkyl; heterocycloalkyl having 3 to 7 ring atoms, optionally substituted with —C(C=O) ($C_{1-6}$ alkyl); heteroaryl having 3 to 7 ring atoms; heteroaryl-($C_{1-10}$ alkyl) having 3 to 7 ring atoms; —($C_{1-10}$ alkyl)-CN; —($C_{1-10}$ alkyl)-N$_3$; —($C_{1-10}$ alkyl)-O—($C_{1-6}$ alkyl); ($C_{1-10}$ alkyl)-C(=O)NR$^a$R$^b$; —(C$_{1-10}$ alkyl)-NR$^a$C(=O)R$^b$; or —(C$_{1-10}$ alkyl)-NR$^c$R$^d$, wherein R$^a$, R$^b$, R$^c$, and R$^d$ may each independently be H or C$_{1-6}$ alkyl.

In some other embodiments, in the compound of Formula 1, or a pharmaceutically acceptable salt, solvate, or stereoisomer thereof, R$^1$ in Formula 1 may be methyl, R$^2$ and R$^3$ taken together may form —CH$_2$CH$_2$—, R$^4$ may be —W$^1$—R$^6$, W$^1$ may be absent, or may be —C(=O)—, —C(=S)—, —C(=O)O—, —C(=O)NR$^5$—, —C(=S)NR$^5$—, or —S(=O)$_2$—, R$^5$ may be H or C$_{1-6}$ alkyl, R$^6$ may be C$_{1-10}$ alkyl; trifluoro-(C$_{1-3}$ alkyl); phenyl, naphthalenyl, or biphenyl, optionally substituted with at least one substituent selected from the group consisting of C$_{1-10}$ alkyl, trifluoro-(C$_{1-3}$ alkyl), halo, CN, NO$_2$, and —O—(C$_{1-10}$ alkyl); C$_{3-7}$ cycloalkyl; piperidinyl or morpholinyl, optionally substituted with —C(C=O)(C$_{1-6}$ alkyl); furanyl; pyridinyl; an imidazolyl-(C$_{1-10}$ alkyl); —(C$_{1-10}$ alkyl)-CN; —(C$_{1-10}$ alkyl)-N$_3$; —(C$_{1-10}$ alkyl)-O—(C$_{1-6}$ alkyl); (C$_{1-10}$ alkyl)-C(=O)NR$^a$R$^b$; —(C$_{1-10}$ alkyl)-NR$^a$C(=O)R$^b$; or —(C$_{1-10}$ alkyl)-NR$^c$R$^d$, wherein R$^a$, R$^b$, R$^c$, and R$^d$ may each independently be H or C$_{1-6}$ alkyl.

In some other embodiments, in the compound of Formula 1, or a pharmaceutically acceptable salt, solvate, or stereoisomer thereof, the compound of Formula 1 may be represented by Formula 2:

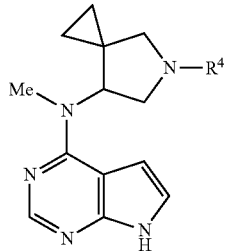

(Formula 2)

wherein, in Formula 2,

R$^4$ may be —W$^1$—R$^6$,

W$^1$ may be absent, or may be —C(=O)—, —C(=S)—, —C(=O)O—, —C(=O)NR$^5$—, —C(=S)NR$^5$—, or —S(=O)$_2$—, R$^5$ may be H or C$_{1-6}$ alkyl, and R$^6$ may be C$_{1-10}$ alkyl, when W$^1$ is absent;

C$_{1-10}$ alkyl; C$_{3-7}$ cycloalkyl; —(C$_{1-10}$ alkyl)-CN; —(C$_{1-10}$ alkyl)-N$_3$; —(C$_{1-10}$ alkyl)-NR$^a$C(=O)R$^b$, wherein R$^a$ and R$^b$ may each independently be H or C$_{1-6}$ alkyl; —(C$_{1-10}$ alkyl)-C(=O)NR$^a$R$^b$, wherein R$^a$ and R$^b$ may each independently be H or C$_{1-6}$ alkyl; phenyl; phenyl substituted with at least one substituent selected from the group consisting of —CF$_3$ and CN; piperidinyl substituted with —C(C=O)(C$_{1-6}$ alkyl); furanyl; pyridinyl; imidazolyl-(C$_{1-10}$ alkyl); —(C$_{1-10}$ alkyl)-O—(C$_{1-6}$ alkyl); or —(C$_{1-10}$ alkyl)-NR$^c$R$^d$, wherein R$^c$ and R$^d$ may each independently be H or C$_{1-6}$ alkyl, when W$^1$ is —C(=O)—;

—(C$_{1-10}$ alkyl)-CN, when W$^1$ is —C(=S)—;

—(C$_{1-10}$ alkyl), when W$^1$ is —C(=O)O—;

—(C$_{1-10}$ alkyl); C$_{3-7}$ cycloalkyl; phenyl; phenyl substituted with at least one substituent selected from the group consisting of halo and C$_{1-10}$ alkyl; biphenyl; or biphenyl substituted with at least one substituent selected from the group consisting of halo and C$_{1-10}$ alkyl, when W$^1$ is —C(=O)NR$^5$;

phenyl substituted with at least one —CF$_3$, when W$^1$ is —C(=S)NR$^5$; or

—(C$_{1-10}$ alkyl); —CF$_3$; piperidinyl; morpholinyl; —(C$_{1-10}$ alkyl)-NR$^c$R$^d$, wherein R$^c$ and R$^d$ may each independently be H or C$_{1-6}$ alkyl; phenyl; phenyl substituted with at least one substituent selected from —(C$_{1-10}$ alkyl), —O—(C$_{1-6}$ alkyl), —CF$_3$, NO$_2$, CN, and halo; naphthalenyl; or naphthalenyl substituted with at least one substituent selected from —(C$_{1-10}$ alkyl), —O—(C$_{1-6}$ alkyl), —(C$_{1-6}$ haloalkyl), NO$_2$, CN, and halo, when W$^1$ is —S(=O)$_2$—.

The compound of Formula 1 according to any of the embodiments may be substituted with a detectable label. The detectable label may be an optical label, an electrical label, a magnetic label, or an indirect label. The optical label, as a material generating a detectable optical signal, may be a radioactive material or a chromogenic material such as a fluorescent material. The indirect label may refer to a material that may generate a detectable label by binding to a specific material such as an enzyme which converts a substrate into a chromogenic material, a substrate thereof, or a particular material such as an antibody or an antigen. The optical label may be an isotope of any element that constitutes the compound of Formula 1. Accordingly, the compound of Formula 1 may be substituted with an isotope, for example, a radioactive isotope, of at least one of the elements which constitute the compound of Formula 1. Examples of the isotope may include $^2$H (represented also as D for deuterium), $^3$H (represented also as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The compound of Formula 1 substituted with a detectable label, according to an embodiment, may be used to identify the location of JAK in a cell or subject. Thus, the compound of Formula 1 substituted with a detectable label may be used to identify and treat a site of diseases related to increased activity of JAK.

The compound according to any of the embodiments may be in the form of a pharmaceutically acceptable salt thereof. The salt may be a common acid addition salt used in the art of JAK inhibitors, for example, a salt derived from an inorganic salt such as hydrochloric acid, bromic acid, sulfuric acid, sulfamic acid, phosphoric acid, or nitric acid; or a salt derived from an organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. The salt may be in the form of a common metal salt, for example, a salt derived from a metal such as lithium, sodium, potassium, magnesium, or calcium. The acid addition salt or the metal salt may be prepared by a conventional method.

The compound according to any of the embodiments may be in the form of a solvate thereof. A "solvate" refers to a complex or aggregate of at least one solute molecule, that is, the compound of Formula 1 or a pharmaceutically acceptable salt thereof, and at least one solvent molecule. The solvate may be a complex or aggregate of the compound of Formula 1 or a pharmaceutically acceptable salt thereof, with, for example, water, methanol, ethanol, isopropanol, or acetic acid.

The compound according to any of the embodiments may be in the form of a stereoisomer thereof. The stereoisomer may be any stereoisomer, including an enantiomer or a diastereomer. The compound according to any of the embodiments may be in a stereoisomerically pure form or a mixture of at least one stereoisomer, for example, a racemic mixture. Isolation of specific stereoisomers may be carried out by one of conventional methods known in the art. In some embodiments, the compound may be in the form of a stereoisomer thereof having a greater JAK inhibition effect, for example, by 3 to 40 fold, relative to that of a racemic mixture thereof. By using a specific stereoisomer of the compound, a dose of the compound may be reduced. For example, a compound of Example 5 ($IC_{50}$ value=8.5 nM) having the R configuration may have about 3.5-fold greater JAK1 inhibition activity than that of a compound of Example 55 ($IC_{50}$ value=29.3 nM), which is a racemic mixture of the compound of Example 5. Accordingly, by isolation of a specific stereoisomer, for example, an enantiomer or a diastereomer, having a greater JAK inhibition effect, JAK-related diseases may be more efficiently treated.

With regard to the compounds according to any of the embodiments, pharmaceutical compositions, and methods according to embodiments of the present disclosure, the following terms may have the following meanings unless stated otherwise.

The term "alkyl" as used herein may refer to a linear or branched monovalent saturated hydrocarbon group. Unless stated otherwise, in general the alkyl group may include 1 to 10 carbon atoms, 1 to 8 carbon atoms, 1 to 6 carbon atoms, 1 to 4 carbon atoms, or 1 to 3 carbon atoms. Examples of the alkyl group may include methyl, ethyl, propyl (for example, n-propyl and isopropyl), butyl (for example, n-butyl, isobutyl, or t-butyl), pentyl (for example, n-pentyl, isopentyl, and neopentyl), n-hexyl, n-heptyl, n-octyl, n-nonyl, and n-decyl.

The term "alkenyl" may refer to a linear or branched monovalent unsaturated hydrocarbon group having at least one carbon-carbon double bond. Unless stated otherwise, in general the alkenyl group may include 2 to 10 carbon atoms, 2 to 8 carbon atoms, 2 to 6 carbon atoms, 2 to 4 carbon atoms, or 2 to 3 carbon atoms. Examples of the alkenyl group may include ethenyl, n-propenyl, isopropenyl, n-but-2-enyl, cyclohexenyl, and n-hex-3-enyl.

The term "alkynyl" may refer to a linear or branched monovalent unsaturated hydrocarbon group having at least one carbon-carbon triple bond. Unless stated otherwise, in general the alkynyl group may include 2 to 10 carbon atoms, 2 to 8 carbon atoms, 2 to 6 carbon atoms, 2 to 4 carbon atoms, or 2 to 3 carbon atoms. Examples of the alkynyl group may include ethynyl, n-propynyl, n-but-2-ynyl, and n-hex-3-ynyl.

The term "haloalkyl" may refer to an alkyl group having at least one halogen substituent group. Examples of the haloalkyl may include —$CF_3$, —$C_2F_5$, —$CHF_2$, —$CCl_3$, —$CHCl_2$, and —$C_2Cl_5$. Unless stated otherwise, in general the haloalkyl group may include 1 to 6 carbon atoms, 1 to 4 carbon atoms, or 1 to 3 carbon atoms.

The term "aryl" may refer to an aromatic hydrocarbon group having a monocyclic or polycyclic ring. The polycyclic ring may have a fused ring (for example, naphthalene) and/or a non-fused ring (for example, biphenyl). The polycyclic ring may have, for example, 2, 3, or 4 rings. Unless stated otherwise, in general the aryl group may have 5 to 20 ring carbon atoms), 6 to 15 carbocyclic atoms, 6 to 12 carbocyclic atoms, or 6 to 10 carbocyclic atoms. Examples of the aryl group may include phenyl, naphthalenyl (for example, naphthalene-1-yl and naphthalene-2-yl), biphenyl, anthracenyl, and phenanthrenyl.

The term "cycloalkyl" may refer to a non-aromatic carbocyclic group, for example, a cyclic alkyl, alkenyl or alkynyl group. The cycloalkyl group may include a monocyclic or polycyclic ring. The polycyclic ring may have, for example, 2, 3, or 4 fused rings. Unless stated otherwise, in general the cycloalkyl group may include 3 to 10 carbocyclic atoms, or 3 to 7 carbocyclic atoms. Examples of the cycloalkyl group may include cyclopropyl, cyclobutyl, cyclopentyl, cyclohexyl, cycloheptyl, cyclohexadienyl, cycloheptatrienyl, norbornyl, norcarnyl, and adamantyl.

The term "heterocycloalkyl" may refer to a non-aromatic heterocyclic group containing at least one heteroatom selected from N, O, and S as a ring-forming member. The heterocycloalkyl group may include a monocyclic or polycyclic structure having, for example, 2, 3, or 4 fused rings. Examples of the heterocycloalkyl group may include morpholinyl, thiomorpholinyl, piperazinyl, tetrahydrofuranyl, tetrahydrothienyl, 2,3-dihydro-benzofuryl, 1,3-benzodioxol, benzo-1,4-dioxane, piperidinyl, pyrrolidinyl, isooxazolidinyl, isothiazolidinyl, pyrazolidinyl, oxazolidinyl, and thiazolidinyl. Unless stated otherwise, the heterocycloalkyl group may include 3 to 10 ring-forming atoms, 3 to 7 ring-forming atoms, 5 to 7 ring-forming atoms, or 5 to 6 ring-forming atoms.

The term "heteroaryl" may refer to a monovalent aromatic group including at least one heteroatom selected from N, O, and S as a ring-forming atom. The heteroaryl group may include a monocyclic or polycyclic structure. The polycyclic ring may have, for example, 2, 3, or 4 condensed rings. Unless stated otherwise, in general the heteroaryl group may include 3 to 10 ring atoms, 3 to 7 ring atoms, or 3 to 5 ring atoms. The heteroaryl group may include 1, 2, or 3 heteroatoms. Examples of the heteroaryl group may include pyridyl, N-oxopyridyl, pyrimidinyl, pyrazinyl, pyridazinyl, triazinyl, furyl, quinolyl, isoquinolyl, thienyl, imidazolyl, furanyl, thiazolyl, indolyl, pyryl, oxazolyl, benzofuryl, benzothienyl, benzthiazolyl, iso-oxazolyl, pyrazolyl, triazolyl, tetrazolyl, indazolyl, 1,2,4-thiadiazolyl, isothiazolyl, benzothienyl, purinyl, benzimidazolyl, and indolinyl.

The term "halo" or "halogen" may refer to fluoro, chloro, bromo, or iodo.

The term "arylalkyl" may refer to a substituted alkyl group including an aryl group as a substituent. The terms "aryl" and "alkyl" are the same as defined above.

The term "heteroarylalkyl" may refer to a substituted alkyl group including a heteroaryl group as a substituent. The terms "heteroaryl" and "alkyl" are the same as defined above.

In another aspect of the present disclosure, there is provided a pharmaceutical composition including a therapeutically effective amount of the compound of Formula 1, or a pharmaceutically acceptable salt, solvate, or stereoisomer thereof, as defined above, and a pharmaceutically acceptable carrier.

The pharmaceutical composition may be for the treatment of a JAK-related disease. The disease may be an autoimmune disease, an immune system dysfunction, a viral disease, an allergic disease, a skin disease, an IL-6 pathway-related disease, an immune response, a hyperproliferative disorder, or a cancer. The autoimmune disease may be, for example, skin disease, multiple sclerosis, rheumatoid arthritis, juvenile arthritis, type I diabetes, lupus, psoriasis, inflammatory bowel disease, ulcerative colitis, Crohn's disease, or autoimmune thyroid disease. The immune system dysfunction may be, for example, allograft rejection, a graft-versus-host disease, an allograft rejection reaction, or a graft-versus-host reaction. The viral disease may be, for example, Epstein-Barr virus (EBV), hepatitis B, hepatitis C, HIV, HTLV 1, chickenpox, herpes zoster virus (VZV), or human papillomavirus (HPV) disease. The cancer may be, for example, prostate cancer, kidney cancer, liver cancer, pancreatic cancer, gastric cancer, breast cancer, lung cancer, head and neck cancer, glioblastoma, leukemia, lymphoma, or multiple myeloma. The immune response may be, for example, diarrhea, skin irritation, skin rash, contact dermatitis, or allergic contact hypersensitivity. The allergic disease may be asthma, food allergy, atopic dermatitis, or rhinitis. Examples of the IL-6 pathway-related disease may include Castleman's disease and Kaposi's sarcoma In the pharmaceutical composition, the term "therapeutically effective amount" may refer to an amount sufficient to exhibit a therapeutic effect when administered to a subject in need of treatment. The term "treatment" may refer to treatment of a disease or a medical symptom, for example, a JAK-related disease, in a mammal, including humans, and may include the following: (a) preventing the occurrence of a disease or medical symptom, i.e., prophylactic treatment of a patient; (b) alleviating a disease or medical symptom, i.e., removal or recovery of a disease or medical condition in a patient; (c) suppressing a disease or medical symptom, i.e., slowing or stopping the progression of a disease or medical symptom in a subject; or (d) alleviating a disease or medical symptom in a subject. The term "effective amount" may be properly chosen by one of ordinary skill in the art. For example, the "effective amount" may be about 0.01 mg to about 10,000 mg, about 0.1 mg to about 1,000 mg, about 1 mg to about 100 mg, about 0.01 mg to about 1,000 mg, about 0.01 mg to about 100 mg, about 0.01 mg to about 10 mg, or about 0.01 mg to about 1 mg.

In the pharmaceutical composition, the compound and the pharmaceutically acceptable salt, solvate, or stereoisomer thereof may be the same as described above.

In the pharmaceutical composition, the "pharmaceutically acceptable carrier" may refer to a material, in general, an inert material used in combination with an active ingredient to help application of the active ingredient. The carrier may include a common pharmaceutically acceptable excipient, additive, or diluent. The carrier may include, for example, at least one selected from a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The pharmaceutical composition may be orally or non-orally administered. The non-oral administration may include, for example, intravenous, intraperitoneal, subcutaneous, rectal, or local administration. Therefore, in some embodiments, the pharmaceutical composition may be formulated in any of a variety of forms, including as a tablet, a capsule, an aqueous solution, or a suspension. For example, in an oral tablet of the pharmaceutical composition, in general an excipient such as lactose or corn starch, and a lubricating agent such as magnesium stearate may be added. In an oral capsule of the pharmaceutical composition, lactose and/or dried corn starch may be used as a diluent. To formulate an oral aqueous suspension, the active ingredient may be bound with an emulsifier and/or a suspending agent. For example, a certain sweetening agent and/or flavoring agent may be added, if needed. For intramuscular, intraperitoneal, subcutaneous, and intravenous administration, usually a sterile solution of the active ingredient may be prepared. It may be required that the pH of this solution be adjusted to a suitable level, and that the solution is buffered. For intravenous administration, a total concentration of solute may need to be adjusted to render the preparation isotonic. The pharmaceutical composition may be in the form of an aqueous solution including a pharmaceutically acceptable carrier such as saline at a pH level of 7.4. This solution may be introduced into an intramuscular bloodstream of a patient by local bolus injection.

The compound of Formula 1 defined in any of the embodiments of the present invention may have an effect of inhibiting the activity of one or more JAKs. The term "inhibition" may refer to reducing the activity of one or two or more kinases.

The "JAK" as used herein may include any enzyme in the Janus kinase family. In some embodiments, the compound may inhibit the activity of JAK1, JAK2, JAK3, and TYK2. In some embodiments, the compound may selectively inhibit the activity of JAK1, JAK2, and TYK2. In some other embodiments, the compound may selectively inhibit the activity of JAK1 alone. For example, a compound of Example 44 may inhibit the activity of JAK1, JAK2, JAK3, and TYK2. For example, the compound of Example 44 may inhibit the activities of JAK1, JAK2, JAK3, and TYK2 by 100%, 96%, 96%, and 98%, respectively, at a concentration of 1 uM. A compound of Example 39 may selectively inhibit the activity of JAK1, JAK2, and TYK2. For example, the compound of Example 39 may inhibit the activities of JAK1, JAK2, and TYK2 by 99%, 95%, and 93%, respectively, at a concentration of 1 uM, while the compound of Example 39 may inhibit the activity of JAK3 by only 65%. A compound of Example 60 may selectively inhibit the activity of JAK1. For example, the compound of Example 60 may inhibit the activities of JAK2, JAK3, and TYK2 by −3%, −14%, and 0%, respectively, at a concentration of 1 uM inhibition, while inhibiting the activity of JAK1 by 96%. Here, the inhibition effect was evaluated according to the degree to which JAK inhibits the conversion of ATP to ADP in the presence of a compound according to an embodiment. When a measured absorbance is lower than that of a standard absorption curve, the inhibition effect has a negative value lower than a negative control value, which substantially indicates a 0% inhibition effect having no inhibitory efficacy.

A compound according to any of the embodiments may be selective for a particular type of JAK. The term "selective" or "selectively" as used herein may indicate that a certain compound according to an embodiment has a greater inhibitory effect on a specific JAK than on at least one other JAK. In some embodiments, the compound according to an embodiment may be an inhibitor selective for JAK1 or JAK2, as compared to JAK3 or TYK2. In some embodiments, the compound according to an embodiment may be an inhibitor selective for JAK1, as compared to JAK2, JAK3, and/or TYK2. In particular, since a JAK3 inhibitor may exhibit an immune inhibition effect, a JAK2-selective inhibitor, as opposed to the JAK3-selective inhibitor, may be used in treating cancer such as myeloma or myelofibrosis without an immune inhibitory side effect. Selectivity for a specific JAK may be at least about 5 fold, 10 fold, 20 fold, 40 fold, 100 fold, 200 fold, 500 fold, or 1000 fold that of other JAKs. In comparison of a inhibitory capacity (%) at 1 uM, a compound according to an embodiment may have 44-fold selectivity for JAK1 over JAK2 (−91<JAK1(%)/JAK2(%)<44). In some embodiments, the compound may have 40-fold selectivity for JAK1 over JAK3 (−65<JAK1(%)/JAK3(%)<40). In some other embodiments, the compound may have 62-fold selectivity for JAK1 over JAK2 (−19.75<JAK1(%)/TYK2(%)<62). The selectivity may be measured by any of conventional methods known in the art. The selectivity may be tested at the $K_m$ of each enzyme.

The pharmaceutical composition according to any of the embodiments may be used in combination with at least one other therapeutic agent used for the treatment of JAK-related diseases. Examples of the therapeutic agent may include a chemotherapeutic agent, an anti-inflammatory agent, an immunosuppressive agent, and an anti-cancer agent. Combined use of the pharmaceutical composition according to any of the embodiments with a therapeutic agent for the treatment of multiple myeloma may improve therapeutic response without additional toxicity problems, as compared to when a JAK inhibitor is prescribed alone. Examples of the therapeutic agent that may be used in combination for the treatment of multiple myeloma may include melphalan, a melphalan and prednisone combination, doxorubicin, dexamethasone, and Velcade. Such combination therapy may provide a synergistic effect. Furthermore, the compound according to any of the embodiments may solve a drug tolerance problem of dexamethasone in the treatment of multiple myeloma. The therapeutic agent used in the combination therapy may be administered at once or continuously in combination with a JAK inhibitor. In some embodiments, the therapeutic agent and a JAK inhibitor may be administered simultaneously or sequentially, for example, separately from each other.

In another aspect of the present disclosure, a use of the compound of Formula 1, or a pharmaceutically acceptable salt, solvate, or stereoisomer thereof, in the treatment of a JAK-related disease, is provided.

In another aspect of the present disclosure, a use of the compound of Formula 1, or a pharmaceutically acceptable salt, solvate, or stereoisomer thereof, in preparation of a medicine for the treatment of a JAK-related disease, is provided.

In another aspect of the present disclosure, a method of inhibiting the activity of a JAK is provided, the method including inhibiting the activity of the JAK by contacting, with the JAK, the compound of Formula 1 or a pharmaceutically acceptable salt, solvate, or stereoisomer thereof as defined above.

In some embodiments of the method, the contacting may be performed in vitro or in vivo. In some embodiments of the method, the JAK may be present in the cell. The JAK may be JAK1, JAK2, JAK3, or TYK2.

The inhibiting may be reducing the activity of the JAK. The inhibiting may be reducing the activity of a particular type of JAK by a higher degree, as compared to that of other types of JAK. For example, the inhibiting may include selectively inhibiting JAK1 when in the presence of JAK1 and at least one of JAK2, JAK3, and TYK2.

In another aspect of the present disclosure, a method of treating a disease in a subject is provided, the method including administering a therapeutically effective amount of the compound of Formula 1, or a pharmaceutically acceptable salt, solvate, or stereoisomer thereof, as defined above, to a subject.

In some embodiments of the method, a suitable administration route may be selected by one of ordinary skill in the art depending on the condition of a subject. The administering may be by oral, non-oral, or local administration.

In some embodiments of the method, a dosage amount may be varied depending on various factors, including the condition of a patient, an administration route, and a doctor's decision. A therapeutically effective amount may be estimated based on a dose-response curve obtained through an in vitro or animal model test. A ratio and concentration of the compound according to any of the embodiments in a pharmaceutical composition to be administered may be determined according to chemical properties of the compound, the administration route, and a therapeutic dosage amount. A dosage administered to a subject may be about 1 µg/kg to about 1 g/kg per day, or about 0.1 mg/kg to about 500 mg/kg per day. The dosage level may be varied depending on the age, weight, susceptibility, or condition of the individual.

In some embodiments of the method, the disease may be a JAK-related disease. The disease may be an autoimmune disease, an immune system dysfunction, a viral disease, an allergic disease, a skin disease, a IL-6 pathway-related disease, an immune response, a hyperproliferative disorder, or a cancer as described above. In some embodiments, a therapeutically effective amount of the compound of Formula 1 according to any of the embodiments, or a pharmaceutically acceptable salt, solvate, or stereoisomer thereof, may be administered in combination with at least one other therapeutic agent for the treatment of JAK-related diseases. This therapeutic agent may be the same as described above.

A compound of Formula 1, or a pharmaceutically acceptable salt, solvate, or stereoisomer thereof according to embodiments, may be prepared by a method illustrated in Reaction Scheme 1.

(Reaction Scheme 1)

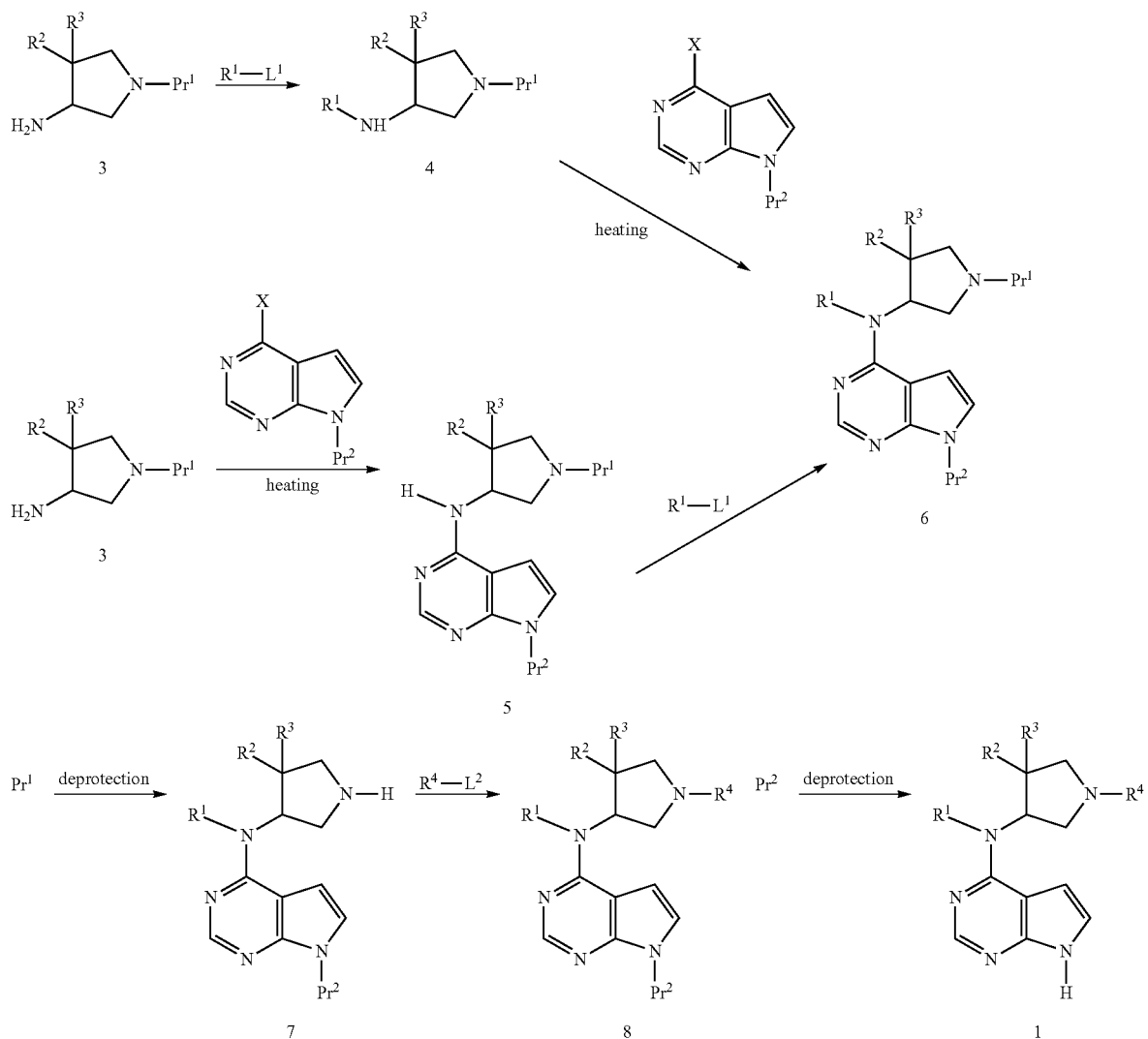

In Reaction Scheme 1, $L^1$ and $L^2$ in Formulae 3, 4, 5, 6, 7, and 8 may be a leaving group, $Pr^1$ and $Pr^2$ may be an amino-protecting group, X may be F, Cl, Br, or I, and $R^1$, $R^2$, $R^3$, and $R^4$ may be the same as described above in connection with Formula 1.

The method of preparing the compound of Formula 1 according to an embodiment may include:

(a) reacting a compound of Formula 3 or a salt thereof with a compound of the formula $R^1$—$X^1$ to form a compound of Formula 4; and reacting the compound of Formula 4 with 6-halo-7-deazapurine to form a compound of Formula 6 by; or (b) reacting a compound of Formula 3 or a salt thereof with 6-halo-7-deazapurine to form a compound of Formula 5; and reacting the compound of Formula 5 with a compound of the formula $R^1$—$X^1$ to form a compound of Formula 6;

(c) deprotecting a nitrogen of a pyrrolidine ring in the compound of Formula 6 to form a compound of Formula 7;

(d) reacting the compound of Formula 7 with a compound of the formula $R^4$—$X^2$ to form a compound of Formula 8; and (e) deprotecting the compound of Formula 8 to prepare the compound of Formula 1.

In the method, the step (a) including the "reacting a compound of Formula 3 or a salt thereof with a compound of the formula $R^1$—$X^1$ to form a compound of Formula 4" and the "reacting the compound of Formula 4 with 6-halo-7-deazapurine to form a compound of Formula 6" may include, for example, alkylation (for example, methylation), alkenylation, or alkynylation.

In the method, the "reacting the compound of Formula 4 with 6-halo-7-deazapurine to form generating a compound of Formula 6" in step (a) and the "reacting a compound of Formula 3 or a salt thereof with 6-halo-7-deazapurine Formula 3 to form a compound of Formula 5" in step (b) may be performed in a suitable solvent while being heated or under reflux conditions. The 6-halo-7-deazapurine may be commercially purchased for use. The halo may be, for example, chloro.

In the method, the step (c) of "deprotecting a nitrogen of a pyrrolidine ring in the compound of Formula 6 to form a compound of Formula 7"; and the step (e) of "deprotecting the compound of Formula 8 to prepare the compound of Formula 1" may be performed by any known deprotection method.

In the method, the step (d) of "reacting the compound of Formula 7 with a compound of the formula $R^4$—$X^2$ to form a compound of Formula 8" may be performed by substitution of $X^2$ with N.

With regard to the above-described method, the term "leaving group" as used herein may refer to a functional group or atom that may be replaceable by another functional group or atom in a substitution reaction, for example, a nucleophilic substitution reaction. For examples, typical examples of the leaving groups may include a chloro group, a bromo group, and an iodine group; a sulfonic ester group, for example, tosylate, brosylate, nosylate, and the like; and an alkyloxy group, for example, acetoxy, trifluoroacetoxy, and the like.

The term "protected" may indicate that at least one functional group of a compound is protected from undesirable reactions by using a protecting group or blocking group. Functional groups that may be protected may include a carbamate (for example, tert-butoxycarbonyl), which is a typical protecting group for an amino group.

The term "amino-protecting group" as used herein may refer to a suitable protecting group for preventing undesirable reactions at an amino group. Typical examples of the amino-protecting group may include tert-butoxycarbonyl (BOC), trityl (Tr), benzyloxycarbonyl (Cbz), 9-fluorenyl-methoxycarbonyl (Fmoc), formyl, trimethylsilyl (TMS), and tert-butyldimethylsilyl (TBS).

In another aspect of the present disclosure, a method of preparing a compound of Formula 1 according to an embodiment is provided, the method including reacting a compound of Formula 9 or a salt thereof with a compound of the formula $R^4$-$L^2$ to form the compound of Formula 2.

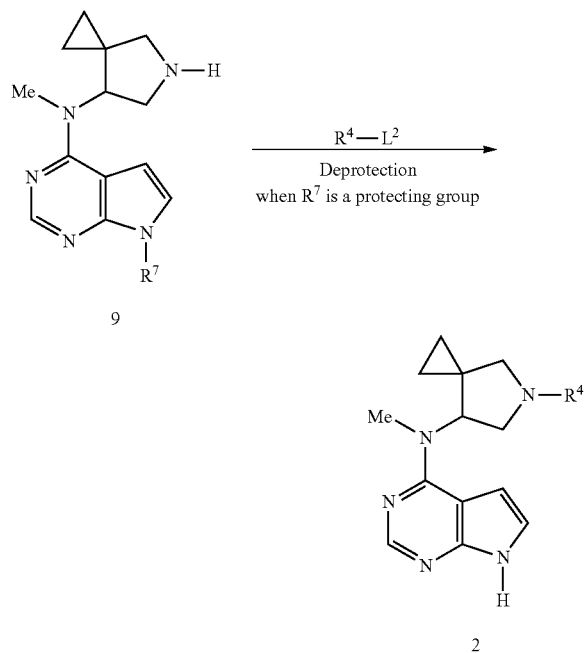

(Reaction Scheme 2)

In Reaction Scheme 2, $R^7$ may be H or an amino-protecting group, $L^2$ may be a leaving group, and $R^4$ may be the same as described above in connection with Formula The compound of Formula 9 may be prepared by a method known in the art. For example, the compound of Formula 9 may be prepared by reacting (R)-5-benzyl-N-methyl-5-azaspiro[2.4]heptan-7-amine and 6-halo-7-deazapurine in the presence of potassium carbonate while heating or refluxing, to obtain (R)-N-(5-benzyl-5-azaspiro[2.4]heptan-7-yl)-N-methyl-7H-pyrrolo[2,3-d]pyrimidin-4-amine, and then by reacting the obtained product with hydrogen in the presence of palladium/carbon as a catalyst. When $R^7$ is an amino-protecting group, this amino-protecting group may be introduced by a common method. The (R)-5-benzyl-N-methyl-5-azaspiro[2.4]heptan-7-amine and the 6-halo-7-deazapurine may be synthesized by one of ordinary skill in the art or commercially purchased for use. When $R^7$ is an amino-protecting group, the method may optionally further include a deprotection step.

The compound of Formula 2 may be prepared by reacting a compound of Formula 9 or a salt thereof with a compound of the formula $R^4$-$L^2$ in a suitable solvent such as N,N-dimethylformamide. For example, by reacting the compound of Formula 9 or a salt thereof with 1-bromobutane in N,N-dimethylformamide in the presence of N,N-diisopropylethylamine at room temperature, (R)-N-(5-butyl-5-azaspiro[2.4]heptan-7-yl)-N-methyl-7H-pyrrolo[2,3-d]pyrimidin-4-amine may be prepared.

In the above-described methods, the compounds according to embodiments may be prepared using a general method or process, or may be prepared from a starting material which is easily obtainable, based on other information easily available to one of ordinary skill in the art. Detailed synthesis processes of the compounds according to embodiments are described in examples which will be described later.

The compounds according to embodiments, including salts thereof and solvates thereof, including hydrates thereof, may be prepared using a general organic synthesis method widely known in the art, through one of the available multiple synthesis pathways.

Synthesis reactions of compounds according to embodiments may be performed in a suitable solvent that may be easily chosen by one of ordinary skill in the art of organic synthesis. The suitable solvent may be substantially non-reactive to a starting material or reactant, an intermediate, or a reaction product in a reaction temperature range, i.e., from the freezing point to the boiling point of the solvent. The given reaction may be performed in a solvent or in a mixture of at least two solvents. A suitable solvent may be selected for each specific reaction stage.

Synthesis of a compound according to any of the embodiments may include protecting and deprotecting various chemical functional groups. Whether or not there is a need to perform a protecting and deprotecting process, and selection of a suitable protecting group, may be easily determined by one of ordinary skill in the art.

The synthesis reaction may be observed using any suitable method known in the art. For example, formation of reaction products may be observed by spectroscopy, for example, nuclear magnetic resonance spectroscopy (for example, $^1$H or $^{13}$C), infrared spectroscopy, spectrophotometry (for example, UV-visible), or mass spectrometry; or chromatography, for example, high-performance liquid chromatography (HPLC) or thin layer chromatography (TLC). Compounds according to the embodiments may be synthesized through numerous known synthesis pathways disclosed in documents.

Advantageous Effects of the Invention

In an aspect of the present disclosure, a compound of Formula 1 according to any of the embodiments, or a pharmaceutically acceptable salt, solvate, or stereoisomer thereof, may be used as a JAK inhibitor.

In another aspect of the present disclosure, a pharmaceutical composition including the compound of Formula 1 according to any of the embodiments, or a pharmaceutically acceptable salt, solvate, or stereoisomer thereof, may be used in treating JAK-related diseases.

In another aspect of the present disclosure, by a method of regulating the activity of a JAK by using the compound of Formula 1 according to the any of the embodiments, or a pharmaceutically acceptable salt, solvate, or stereoisomer thereof, the activity of the JAK may be efficiently regulated.

In another aspect of the present disclosure, by a method of treating a disease in a subject by administering the compound of Formula 1 according to any of the embodiments, or a pharmaceutically acceptable salt, solvate, or stereoisomer thereof, to a subject, the disease of the subject may be efficiently treated.

In another aspect of the present disclosure, by a method of preparing the compound of Formula 1 according to any of the embodiments, the compound of Formula 1 may be efficiently prepared.

DESCRIPTION OF THE DRAWING

FIG. 1 is a graph of hind paw edema volume in arthritic model mice with respect to drug administration time (days) after the first immunization.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Unless stated otherwise in the following examples, reagents, starting materials, and solvents used in the following examples were purchased from commercial providers (for example, Aldrich, Fluka, Sigma, Acros, DAEJUNG Chemicals & Metals Co., Ltd., TCI, and the like), and used without additional purification. Purification involved in synthesis processes was performed by flash column chromatography using Silica gel 60 (0.040~0.063 mm) (available from Merck).

1. INTERMEDIATE PREPARATION EXAMPLE

Some compounds used in the following examples were synthesized using intermediates which were synthesized as follows.

(1.1) Intermediate 1: (R)-N-(5-benzyl-5-azaspiro[2.4]heptan-7-yl)-N-methyl-7H-pyrrolo[2,3-d]pyrimidin-4-amine

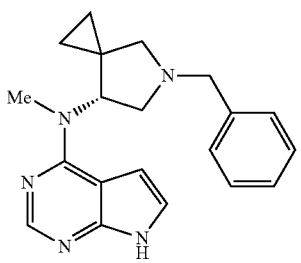 [SMILES: CN(c1ncnc2[nH]ccc12)[C@H]1CN(Cc2ccccc2)CC12CC2]

2.000 g of (R)-5-benzyl-N-methyl-5-azaspiro[2.4]heptan-7-amine (available from Sundia, China) was placed into a 100-mL round-bottomed flask, and 40.0 mL of distilled water was added thereto. After 1.490 g of 6-chloro-7-deazapurine (available from Acros) was added thereto, 2.560 g of potassium carbonate was added to the reaction mixture. The resulting mixture was refluxed for about 36 hours, and then cooled down at room temperature. The resulting reaction mixture was extracted three times with 40.0 mL of dichloromethane to collect an organic phase. The collected organic phase was concentrated under reduced pressure. The obtained residue was purified by flash column chromatography (MeOH:DCM=2:98).

As a result, 2.370 g of (R)-N-(5-benzyl-5-azaspiro[2.4]heptan-7-yl)-N-methyl-7H-pyrrolo[2,3-d]pyrimidin-4-amine was obtained with a yield of 77.0%.

$^1$H NMR (400 MHz, CDCl$_3$) δ 11.20 (s, 1H), 8.21 (s, 1H), 7.45-7.19 (m, 5H), 7.03 (s, 1H), 6.57 (s, 1H), 5.57 (s, 1H), 3.64 (dd, J=31.2, 12.8 Hz, 2H), 3.52 (s, 3H), 2.95 (s, 2H), 2.76 (d, J=8.8 Hz, 1H), 2.51 (d, J=8.8 Hz, 1H), 0.95 (d, J=9.3 Hz, 1H), 0.63 (s, 2H), 0.47 (d, J=9.7 Hz, 1H).

(1.2) Intermediate 2: (R)-N-methyl-N-(5-azaspiro[2.4]heptan-7-yl)-7H-pyrrolo[2,3-d]pyrimidin-4-amine

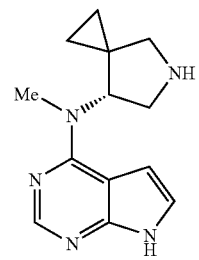 [SMILES: CN(c1ncnc2[nH]ccc12)[C@H]1CNCC12CC2]

2.350 g of (R)-N-(5-benzyl-5-azaspiro[2.4]heptan-7-yl)-N-methyl-7H-pyrrolo[2,3-d]pyrimidin-4-amine was placed into a 50-mL round-bottomed flask and then dissolved with 25.0 mL of methanol. After 2.350 g of a 10 w/w % palladium/carbon (available from Acros) was added thereto, a hydrogen-containing balloon was installed on the reaction flask. The reaction mixture was vigorously stirred for about 39 hours, and then filtered using a Celite 545 filter (Celite™ 545) (available from DAEJUNG Chemicals & Metals Co., Ltd.). The resulting filtrate was concentrated under reduced pressure.

As a result, 1.510 g of (R)-N-methyl-N-(5-azaspiro[2.4]heptan-7-yl)-7H-pyrrolo[2,3-d]pyrimidin-4-amine was obtained with a yield of 88.0%.

$^1$H NMR (400 MHz, CDCl$_3$) δ 10.77 (s, 1H), 8.25 (s, 1H), 7.07 (d, J=3.5 Hz, 1H), 6.58 (d, J=3.5 Hz, 1H), 5.38 (dd, J=23.1, 16.5 Hz, 1H), 3.72-3.56 (m, 1H), 3.49 (d, J=11.7 Hz, 4H), 3.30-3.11 (m, 2H), 2.92 (d, J=11.2 Hz, 1H), 0.93 (d, J=10.9 Hz, 1H), 0.82-0.68 (m, 2H), 0.68-0.46 (m, 1H).

EXAMPLE 1

(R)-N-(5-butyl-5-azaspiro[2.4]heptan-7-yl)-N-methyl-7H-pyrrolo[2,3-d]pyrimidin-4-amine

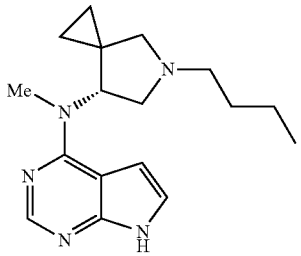 [SMILES: CCCCN1C[C@H](N(C)c2ncnc3[nH]ccc23)C2(CC2)C1]

70.0 mg of (R)-N-methyl-N-(5-azaspiro[2.4]heptan-7-yl)-7H-pyrrolo[2,3-d]pyrimidin-4-amine was placed into a 5-mL round-bottomed flask, and then dissolved with 1.0 mL of N,N-dimethylformamide. After 59.3 mg of 1-bromobutane (available from Sigma-Aldrich) was added to the solution, 0.100 mL of N,N-diisopropylethylamine (available from DAEJUNG Chemicals & Metals Co., Ltd.) was added thereto. The resulting reaction solution was stirred at room temperature overnight, and then concentrated under reduced pressure. The resulting residue was purified by flash column chromatography (MeOH:DCM=2:98). The collected fraction was concentrated under reduced pressure, and then further under vacuum. As a result, 35.0 mg of (R)-N-(5-butyl-5-azaspiro[2.4]heptan-7-yl)-N-methyl-7H-pyrrolo[2,3-d]pyrimidin-4-amine was obtained with a yield of 40.7%.

$^1$H NMR (400 MHz, CDCl$_3$) δ 9.51 (s, 1H), 8.23 (s, 1H), 7.02 (s, 1H), 6.61 (s, 1H), 5.56 (s, 1H), 3.49 (s, 3H), 2.96 (s, 2H), 2.78 (s, 1H), 2.52 (s, 3H), 1.53-1.51 (m, 2H), 1.44-1.35 (m, 2H), 0.97 (t, J=7.2 Hz, 4H), 0.74 (s, 2H), 0.51 (d, J=9.2 Hz, 1H). LRMS (ESI) calcd for (C$_{17}$H$_{25}$N$_5$+H$^+$) 300.2, found 300.2.

Additional compounds according to embodiments described below were synthesized in a similar manner as described in Example 1.

EXAMPLE 2

(R)-N-methyl-N-(5-pentyl-5-azaspiro[2.4]heptan-7-yl)-7H-pyrrolo[2,3-d]pyrimidin-4-amine

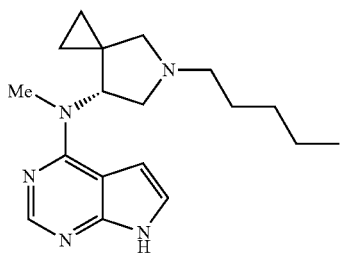 [SMILES: CCCCCN1C[C@H](N(C)c2ncnc3[nH]ccc23)C2(CC2)C1]

$^1$H NMR (400 MHz, CDCl$_3$) δ 11.29 (s, 1H), 8.20 (s, 1H), 7.06 (d, J=3.2 Hz, 1H), 6.60 (d, J=3.2 Hz, 1H), 5.57 (s, 1H), 3.49 (s, 3H), 3.14-2.99 (m, 2H), 2.81 (s, 1H), 2.57-2.48 (m, 3H), 1.71-1.66 (m, 4H), 1.37-1.33 (m, 2H), 0.97-0.91 (m, 4H), 0.79-0.66 (m, 2H), 0.55-0.50 (m, 1H). LRMS (ESI) calcd for (C$_{18}$H$_{27}$N$_5$+H$^+$) 314.2, found 314.2.

EXAMPLE 3

(R)-2-methyl-1-(7-(methyl(7H-pyrrolo[2,3-d]pyrimidin-4-yl)amino)-5-azaspiro[2.4]heptan-5-yl)propan-1-one

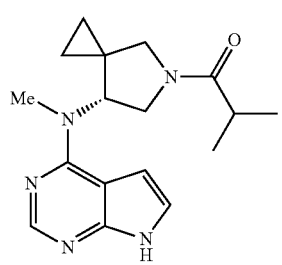 [SMILES: CC(C)C(=O)N1C[C@H](N(C)c2ncnc3[nH]ccc23)C2(CC2)C1]

$^1$H NMR (400 MHz, CDCl$_3$) δ 10.12 (s, 1H), 10.00 (s, 1H), 8.27 (d, J=6.8 Hz, 1H), 7.09-7.02 (m, 1H), 6.60-6.57 (m, 1H), 5.54-5.41 (m, 1H), 4.20-3.79 (m, 2H), 3.48-3.38 (m, 4H), 2.74-2.59 (m, 1H), 1.20-1.15 (m, 6H), 1.10-1.01 (m, 1H), 0.90-0.65 (m, 3H). LRMS (ESI) calcd for (C$_{17}$H$_{23}$N$_5$O+H$^+$) 314.2, found 314.2.

EXAMPLE 4

(R)-2-azido-1-(7-(methyl(7H-pyrrolo[2,3-d]pyrimidin-4-yl)amino)-5-azaspiro[2.4]heptan-5-yl)ethan-1-one

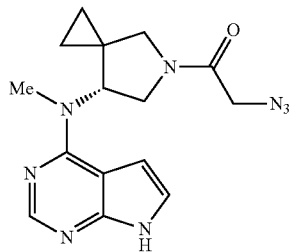

$^1$H NMR (400 MHz, CDCl$_3$) δ 9.39 (s, 1H), 8.25 (d, J=3.2 Hz, 1H), 7.09-7.02 (m, 1H), 6.70-6.59 (m, 1H), 5.52-5.44 (m, 1H), 4.16-4.07 (m, 1H), 3.99-3.85 (m, 3H), 3.84-3.57 (m, 2H), 3.55-3.32 (m, 3H), 1.15-1.00 (m, 1H), 0.92-0.74 (m, 3H). LRMS (ESI) calcd for (C$_{15}$H$_{18}$N$_8$O+H$^+$) 327.2, found 327.1.

EXAMPLE 5

(R)-3-(7-(methyl(7H-pyrrolo[2,3-d]pyrimidin-4-yl)amino)-5-azaspiro[2.4]heptan-5-yl)-3-oxopropanenitrile

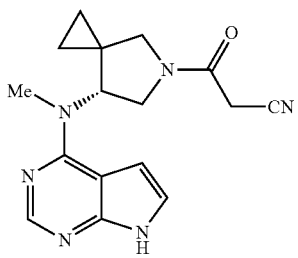

¹H NMR (400 MHz, CDCl₃) δ 10.24 (s, 1H), 8.24 (d, J=4.6 Hz, 1H), 7.16-6.95 (m, 1H), 6.57 (dd, J=7.2, 3.5 Hz, 1H), 5.63-5.34 (m, 1H), 4.27-4.02 (m, 1H), 4.01-3.83 (m, 1H), 3.76 (dd, J=11.4, 2.3 Hz, 1H), 3.51 (d, J=12.4 Hz, 2H), 3.48-3.35 (m, 4H), 1.17-0.96 (m, 1H), 0.84 (ddd, J=19.4, 10.7, 4.3 Hz, 3H). LRMS (ESI) calcd for ($C_{16}H_{18}N_6O+H^+$) 311.2, found 311.2.

EXAMPLE 6

(R)-3-methyl-1-(7-(methyl(7H-pyrrolo[2,3-d]pyrimidin-4-yl)amino)-5-azaspiro[2.4]heptan-5-yl)butan-1-one

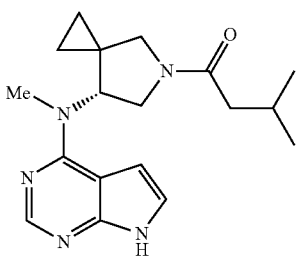 [SMILES: CC(C)CC(=O)N1C[C@H](N(C)c2ncnc3[nH]ccc23)C2(CC2)C1]

¹H NMR (400 MHz, CDCl₃) δ 9.51 (s, 1H), 8.27 (d, J=6.8 Hz, 1H), 7.07-7.02 (m, 1H), 6.60 (d, J=8.8 Hz, 1H), 5.47-5.36 (m, 1H), 4.16-3.74 (m, 3H), 3.49-3.38 (m, 4H), 2.29-2.18 (m, 3H), 1.09-0.98 (m, 7H), 0.90-0.73 (m, 3H). LRMS (ESI) calcd for ($C_{18}H_{25}N_5O+H^+$) 328.2, found 328.2.

EXAMPLE 7

(R)-N-(2-(7-(methyl(7H-pyrrolo[2,3-d]pyrimidin-4-yl)amino)-5-azaspiro[2.4]heptan-5-yl)-2-oxoethyl)acetamide

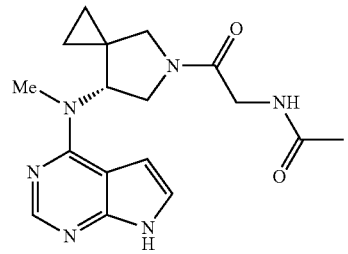 [SMILES: CC(=O)NCC(=O)N1C[C@H](N(C)c2ncnc3[nH]ccc23)C2(CC2)C1]

¹H NMR (400 MHz, CDCl₃) δ 10.53 (d, J=14.4 Hz, 1H), 8.27 (d, J=5.6 Hz, 1H), 7.11 (s, 1H), 6.72 (d, J=18.4 Hz, 1H), 6.58 (s, 1H), 5.46 (dd, J=31.6, 6.4 Hz, 1H), 4.13-4.06 (m, 2H), 4.01-3.94 (m, 1H), 3.92-3.83 (m, 1H), 3.73 (d, J=11.6 Hz, 1H), 3.52 (d, J=12.4 Hz, 1H), 3.43-3.40 (m, 3H), 2.07 (d, J=4.0 Hz, 3H), 1.11-1.01 (m, 1H), 0.90-0.80 (m, 3H). LRMS (ESI) calcd for ($C_{17}H_{22}N_6O_2+H^+$) 343.2, found 343.1.

EXAMPLE 8

(R)-N-methyl-3-(7-(methyl(7H-pyrrolo[2,3-d]pyrimidin-4-yl)amino)-5-azaspiro[2.4]heptan-5-yl)-3-oxopropanamide

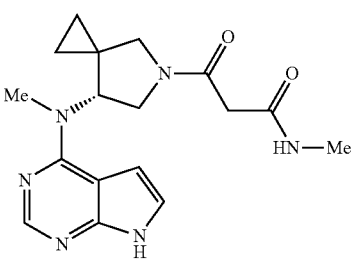 [SMILES: CNC(=O)CC(=O)N1C[C@H](N(C)c2ncnc3[nH]ccc23)C2(CC2)C1]

¹H NMR (400 MHz, CDCl₃) δ 11.96 (d, J=30.6 Hz, 1H), 8.24 (dd, J=6.6, 1.8 Hz, 1H), 8.13 (s, 1H), 7.11 (s, 1H), 6.54 (s, 1H), 5.51-5.34 (m, 1H), 4.13 (ddd, J=21.2, 12.6, 7.5 Hz, 1H), 4.00-3.80 (m, 2H), 3.49 (t, J=11.6 Hz, 1H), 3.40 (d, J=14.5 Hz, 3H), 3.35 (t, J=19.8 Hz, 2H), 2.83 (dd, J=4.5, 2.1 Hz, 3H), 1.11-0.94 (m, 1H), 0.90-0.68 (m, 3H). LRMS (ESI) calcd for ($C_{17}H_{22}N_6O_2+H^+$) 343.2, found 343.1.

EXAMPLE 9

(R)-cyclopropyl(7-(methyl(7H-pyrrolo[2,3-d]pyrimidin-4-yl)amino)-5-azaspiro[2.4]heptan-5-yl)methanone

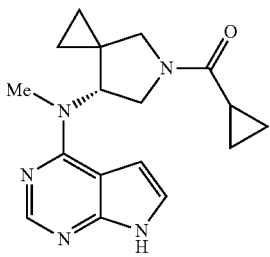 [SMILES: CN(c1ncnc2[nH]ccc12)[C@H]1CN(C(=O)C2CC2)CC12CC2]

$^1$H NMR (400 MHz, CDCl$_3$) δ 10.32 (s, 1H), 8.26 (d, J=8.0 Hz, 1H), 7.07 (d, J=8.0 Hz, 1H), 6.59 (d, J=11.6 Hz, 1H), 5.56-5.39 (m, 1H), 4.36-3.86 (m, 3H), 3.65-3.36 (m, 4H), 1.69-1.55 (m, 1H), 1.11-0.94 (m, 3H), 0.81-0.71 (m, 5H). LRMS (ESI) calcd for (C$_{17}$H$_{21}$N$_5$O+H$^+$) 312.2, found 312.1.

EXAMPLE 10

(R)-1-(4-(7-(methyl(7H-pyrrolo[2,3-d]pyrimidin-4-yl)amino)-5-azaspiro[2.4]heptane-5-carbonyl)piperidin-1-yl)ethan-1-one

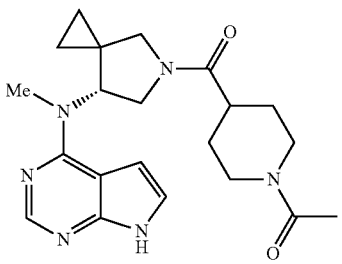 [SMILES: CC(=O)N1CCC(C(=O)N2C[C@H](N(C)c3ncnc4[nH]ccc34)C3(CC3)C2)CC1]

$^1$H NMR (400 MHz, CDCl$_3$) δ 9.80 (s, 1H), 8.28 (dd, J=9.6, 3.2 Hz, 1H), 7.08 (d, J=9.2 Hz, 1H), 6.60 (d, J=2.9 Hz, 1H), 5.49-5.40 (m, 1H), 4.64 (t, J=12.4 Hz, 1H), 4.23-4.02 (m, 1H), 4.00-3.78 (m, 3H), 3.52-3.49 (m, 1H), 3.46 (s, 3H), 3.39 (s, 1H), 3.15-3.10 (m, 1H), 2.66-2.56 (m, 2H), 2.13-2.04 (m, 3H), 1.88-1.70 (m, 2H), 1.12-1.00 (m, 1H), 0.94-0.76 (m, 4H). LRMS (ESI) calcd for (C$_{21}$H$_{28}$N$_6$O$_2$+H$^+$) 397.2, found 397.2.

EXAMPLE 11

(R)-furan-2-yl(7-(methyl(7H-pyrrolo[2,3-d]pyrimidin-4-yl)amino)-5-azaspiro[2.4]heptan-5-yl)methanone

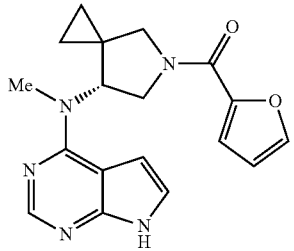 [SMILES: CN(c1ncnc2[nH]ccc12)[C@H]1CN(C(=O)c2ccco2)CC12CC2]

$^1$H NMR (400 MHz, CDCl$_3$) δ 9.91 (s, 1H), 8.28 (s, 1H), 7.54 (s, 1H), 7.17 (d, J=2.8 Hz, 1H), 7.08 (t, J=2.8 Hz, 1H), 6.60 (s, 1H), 6.53 (s, 1H), 5.49 (d, J=6.8 Hz, 1H), 4.26 (d, J=10.4 Hz, 1H), 4.15-4.10 (m, 1H), 3.84-3.64 (m, 1H), 3.45 (s, 3H), 1.06 (s, 1H), 0.90-0.80 (m, 3H). LRMS (ESI) calcd for (C$_{18}$H$_{19}$N$_5$O$_2$+H$^+$) 338.2, found 338.1.

EXAMPLE 12

(R)-(7-(methyl(7H-pyrrolo[2,3-d]pyrimidin-4-yl)amino)-5-azaspiro[2.4]heptan-5-yl)(pyridin-3-yl)methanone

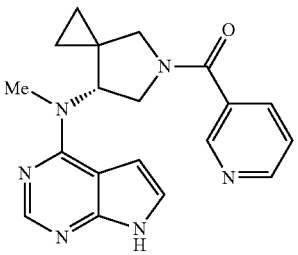 [SMILES: CN(c1ncnc2[nH]ccc12)[C@H]1CN(C(=O)c2cccnc2)CC12CC2]

$^1$H NMR (400 MHz, CDCl$_3$) δ 9.31 (s, 1H), 8.83 (s, 1H), 8.69 (s, 1H), 8.27 (d, J=25.2 Hz, 1H), 7.91 (d, J=8.0 Hz, 1H), 7.39 (s, 1H), 7.05 (s, 1H), 6.61 (d, J=21.6 Hz, 1H), 5.59-5.35 (m, 1H), 4.29-4.10 (m, 2H), 3.88-3.43 (m, 5H), 1.08-1.05 (m, 1H), 0.91-0.80 (m, 2H), 0.69 (s, 1H). LRMS (ESI) calcd for (C$_{19}$H$_{20}$N$_6$O+H$^+$) 349.2, found 349.2.

EXAMPLE 13

(R)-(7-(methyl(7H-pyrrolo[2,3-d]pyrimidin-4-yl)amino)-5-azaspiro[2.4]heptan-5-yl)(phenyl)methanone

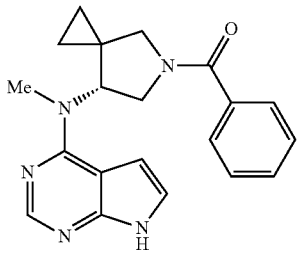

$^1$H NMR (400 MHz, CDCl$_3$) δ 9.58 (s, 1H), 8.23 (d, J=26.8 Hz, 1H), 7.56 (d, J=7.6 Hz, 2H), 7.44 (s, 3H), 7.04 (d, J=11.6 Hz, 1H), 6.59 (d, J=22.0 Hz, 1H), 5.47 (d, J=78.0 Hz, 1H), 4.27-4.11 (m, 2H), 3.84-3.62 (m, 2H), 3.45 (d, J=20.0 Hz, 3H), 1.05 (s, 1H), 0.89-0.66 (m, 3H). LRMS (ESI) calcd for (C$_{20}$H$_{21}$N$_5$O+H$^+$) 348.2, found 348.2.

EXAMPLE 14

(R)-(7-(methyl(7H-pyrrolo[2,3-d]pyrimidin-4-yl)amino)-5-azaspiro[2.4]heptan-5-yl)(pyridin-4-yl)methanone

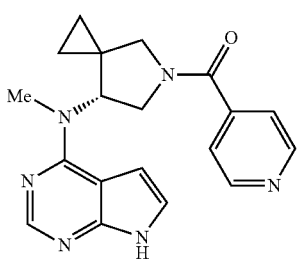 [SMILES: CN(c1ncnc2[nH]ccc12)[C@H]1CN(C(=O)c2ccncc2)CC12CC2]

$^1$H NMR (400 MHz, CDCl$_3$) δ 10.49 (s, 1H), 8.75 (dd, J=11.6, 5.6 Hz, 2H), 8.28 (d, J=26.0 Hz, 1H), 7.42-7.41 (m, 2H), 7.10 (d, J=8.8 Hz, 1H), 6.60 (d, J=17.6 Hz, 1H), 5.58-5.36 (m, 1H), 4.31-4.08 (m, 2H), 3.77-3.42 (m, 5H), 1.08-1.05 (m, 1H), 0.99-0.80 (m, 2H), 0.72-0.61 (m, 1H). LRMS (ESI) calcd for (C$_{19}$H$_{20}$N$_6$O+H$^+$) 349.2, found 349.1.

EXAMPLE 15

(R)-3-(7-(methyl(7H-pyrrolo[2,3-d]pyrimidin-4-yl)amino)-5-azaspiro[2.4]heptane-5-carbonyl)benzonitrile

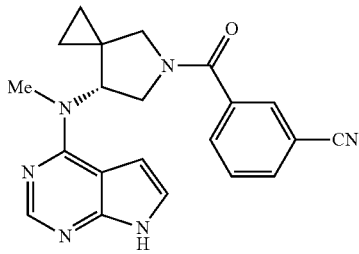 [SMILES: CN(c1ncnc2[nH]ccc12)[C@H]1CN(C(=O)c2cccc(C#N)c2)CC12CC2]

$^1$H NMR (400 MHz, CDCl$_3$) δ 9.63 (s, 1H), 8.25 (d, J=24.4 Hz, 1H), 7.86 (s, 1H), 7.82-7.73 (m, 2H), 7.58-7.54 (m, 1H), 7.07-7.02 (m, 1H), 6.61-6.57 (m, 1H), 5.60-5.35 (m, 1H), 4.29-4.09 (m, 2H), 3.84-3.63 (m, 1H), 3.44-3.42 (m, 3H), 1.27 (s, 1H), 1.09-1.04 (m, 1H), 0.94-0.79 (m, 3H). LRMS (ESI) calcd for (C$_{21}$H$_{20}$N$_6$O+H$^+$) 373.2, found 373.1.

EXAMPLE 16

(R)-4-(7-(methyl(7H-pyrrolo[2,3-d]pyrimidin-4-yl)amino)-5-azaspiro[2.4]heptane-5-carbonyl)benzonitrile

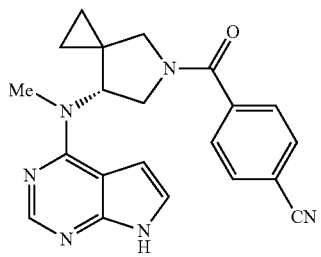 [SMILES: CN(c1ncnc2[nH]ccc12)[C@H]1CN(C(=O)c2ccc(C#N)cc2)CC12CC2]

$^1$H NMR (400 MHz, CDCl$_3$) δ 10.15 (s, 1H), 8.28 (d, J=26.8 Hz, 1H), 7.77-7.72 (m, 2H), 7.67 (d, J=8.0 Hz, 2H), 7.10 (d, J=10.4 Hz, 1H), 6.60 (d, J=20.4 Hz, 1H), 5.59 (m, 1H), 4.36-4.02 (m, 2H), 3.79-3.18 (m, 5H), 1.08-1.05 (m, 1H), 0.99-0.73 (m, 2H), 0.68 (s, 1H). LRMS (ESI) calcd for (C$_{21}$H$_{20}$N$_6$O+H$^+$) 373.2, found 373.2.

EXAMPLE 17

(R)-(7-(methyl(7H-pyrrolo[2,3-d]pyrimidin-4-yl)amino)-5-azaspiro[2.4]heptan-5-yl)(2-(trifluoromethyl)phenyl)methanone

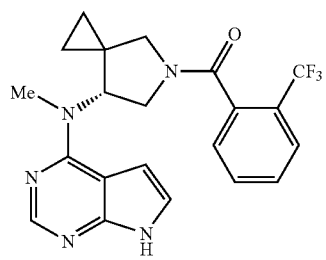 [SMILES: CN(c1ncnc2[nH]ccc12)[C@H]1CN(C(=O)c2ccccc2C(F)(F)F)CC12CC2]

$^1$H NMR (400 MHz, CDCl$_3$) δ 10.02 (s, 1H), 8.35 (d, J=32.4 Hz, 1H), 7.80-7.51 (m, 3H), 7.43 (d, J=7.2 Hz, 1H), 7.08 (d, J=9.6 Hz, 1H), 6.61 (d, J=16.8 Hz, 1H), 5.63-5.36 (m, 1H), 4.27-3.86 (m, 2H), 3.69-3.11 (m, 5H), 1.15-1.05 (m, 1H), 0.94-0.81 (m, 2H), 0.75-0.54 (m, 1H). LRMS (ESI) calcd for (C$_{21}$H$_{20}$F$_3$N$_5$O+H$^+$) 416.2, found 416.1.

EXAMPLE 18

(R)-(7-(methyl(7H-pyrrolo[2,3-d]pyrimidin-4-yl)amino)-5-azaspiro[2.4]heptan-5-yl)(3-(trifluoromethyl)phenyl)methanone

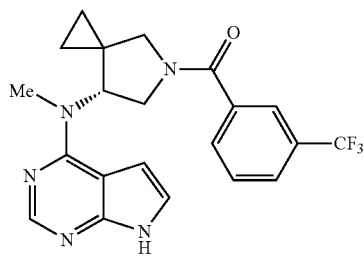 [SMILES: CN(c1ncnc2[nH]ccc12)[C@H]1CN(C(=O)c2cccc(C(F)(F)F)c2)CC12CC2]

$^1$H NMR (400 MHz, CDCl$_3$) δ 9.96 (s, 1H), 8.27 (d, J=26.0 Hz, 1H), 7.84 (s, 1H), 7.76-7.70 (m, 2H), 7.61-7.56 (m, 1H), 7.09 (d, J=10.4 Hz, 1H), 6.61 (d, J=20.4 Hz, 1H), 5.64-5.37 (m, 1H), 4.36-4.05 (m, 2H), 3.86-3.37 (m, 5H), 1.11 (d, J=13.6 Hz, 1H), 0.99-0.69 (m, 3H). LRMS (ESI) calcd for (C$_{21}$H$_{20}$F$_3$N$_5$O+H$^+$) 416.2, found 416.1.

EXAMPLE 19

(R)-3-(7-(methyl(7H-pyrrolo[2,3-d]pyrimidin-4-yl)amino)-5-azaspiro[2.4]heptan-5-yl)-3-thioxopropanenitrile

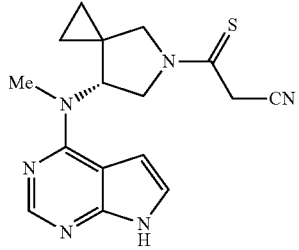 [SMILES: CN(c1ncnc2[nH]ccc12)[C@H]1CN(C(=S)CC#N)CC12CC2]

$^1$H NMR (400 MHz, CDCl$_3$) δ 12.07 (s, 1H), 8.27 (d, J=3.4 Hz, 1H), 7.20-7.08 (m, 1H), 6.57 (dd, J=5.7, 3.7 Hz, 1H), 5.45 (tt, J=186.7, 93.9 Hz, 1H), 4.42-4.25 (m, 1H), 4.20 (dd, J=131.3, 13.0 Hz, 1H), 4.01 (dd, J=162.4, 14.4 Hz, 1H), 3.98-3.85 (m, 2H), 3.90 (dd, J=211.1, 11.8 Hz, 1H), 3.44 (t, J=19.7 Hz, 3H), 1.16-1.00 (m, 1H), 0.97-0.74 (m, 3H). LRMS (ESI) calcd for (C$_{16}$H$_{18}$N$_6$S+H$^+$) 327.1, found 327.1.

EXAMPLE 20 isobutyl (R)-7-(methyl(7H-pyrrolo[2,3-d]pyrimidin-4-yl)amino)-5-azaspiro[2.4]heptane-5-carboxylate

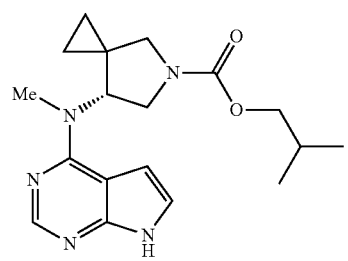

$^1$H NMR (400 MHz, CDCl$_3$) δ 10.72 (s, 1H), 8.26 (s, 1H), 7.09 (s, 1H), 6.58 (s, 1H), 5.42 (d, J=5.6 Hz, 1H), 4.06-4.02 (m, 1H), 3.93 (d, J=5.6 Hz, 2H), 3.81-3.72 (m, 2H), 3.43-3.34 (m, 4H), 2.01-1.91 (m, 1H), 1.02-0.88 (m, 7H), 0.78 (d, J=9.6 Hz, 3H). LRMS (ESI) calcd for (C$_{18}$H$_{25}$N$_5$O$_2$+H$^+$) 344.2, found 344.2.

EXAMPLE 21

(R)-N-butyl-7-(methyl(7H-pyrrolo[2,3-d]pyrimidin-4-yl)amino)-5-azaspiro[2.4]heptane-5-carboxamide

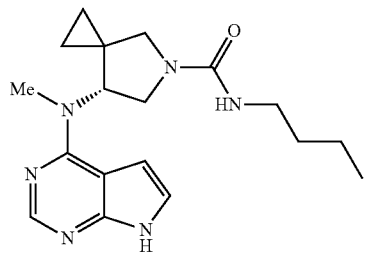 [SMILES: CCCCNC(=O)N1C[C@H](N(C)c2ncnc3[nH]ccc23)C2(CC2)C1]

$^1$H NMR (400 MHz, CDCl$_3$) δ 12.20 (s, 1H), 8.25 (s, 1H), 7.09 (d, J=3.3 Hz, 1H), 6.54 (s, 1H), 5.39 (d, J=6.4 Hz, 1H), 4.36 (s, 1H), 3.97 (dd, J=10.9, 7.4 Hz, 1H), 3.74 (d, J=9.8 Hz, 1H), 3.65 (dd, J=11.0, 1.6 Hz, 1H), 3.41 (s, 3H), 3.33 (d, J=9.9 Hz, 1H), 3.26 (dd, J=13.2, 6.4 Hz, 2H), 1.66-1.42 (m, 2H), 1.35 (dq, J=14.2, 7.3 Hz, 2H), 0.99 (d, J=9.2 Hz, 1H), 0.92 (dd, J=7.8, 6.7 Hz, 3H), 0.75 (s, 3H). LRMS (ESI) calcd for (C$_{18}$H$_{26}$N$_6$O+H$^+$) 343.2, found 343.2.

EXAMPLE 22

(R)-N-cyclohexyl-7-(methyl(7H-pyrrolo[2,3-d]pyrimidin-4-yl)amino)-5-azaspiro[2.4]heptane-5-carboxamide

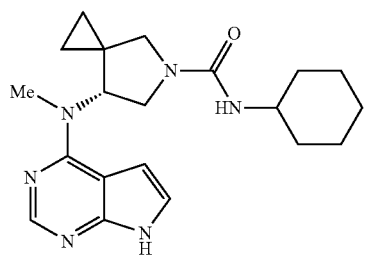 [SMILES: CN(c1ncnc2[nH]ccc12)[C@H]1CN(C(=O)NC2CCCCC2)CC12CC2]

$^1$H NMR (400 MHz, CDCl$_3$) δ 11.87 (s, 1H), 8.26 (s, 1H), 7.09 (d, J=3.5 Hz, 1H), 6.56 (d, J=2.9 Hz, 1H), 5.39 (d, J=6.4 Hz, 1H), 4.11 (d, J=7.8 Hz, 1H), 3.97 (dd, J=10.9, 7.4 Hz, 1H), 3.74 (d, J=9.9 Hz, 1H), 3.71-3.66 (m, 1H), 3.63 (dd, J=11.0, 1.7 Hz, 1H), 3.42 (s, 3H), 3.33 (d, J=9.9 Hz, 1H), 1.97 (d, J=11.5 Hz, 2H), 1.69 (dd, J=8.7, 4.1 Hz, 2H), 1.61 (d, J=12.7 Hz, 1H), 1.37 (dd, J=23.1, 11.4 Hz, 2H), 1.21-1.03 (m, 3H), 0.99 (d, J=15.2, 8.0 Hz, 1H), 0.77 (s, 3H). LRMS (ESI) calcd for (C$_{20}$H$_{28}$N$_6$O+H$^+$) 369.2, found 369.2.

EXAMPLE 23

(R)-7-(methyl(7H-pyrrolo[2,3-d]pyrimidin-4-yl)amino)-N-phenyl-5-azaspiro[2.4]heptane-5-carboxamide

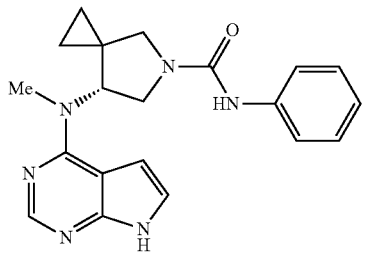 [SMILES: CN(c1ncnc2[nH]ccc12)[C@H]1CN(C(=O)Nc2ccccc2)CC12CC2]

$^1$H NMR (400 MHz, CDCl$_3$) δ 11.98 (s, 1H), 8.27 (s, 1H), 7.43 (d, J=7.7 Hz, 2H), 7.27 (dd, J=9.1, 6.7 Hz, 2H), 7.09 (d, J=3.3 Hz, 1H), 7.02 (t, J=7.4 Hz, 1H), 6.55 (d, J=3.0 Hz, 1H), 6.44 (s, 1H), 5.42 (d, J=6.5 Hz, 1H), 4.09 (dd, J=10.9, 7.5 Hz, 1H), 3.86 (d, J=10.0 Hz, 1H), 3.82-3.73 (m, 1H), 3.45 (s, 1H), 3.43 (s, 3H), 1.08-0.99 (m, 1H), 0.78 (s, 3H). LRMS (ESI) calcd for (C$_{20}$H$_{22}$N$_6$O+H$^+$) 363.2, found 363.2.

EXAMPLE 24

(R)-N-(4-fluorophenyl)-7-(methyl(7H-pyrrolo[2,3-d]pyrimidin-4-yl)amino)-5-azaspiro[2.4]heptane-5-carboxamide

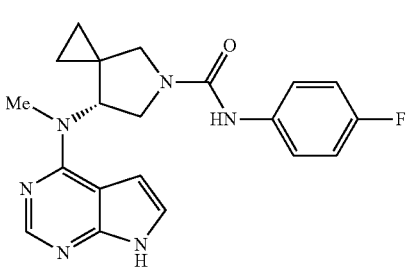 [SMILES: CN(c1ncnc2[nH]ccc12)[C@H]1CN(C(=O)Nc2ccc(F)cc2)CC12CC2]

$^1$H NMR (400 MHz, CDCl$_3$) δ 10.16 (s, 1H), 8.27 (s, 1H), 7.40-7.37 (m, 2H), 7.10-7.09 (m, 1H), 7.03-6.99 (m, 2H), 6.61 (s, 1H), 6.19 (s, 1H), 5.46 (d, J=5.6 Hz, 1H), 4.15 (dd, J=10.8, 7.2 Hz, 1H), 3.91 (d, J=10.0 Hz, 1H), 3.81 (dd, J=11.2, 2.0 Hz, 1H), 3.48-3.46 (m, 4H), 1.11-1.02 (m, 1H), 0.90-0.84 (m, 3H). LRMS (ESI) calcd for (C$_{20}$H$_{21}$FN$_6$O+H$^+$) 381.2, found 381.2.

EXAMPLE 25

(R)-N-(2,4-dichlorophenyl)-7-(methyl(7H-pyrrolo[2,3-d]pyrimidin-4-yl)amino)-5-azaspiro[2.4]heptane-5-carboxamide

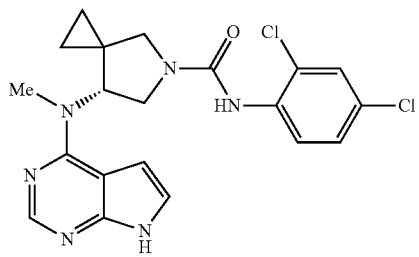 [SMILES: CN(c1ncnc2[nH]ccc12)[C@H]1CN(C(=O)Nc2ccc(Cl)cc2Cl)CC12CC2]

$^1$H NMR (400 MHz, CDCl$_3$) δ 10.08 (s, 1H), 8.32 (d, J=9.2 Hz, 1H), 8.27 (s, 1H), 7.37 (d, J=2.4 Hz, 1H), 7.27-7.24 (m, 1H), 7.10 (t, J=2.8 Hz, 1H), 6.83 (s, 1H), 6.61 (s, 1H), 5.53 (d, J=6.4 Hz, 1H), 4.20 (dd, J=11.2, 7.6 Hz, 1H), 3.92 (d, J=9.6 Hz, 1H), 3.85 (d, J=10.0 Hz, 1H), 3.50 (m, 4H), 1.11 (d, J=11.2 Hz, 1H), 0.90-0.85 (m, 3H). LRMS (ESI) calcd for (C$_{20}$H$_{20}$Cl$_2$N$_6$O+H$^+$) 431.1, found 431.1.

EXAMPLE 26

(R)-N-(3,4-dichlorophenyl)-7-(methyl(7H-pyrrolo[2,3-d]pyrimidin-4-yl)amino)-5-azaspiro[2.4]heptane-5-carboxamide

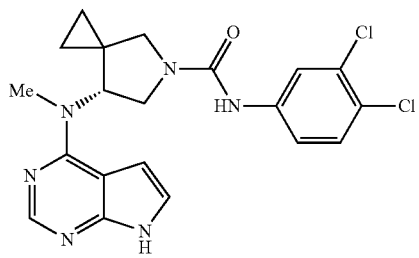 [SMILES: CN(c1ncnc2[nH]ccc12)[C@H]1CN(C(=O)Nc2ccc(Cl)c(Cl)c2)CC12CC2]

$^1$H NMR (400 MHz, CDCl$_3$) δ 9.96 (s, 1H), 8.27 (s, 1H), 7.70 (d, J=2.4 Hz, 1H), 7.35 (d, J=8.8 Hz, 1H), 7.27 (d, J=2.8 Hz, 1H), 7.10-7.09 (m, 1H), 6.61 (d, J=2.0 Hz, 1H), 6.26 (s, 1H), 5.45 (d, J=5.6 Hz, 1H), 4.14 (dd, J=10.8, 7.2 Hz, 1H), 3.90 (d, J=10.4 Hz, 1H), 3.80 (d, J=11.2 Hz, 1H), 3.48 (s, 3H), 3.46 (s, 1H), 1.09-1.06 (m, 1H), 0.90-0.85 (m, 3H). LRMS (ESI) calcd for (C$_{20}$H$_{20}$Cl$_2$N$_6$O+H$^+$) 431.1, found 431.1.

EXAMPLE 27

(R)-N-(2,5-dichlorophenyl)-7-(methyl(7H-pyrrolo[2,3-d]pyrimidin-4-yl)amino)-5-azaspiro[2.4]heptane-5-carboxamide

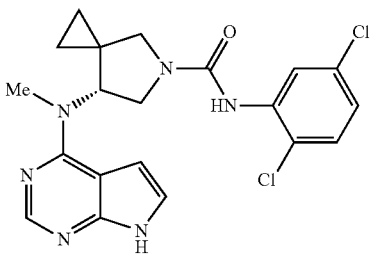 [SMILES: CN(c1ncnc2[nH]ccc12)[C@H]1CN(C(=O)Nc2cc(Cl)ccc2Cl)CC12CC2]

$^1$H NMR (400 MHz, CDCl$_3$) δ 9.92 (s, 1H), 8.47 (d, J=2.4 Hz, 1H), 8.28 (s, 1H), 7.27 (s, 1H), 7.09 (t, J=2.0 Hz, 1H), 6.97 (dd, J=8.4, 2.4 Hz, 1H), 6.89 (s, 1H), 6.62 (d, J=1.6 Hz, 1H), 5.55 (d, J=6.4 Hz, 1H), 4.19 (dd, J=11.2, 7.6 Hz, 1H), 3.92 (d, J=10.0 Hz, 1H), 3.85 (d, J=11.2 Hz, 1H), 3.51 (s, 1H), 3.49 (s, 3H), 1.10 (d, J=11.2 Hz, 1H), 0.94-0.85 (m, 3H). LRMS (ESI) calcd for (C$_{20}$H$_{20}$Cl$_2$N$_6$O+H$^+$) 431.1, found 431.1.

EXAMPLE 28

(R)-N-(2,3-dichlorophenyl)-7-(methyl(7H-pyrrolo[2,3-d]pyrimidin-4-yl)amino)-5-azaspiro[2.4]heptane-5-carboxamide

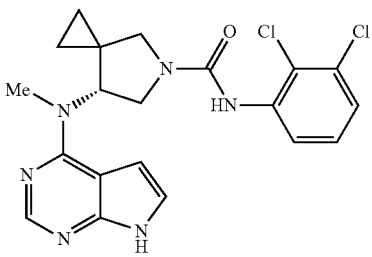 [SMILES: CN(c1ncnc2[nH]ccc12)[C@H]1CN(C(=O)Nc2cccc(Cl)c2Cl)CC12CC2]

$^1$H NMR (400 MHz, CDCl$_3$) δ 12.03 (s, 1H), 8.39-8.21 (m, 2H), 7.19 (t, J=8.2 Hz, 1H), 7.13 (dd, J=3.9, 3.3 Hz, 2H), 6.97 (s, 1H), 6.58 (d, J=3.4 Hz, 1H), 5.55 (d, J=6.3 Hz, 1H), 4.17 (dd, J=11.2, 7.5 Hz, 1H), 3.88 (dd, J=22.4, 10.5 Hz, 2H), 3.50 (s, 1H), 3.47 (s, 3H), 1.14-1.01 (m, 1H), 0.84 (s, 3H). LRMS (ESI) calcd for (C$_{20}$H$_{20}$Cl$_2$N$_6$O+H$^+$) 431.1, found 431.0.

EXAMPLE 29

(R)-N-(3-chloro-4-methylphenyl)-7-(methyl(7H-pyrrolo[2,3-d]pyrimidin-4-yl)amino)-5-azaspiro[2.4]heptane-5-carboxamide

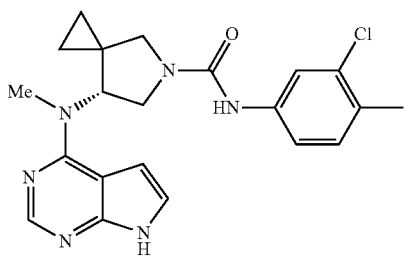 [SMILES: Cc1ccc(NC(=O)N2C[C@H](N(C)c3ncnc4[nH]ccc34)C3(CC3)C2)cc1Cl]

$^1$H NMR (400 MHz, CDCl$_3$) δ 11.92 (s, 1H), 8.25 (s, 1H), 7.49 (d, J=2.0 Hz, 1H), 7.19 (dd, J=8.3, 2.1 Hz, 1H), 7.08 (s, 1H), 7.06 (d, J=5.2 Hz, 1H), 6.56 (s, 1H), 6.53 (d, J=3.4 Hz, 1H), 5.39 (d, J=6.2 Hz, 1H), 4.06 (dd, J=11.1, 7.4 Hz, 1H), 3.82 (d, J=10.1 Hz, 1H), 3.77 (dd, J=11.1, 1.5 Hz, 1H), 3.46-3.35 (m, 4H), 2.28 (s, 3H), 1.05-0.96 (m, 1H), 0.82-0.71 (m, 3H). LRMS (ESI) calcd for (C$_{21}$H$_{23}$ClN$_6$O+H$^+$) 411.2, found 411.1.

EXAMPLE 30

(R)-N-([1,1'-biphenyl]-2-yl)-7-(methyl(7H-pyrrolo[2,3-d]pyrimidin-4-yl)amino)-5-azaspiro[2.4]heptane-5-carboxamide

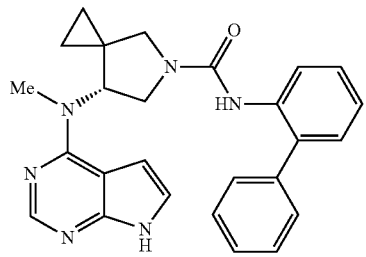 [SMILES: CN(c1ncnc2[nH]ccc12)[C@H]1CN(C(=O)Nc2ccccc2-c2ccccc2)CC12CC2]

$^1$H NMR (400 MHz, CDCl$_3$) δ 11.27 (s, 1H), 8.24 (s, 1H), 8.20 (d, J=8.3 Hz, 1H), 7.51-7.30 (m, 6H), 7.21 (d, J=7.2 Hz, 1H), 7.10 (dd, J=9.2, 5.5 Hz, 2H), 6.55 (d, J=2.9 Hz, 1H), 6.38 (s, 1H), 5.34 (d, J=6.4 Hz, 1H), 3.82 (dd, J=10.9, 7.5 Hz, 1H), 3.64 (d, J=10.0 Hz, 1H), 3.48 (d, J=10.1 Hz, 1H), 3.38 (s, 3H), 3.20 (d, J=9.9 Hz, 1H), 1.04-0.95 (m, 1H), 0.78-0.59 (m, 3H). LRMS (ESI) calcd for (C$_{26}$H$_{26}$N$_6$O+H$^+$) 439.2, found 439.2.

EXAMPLE 31

(R)-N-(3,5-bis(trifluoromethyl)phenyl)-7-(methyl(7H-pyrrolo[2,3-d]pyrimidin-4-yl)amino)-5-azaspiro[2.4]heptane-5-carbothioamide

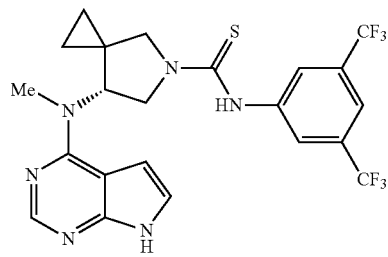 [SMILES: CN(c1ncnc2[nH]ccc12)[C@H]1CN(C(=S)Nc2cc(C(F)(F)F)cc(C(F)(F)F)c2)CC12CC2]

$^1$H NMR (400 MHz, CDCl$_3$) δ 11.64 (s, 1H), 8.25 (s, 1H), 7.96 (s, 2H), 7.65 (s, 1H), 7.41 (s, 1H), 7.10 (d, J=3.4 Hz, 1H), 6.57 (d, J=3.4 Hz, 1H), 5.44 (d, J=5.0 Hz, 1H), 4.31 (s, 1H), 4.17 (s, 1H), 4.08 (s, 1H), 3.75 (s, 1H), 3.46 (s, 3H), 1.05 (d, J=5.7 Hz, 1H), 0.87 (d, J=8.1 Hz, 3H). LRMS (ESI) calcd for (C$_{22}$H$_{20}$F$_6$N$_6$S+H$^+$) 515.1, found 515.1.

EXAMPLE 32

(R)-N-methyl-N-(5-((trifluoromethyl)sulfonyl)-5-azaspiro[2.4]heptan-7-yl)-7H-pyrrolo[2,3-d]pyrimidin-4-amine

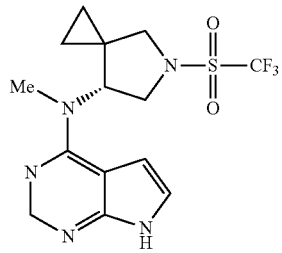 [SMILES: CN(C1=c2cc[nH]c2=NCN1)[C@H]1CN(S(=O)(=O)C(F)(F)F)CC12CC2]

$^1$H NMR (400 MHz, CDCl$_3$) δ 10.34 (s, 1H), 8.26 (s, 1H), 7.12 (s, 1H), 6.61 (s, 1H), 5.56 (dd, J=7.6, 3.2 Hz, 1H), 4.19 (dd, J=11.6, 7.6 Hz, 1H), 3.93-3.85 (m, 2H), 3.53-3.49 (m, 4H), 1.12-1.05 (m, 1H), 0.89-0.83 (m, 3H). LRMS (ESI) calcd for (C$_{14}$H$_{16}$F$_3$N$_5$O$_2$S+H$^+$) 376.1, found 376.1.

EXAMPLE 33

(R)-N-(5-(ethylsulfonyl)-5-azaspiro[2.4]heptan-7-yl)-N-methyl-7H-pyrrolo[2,3-d]pyrimidin-4-amine

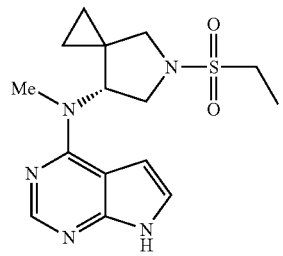 [SMILES: CCS(=O)(=O)N1C[C@H](N(C)c2ncnc3[nH]ccc23)C2(CC2)C1]

¹H NMR (400 MHz, CDCl₃) δ 10.53 (s, 1H), 8.25 (s, 1H), 7.10-7.09 (m, 1H), 6.61 (s, 1H), 5.58 (dd, J=5.3, 2.8 Hz, 1H), 3.96 (dd, J=11.2, 7.6 Hz, 1H), 3.72-3.68 (m, 2H), 3.50 (s, 3H), 3.37 (d, J=9.6 Hz, 1H), 3.12 (q, J=7.0 Hz, 2H), 1.47 (t, J=7.4 Hz, 3H), 1.10-1.03 (m, 1H), 0.86-0.72 (m, 3H). LRMS (ESI) calcd for ($C_{15}H_{21}N_5O_2S+H^+$) 336.2, found 336.1.

EXAMPLE 34

(R)-N-(5-(isopropylsulfonyl)-5-azaspiro[2.4]heptan-7-yl)-N-methyl-7H-pyrrolo[2,3-d]pyrimidin-4-amine

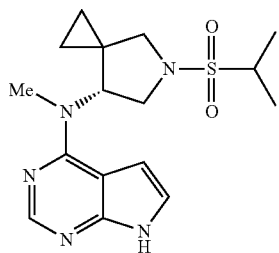 [SMILES: CC(C)S(=O)(=O)N1C[C@H](N(C)c2ncnc3[nH]ccc23)C2(CC2)C1]

¹H NMR (400 MHz, CDCl₃) δ 9.60 (s, 1H), 8.25 (s, 1H), 7.07 (s, 1H), 6.60 (s, 1H), 5.53 (d, J=4.4 Hz, 1H), 4.01 (dd, J=11.2, 7.6 Hz, 1H), 3.77-3.71 (m, 2H), 3.49 (s, 3H), 3.40 (d, J=9.6 Hz, 1H), 3.33-3.27 (m, 1H), 1.44 (d, J=6.4 Hz, 6H), 1.11-1.01 (m, 1H), 0.90-0.75 (m, 3H). LRMS (ESI) calcd for ($C_{16}H_{23}N_5O_2S+H^+$) 350.2, found 350.2.

EXAMPLE 35

(R)-N-methyl-N-(5-(propylsulfonyl)-5-azaspiro[2.4]heptan-7-yl)-7H-pyrrolo[2,3-d]pyrimidin-4-amine

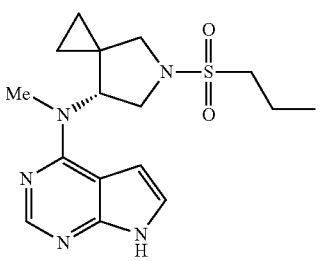 [SMILES: CCCS(=O)(=O)N1C[C@H](N(C)c2ncnc3[nH]ccc23)C2(CC2)C1]

¹H NMR (400 MHz, CDCl₃) δ 10.38 (s, 1H), 8.25 (s, 1H), 7.09 (s, 1H), 6.60 (s, 1H), 5.82-5.55 (m, 1H), 3.92 (dd, J=10.8, 7.6 Hz, 1H), 3.70-3.67 (m, 2H), 3.50 (s, 3H), 3.35 (d, J=10.0 Hz, 1H), 3.05-3.01 (m, 2H), 2.06-1.90 (m, 2H), 1.13 (t, J=7.6 Hz, 3H), 1.07-1.02 (m, 1H), 0.86-0.71 (m, 3H). LRMS (ESI) calcd for ($C_{16}H_{23}N_5O_2S+H^+$) 350.2, found 350.1.

EXAMPLE 36

(R)-N-methyl-N-(5-(phenylsulfonyl)-5-azaspiro[2.4]heptan-7-yl)-7H-pyrrolo[2,3-d]pyrimidin-4-amine

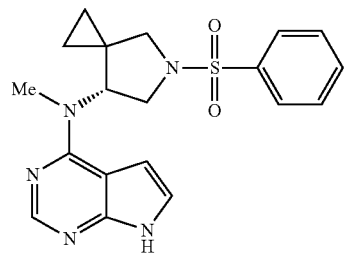 [SMILES: CN(c1ncnc2[nH]ccc12)[C@H]1CN(S(=O)(=O)c2ccccc2)CC12CC2]

¹H NMR (400 MHz, CDCl₃) δ 10.68 (s, 1H), 8.18 (s, 1H), 7.87 (d, J=7.2 Hz, 2H), 7.74-7.57 (m, 3H), 7.05 (s, 1H), 6.56 (s, 1H), 5.45 (t, J=5.0 Hz, 1H), 3.68-3.59 (m, 2H), 3.57 (d, J=5.6 Hz, 1H), 3.36 (s, 3H), 3.10 (d, J=9.6 Hz, 1H), 0.93-0.87 (m, 1H), 0.84-0.72 (m, 1H), 0.67-0.59 (m, 2H). LRMS (ESI) calcd for ($C_{19}H_{21}N_5O_2S+H^+$) 384.2, found 384.1.

EXAMPLE 37

(R)-N-(5-((2-fluorophenyl)sulfonyl)-5-azaspiro[2.4]heptan-7-yl)-N-methyl-7H-pyrrolo[2,3-d]pyrimidin-4-amine

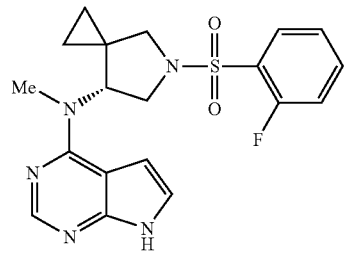 [SMILES: CN(c1ncnc2[nH]ccc12)[C@H]1CN(S(=O)(=O)c2ccccc2F)CC12CC2]

¹H NMR (400 MHz, CDCl₃) δ 9.52 (s, 1H), 8.19 (s, 1H), 7.95-7.91 (m, 1H), 7.66-7.61 (m, 1H), 7.34-7.25 (m, 2H), 7.25 (s, 1H), 6.57 (s, 1H), 5.49-5.46 (m, 1H), 3.85 (dd, J=11.2, 7.6 Hz, 1H), 3.72-3.69 (m, 2H), 3.43 (s, 3H), 3.30 (d, J=9.6 Hz, 1H), 0.98-0.88 (m, 1H), 0.82-0.77 (m, 1H), 0.74-0.65 (m, 2H). LRMS (ESI) calcd for ($C_{19}H_{20}FN_5O_2S+H^+$) 402.1, found 402.1.

EXAMPLE 38

(R)-N-(5-((3-fluorophenyl)sulfonyl)-5-azaspiro[2.4]heptan-7-yl)-N-methyl-7H-pyrrolo[2,3-d]pyrimidin-4-amine

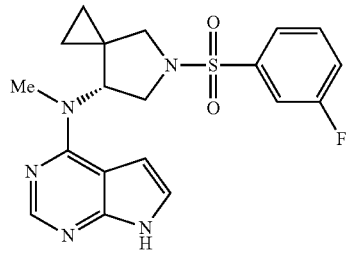 [SMILES: CN(c1ncnc2[nH]ccc12)[C@H]1CN(S(=O)(=O)c2cccc(F)c2)CC12CC2]

$^1$H NMR (400 MHz, CDCl$_3$) δ 9.30 (s, 1H), 8.18 (s, 1H), 7.67-7.54 (m, 3H), 7.40-7.33 (m, 1H), 7.06-7.02 (m, 1H), 6.57-6.56 (m, 1H), 5.46-5.44 (m, 1H), 3.65-3.62 (m, 2H), 3.59 (d, J=9.6 Hz, 1H), 3.38 (s, 3H), 3.12 (d, J=9.6 Hz, 1H), 0.96-0.91 (m, 1H), 0.80-0.74 (m, 1H), 0.69-0.68 (m, 2H). LRMS (ESI) calcd for (C$_{19}$H$_{20}$FN$_5$O$_2$S+H$^+$) 402.1, found 402.1.

EXAMPLE 39

(R)-N-(5-((4-fluorophenyl)sulfonyl)-5-azaspiro[2.4]heptan-7-yl)-N-methyl-7H-pyrrolo[2,3-d]pyrimidin-4-amine

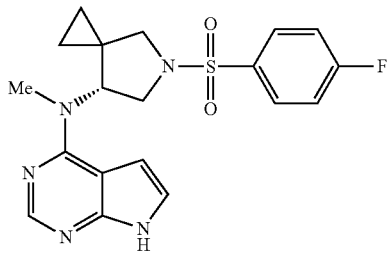 [SMILES: CN(c1ncnc2[nH]ccc12)[C@H]1CN(S(=O)(=O)c2ccc(F)cc2)CC12CC2]

$^1$H NMR (400 MHz, CDCl$_3$) δ 9.62 (s, 1H), 8.18 (s, 1H), 7.94-7.85 (m, 2H), 7.27-7.24 (m, 2H), 7.06-6.99 (m, 1H), 6.57-6.55 (m, 1H), 5.46 (dd, J=6.4, 1.6 Hz, 1H), 3.71-3.53 (m, 3H), 3.38 (s, 3H), 3.09 (d, J=9.6 Hz, 1H), 0.95-0.88 (m, 1H), 0.82-0.74 (m, 1H), 0.69-0.60 (m, 2H). LRMS (ESI) calcd for (C$_{19}$H$_{20}$FN$_5$O$_2$S+H$^+$) 402.1, found 402.1.

EXAMPLE 40

(R)-2-((7-(methyl(7H-pyrrolo[2,3-d]pyrimidin-4-yl)amino)-5-azaspiro[2.4]heptan-5-yl)sulfonyl)benzonitrile

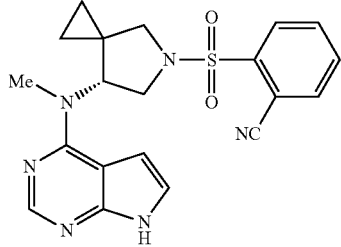 [SMILES: CN(c1ncnc2[nH]ccc12)[C@H]1CN(S(=O)(=O)c2ccccc2C#N)CC12CC2]

$^1$H NMR (400 MHz, CDCl$_3$) δ 10.10 (s, 1H), 8.19 (s, 1H), 8.13 (dd, J=8.0, 1.6 Hz, 1H), 7.95 (dd, J=7.2, 1.2 Hz, 1H), 7.81-7.73 (m, 2H), 7.08-7.02 (m, 1H), 6.58-6.56 (m, 1H), 5.52 (dd, J=7.6, 6.8 Hz, 1H), 3.85-3.74 (m, 2H), 3.72 (dd, J=10.8, 3.0 Hz, 1H), 3.43 (s, 3H), 3.41 (d, J=10.0 Hz, 1H), 1.06-0.94 (m, 1H), 0.88-0.69 (m, 3H). LRMS (ESI) calcd for (C$_{20}$H$_{20}$N$_6$O$_2$S+H$^+$) 409.1, found 409.1.

EXAMPLE 41

(R)-3-((7-(methyl(7H-pyrrolo[2,3-d]pyrimidin-4-yl)amino)-5-azaspiro[2.4]heptan-5-yl)sulfonyl)benzonitrile

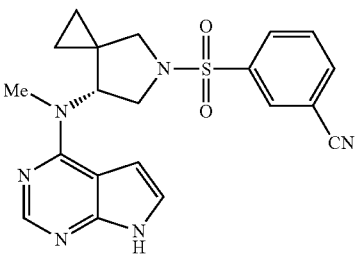 [SMILES: CN(c1ncnc2[nH]ccc12)[C@H]1CN(S(=O)(=O)c2cccc(C#N)c2)CC12CC2]

$^1$H NMR (400 MHz, CDCl$_3$) δ 10.12 (s, 1H), 8.18 (s, 1H), 8.17 (s, 1H), 8.09-8.07 (m, 1H), 7.95-7.93 (m, 1H), 7.75 (t, J=8.0 Hz, 1H), 7.08-7.02 (m, 1H), 6.56-6.55 (m, 1H), 5.44-5.32 (m, 1H), 3.69-3.61 (m, 3H), 3.39 (s, 3H), 3.13 (d, J=9.6 Hz, 1H), 0.98-0.88 (m, 1H), 0.84-0.77 (m, 1H), 0.73-0.63 (m, 2H). LRMS (ESI) calcd for (C$_{20}$H$_{20}$N$_6$O$_2$S+H$^+$) 409.1, found 409.1.

EXAMPLE 42

(R)-4-((7-(methyl(7H-pyrrolo[2,3-d]pyrimidin-4-yl)amino)-5-azaspiro[2.4]heptan-5-yl)sulfonyl)benzonitrile

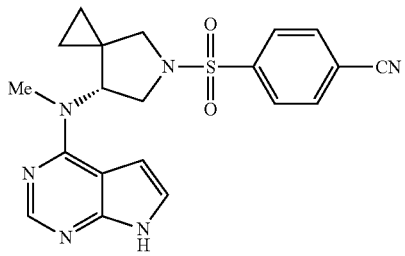

¹H NMR (400 MHz, CDCl₃) δ 9.99 (s, 1H), 8.19 (s, 1H), 7.97 (d, J=8.0 Hz, 2H), 7.87 (d, J=8.4 Hz, 2H), 7.08 (s, 1H), 6.55 (s, 1H), 5.39-5.37 (m, 1H), 3.68-3.65 (m, 2H), 3.62 (d, J=9.6 Hz, 1H), 3.36 (s, 3H), 3.13 (d, J=9.6 Hz, 1H), 0.99-0.91 (m, 1H), 0.85-0.74 (m, 1H), 0.72-0.62 (m, 2H). LRMS (ESI) calcd for ($C_{20}H_{20}N_6O_2S+H^+$) 409.1, found 409.1.

EXAMPLE 43

(R)-N-methyl-N-(5-((2-nitrophenyl)sulfonyl)-5-azaspiro[2.4]heptan-7-yl)-7H-pyrrolo[2,3-d]pyrimidin-4-amine

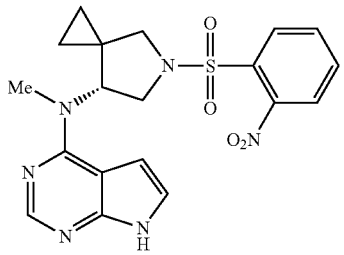 [SMILES: CN(c1ncnc2[nH]ccc12)[C@H]1CN(S(=O)(=O)c2ccccc2[N+](=O)[O-])CC12CC2]

¹H NMR (400 MHz, CDCl₃) δ 9.67 (s, 1H), 8.22 (s, 1H), 8.05 (dd, J=7.6, 1.6 Hz, 1H), 7.78-7.66 (m, 3H), 7.07 (t, J=2.4 Hz, 1H), 6.58 (t, J=2.0 Hz, 1H), 5.52 (dd, J=7.6, 2.4 Hz, 1H), 3.96 (dd, J=10.8, 7.6 Hz, 1H), 3.80-3.75 (m, 2H), 3.43 (s, 3H), 3.41 (s, 1H), 1.03-0.99 (m, 1H), 0.92-0.72 (m, 3H). LRMS (ESI) calcd for ($C_{19}H_{20}N_6O_4S+H^+$) 429.1, found 429.1.

EXAMPLE 44

(R)-N-methyl-N-(5-((3-nitrophenyl)sulfonyl)-5-azaspiro[2.4]heptan-7-yl)-7H-pyrrolo[2,3-d]pyrimidin-4-amine

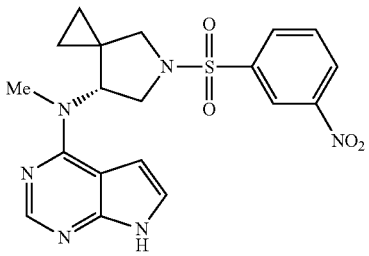 [SMILES: CN(c1ncnc2[nH]ccc12)[C@H]1CN(S(=O)(=O)c2cccc([N+](=O)[O-])c2)CC12CC2]

¹H NMR (400 MHz, CDCl₃) δ 9.88 (s, 1H), 8.22 (s, 1H), 8.05 (dd, J=7.6, 1.6 Hz, 1H), 7.78-7.66 (m, 3H), 7.07 (t, J=2.4 Hz, 1H), 6.58 (t, J=2.0 Hz, 1H), 5.52 (dd, J=7.6, 2.4 Hz, 1H), 3.96 (dd, J=10.8, 7.6 Hz, 1H), 3.80-3.75 (m, 2H), 3.43 (s, 3H), 3.41 (s, 1H), 1.03-0.99 (m, 1H), 0.92-0.72 (m, 3H). LRMS (ESI) calcd for ($C_{19}H_{20}N_6O_4S+H^+$) 429.1, found 429.1.

EXAMPLE 45

(R)-N-methyl-N-(5-((4-nitrophenyl)sulfonyl)-5-azaspiro[2.4]heptan-7-yl)-7H-pyrrolo[2,3-d]pyrimidin-4-amine

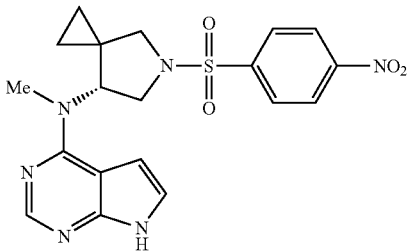 [SMILES: CN(c1ncnc2[nH]ccc12)[C@H]1CN(S(=O)(=O)c2ccc([N+](=O)[O-])cc2)CC12CC2]

¹H NMR (400 MHz, CDCl₃) δ 9.76 (s, 1H), 8.41 (d, J=8.4 Hz, 2H), 8.19 (s, 1H), 8.04 (d, J=8.8 Hz, 2H), 7.07 (t, J=2.4 Hz, 1H), 6.53 (t, J=1.6 Hz, 1H), 5.39-5.36 (m, 1H), 3.72-3.67 (m, 2H), 3.64 (d, J=9.6 Hz, 1H), 3.38 (s, 3H), 3.14 (d, J=9.6 Hz, 1H), 0.96-0.89 (m, 1H), 0.88-0.79 (m, 1H), 0.75-0.63 (m, 2H). LRMS (ESI) calcd for ($C_{19}H_{20}N_6O_4S+H^+$) 429.1, found 429.1.

EXAMPLE 46

(R)-N-methyl-N-(5-(m-tolylsulfonyl)-5-azaspiro[2.4]heptan-7-yl)-7H-pyrrolo[2,3-d]pyrimidin-4-amine

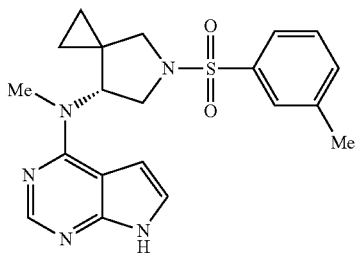 [SMILES: Cc1cccc(S(=O)(=O)N2C[C@H](N(C)c3ncnc4[nH]ccc34)C3(CC3)C2)c1]

$^1$H NMR (400 MHz, CDCl$_3$) δ 10.10 (s, 1H), 8.19 (s, 1H), 7.66 (s, 2H), 7.47-7.46 (m, 2H), 7.06 (s, 1H), 6.55 (s, 1H), 5.45-5.43 (m, 1H), 3.61-3.52 (m, 3H), 3.37 (s, 3H), 3.10-3.07 (d, J=9.6 Hz, 1H), 2.46 (s, 3H), 0.93-0.88 (m, 1H), 0.79-0.73 (m, 1H), 0.67-0.59 (m, 2H). LRMS (ESI) calcd for (C$_{20}$H$_{23}$N$_5$O$_2$S+H$^+$) 398.2, found 398.1.

EXAMPLE 47

(R)-N-(5-((4-methoxyphenyl)sulfonyl)-5-azaspiro[2.4]heptan-7-yl)-N-methyl-7H-pyrrolo[2,3-d]pyrimidin-4-amine

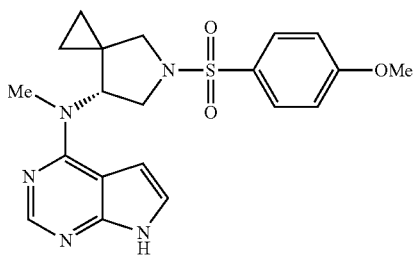 [SMILES: COc1ccc(S(=O)(=O)N2C[C@H](N(C)c3ncnc4[nH]ccc34)C3(CC3)C2)cc1]

$^1$H NMR (400 MHz, CDCl$_3$) δ 9.82 (s, 1H), 8.24 (s, 1H), 7.81 (d, J=8.0 Hz, 2H), 7.05 (d, J=8.0 Hz, 3H), 6.61 (s, 1H), 5.46 (s, 1H), 3.92 (s, 3H), 3.61-3.55 (m, 2H), 3.53 (m, 1H), 3.38 (s, 3H), 3.07 (d, J=9.6 Hz, 1H), 0.94-0.90 (m, 1H), 0.82-0.72 (m, 1H), 0.66-0.59 (m, 2H). LRMS (ESI) calcd for (C$_{20}$H$_{23}$N$_5$O$_3$S+H$^+$) 414.2, found 414.1.

EXAMPLE 48

(R)-N-methyl-N-(5-((4-(trifluoromethyl)phenyl)sulfonyl)-5-azaspiro[2.4]heptan-7-yl)-7H-pyrrolo[2,3-d]pyrimidin-4-amine

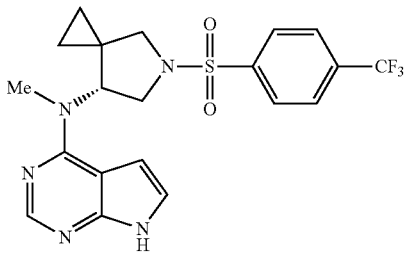 [SMILES: CN(c1ncnc2[nH]ccc12)[C@H]1CN(S(=O)(=O)c2ccc(C(F)(F)F)cc2)CC12CC2]

$^1$H NMR (400 MHz, CDCl$_3$) δ 10.10 (s, 1H), 8.18 (s, 1H), 8.00 (d, J=8.0 Hz, 2H), 7.80 (d, J=8.8 Hz, 2H), 7.08 (s, 1H), 6.54 (s, 1H), 5.43-5.32 (m, 1H), 3.69-3.58 (m, 3H), 3.37 (s, 3H), 3.13 (d, J=9.60 Hz, 1H), 0.97-0.88 (m, 1H), 0.81-0.75 (m, 1H), 0.71-0.62 (m, 2H). LRMS (ESI) calcd for (C$_{20}$H$_{20}$F$_3$N$_5$O$_2$S+H$^+$) 452.1, found 452.1.

EXAMPLE 49

(R)-N-methyl-N-(5-(naphthalen-2-ylsulfonyl)-5-azaspiro[2.4]heptan-7-yl)-7H-pyrrolo[2,3-d]pyrimidin-4-amine

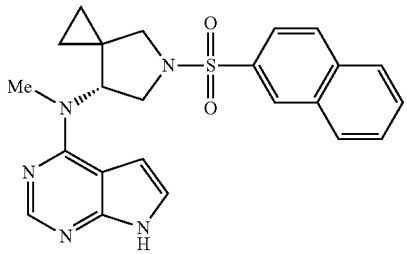 [SMILES: CN(c1ncnc2[nH]ccc12)[C@H]1CN(S(=O)(=O)c2ccc3ccccc3c2)CC12CC2]

$^1$H NMR (400 MHz, CDCl$_3$) δ 9.76 (s, 1H), 8.43 (s, 1H), 8.16 (s, 1H), 8.03-7.96 (m, 3H), 7.87 (dd, J=8.8, 5.6 Hz, 1H), 7.72-7.59 (m, 2H), 7.03 (s, 1H), 6.57 (s, 1H), 5.54-5.41 (m, 1H), 3.75-3.63 (m, 2H), 3.62 (d, J=9.6 Hz, 1H), 3.36 (s, 3H), 3.17 (d, J=9.6 Hz, 1H), 0.90-0.84 (m, 1H), 0.78-0.72 (m, 1H), 0.68-0.57 (m, 2H). LRMS (ESI) calcd for (C$_{23}$H$_{23}$N$_5$O$_2$S+H$^+$) 434.2, found 434.1.

EXAMPLE 50

(R)-N-methyl-N-(5-(piperidin-1-ylsulfonyl)-5-azaspiro[2.4]heptan-7-yl)-7H-pyrrolo[2,3-d]pyrimidin-4-amine

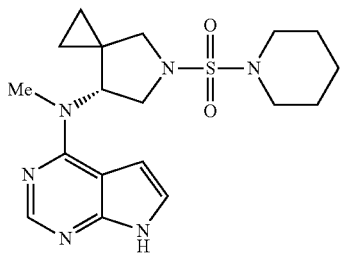 [SMILES: CN(c1ncnc2[nH]ccc12)[C@H]1CN(S(=O)(=O)N2CCCCC2)CC12CC2]

$^1$H NMR (400 MHz, CDCl$_3$) δ 9.81 (s, 1H), 8.24 (s, 1H), 7.07-7.00 (m, 1H), 6.60-6.59 (m, 1H), 5.52 (d, J=5.2 Hz, 1H), 3.87 (dd, J=10.8, 7.6 Hz, 1H), 3.57-3.54 (m, 2H), 3.49 (s, 3H), 3.31-3.28 (m, 4H), 1.81-1.58 (m, 7H), 1.04-1.01 (m, 1H), 0.82-0.74 (m, 2H), 0.71-0.68 (m, 1H). LRMS (ESI) calcd for (C$_{18}$H$_{26}$N$_6$O$_2$S+H$^+$) 391.2, found 391.1.

EXAMPLE 51

(R)-N-methyl-N-(5-(morpholinosulfonyl)-5-azaspiro[2.4]heptan-7-yl)-7H-pyrrolo[2,3-d]pyrimidin-4-amine

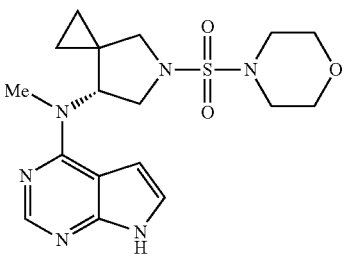 [SMILES: CN(c1ncnc2[nH]ccc12)[C@H]1CN(S(=O)(=O)N2CCOCC2)CC12CC2]

$^1$H NMR (400 MHz, CDCl$_3$) δ 9.65 (s, 1H), 8.25 (s, 1H), 7.08-7.07 (m, 1H), 6.65-6.59 (m, 1H), 5.58 (dd, J=7.6, 2.8 Hz, 1H), 3.93 (dd, J=10.8, 7.6 Hz, 1H), 3.78 (t, J=4.8 Hz, 4H), 3.65-3.59 (m, 2H), 3.48 (s, 3H), 3.34-3.30 (m, 5H), 1.10-1.02 (m, 1H), 0.83-0.72 (m, 3H). LRMS (ESI) calcd for (C$_{17}$H$_{24}$N$_6$O$_3$S+H$^+$) 393.2, found 393.1.

EXAMPLE 52

1-(7-(methyl(7H-pyrrolo[2,3-d]pyrimidin-4-yl)amino)-5-azaspiro[2.4]heptan-5-yl)propan-1-one

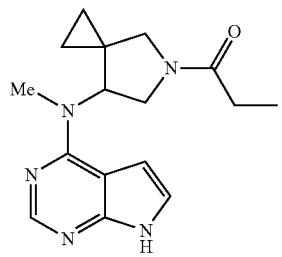 [SMILES: CCC(=O)N1CC(N(C)c2ncnc3[nH]ccc23)C2(CC2)C1]

$^1$H NMR (400 MHz, CDCl$_3$) δ 10.02 (s, 1H), 8.32-8.16 (m, 1H), 7.07 (s, 1H), 6.57 (s, 1H), 5.63-5.31 (m, 1H), 4.19-3.97 (m, 2H), 3.97-3.66 (m, 2H), 3.55-3.43 (m, 1H), 3.43-3.26 (m, 3H), 2.32 (dq, J=14.4, 7.3 Hz, 1H), 1.23-1.12 (m, 2H), 1.10-0.93 (m, 1H), 0.91-0.63 (m, 3H). LRMS (ESI) calcd for (C$_{16}$H$_{21}$N$_5$O+H$^+$) 300.2, found 300.3.

EXAMPLE 53

2-methoxy-1-(7-(methyl(7H-pyrrolo[2,3-d]pyrimidin-4-yl)amino)-5-azaspiro[2.4]heptan-5-yl)ethan-1-one

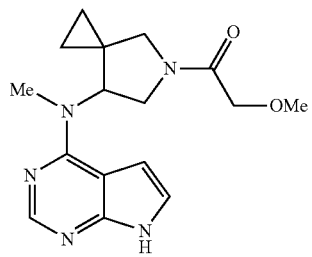 [SMILES: COCC(=O)N1CC(N(C)c2ncnc3[nH]ccc23)C2(CC2)C1]

$^1$H NMR (400 MHz, CDCl$_3$) δ 10.09 (s, 1H), 8.23 (s, 1H), 7.05 (d, J=2.3 Hz, 1H), 6.57 (d, J=3.1 Hz, 1H), 5.38 (d, J=5.7 Hz, 1H), 4.07 (d, J=7.5 Hz, 1H), 3.96 (dd, J=11.0, 7.4 Hz, 1H), 3.73 (d, J=9.9 Hz, 1H), 3.62 (dd, J=11.0, 2.2 Hz, 1H), 3.42 (s, 3H), 1.44-1.30 (m, 2H), 1.21-1.04 (m, 3H), 1.03-0.95 (m, 1H), 0.84-0.68 (m, 3H). LRMS (ESI) calcd for (C$_{16}$H$_{21}$N$_5$O$_2$+H$^+$) 316.2, found 316.1.

EXAMPLE 54

2-azido-1-(7-(methyl(7H-pyrrolo[2,3-d]pyrimidin-4-yl)amino)-5-azaspiro[2.4]heptan-5-yl)ethan-1-one

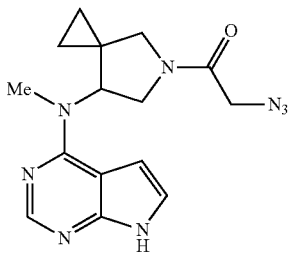 [SMILES: CN(c1ncnc2[nH]ccc12)C1CN(C(=O)CN=[N+]=[N-])CC12CC2]

$^1$H NMR (400 MHz, CDCl$_3$) δ 10.98 (s, 1H), 8.37-8.03 (m, 1H), 7.17-6.97 (m, 1H), 6.69-6.45 (m, 1H), 5.63-5.32 (m, 1H), 4.15-4.00 (m, 1H), 3.99-3.75 (m, 3H), 3.69-3.48 (m, 2H), 3.48-3.27 (m, 3H), 1.04-0.93 (m, 1H), 0.91-0.64 (m, 3H). LRMS (ESI) calcd for (C$_{15}$H$_{18}$N$_8$O+H$^+$) 327.2, found 327.2.

EXAMPLE 55

3-(7-(methyl(7H-pyrrolo[2,3-d]pyrimidin-4-yl)amino)-5-azaspiro[2.4]heptan-5-yl)-3-oxopropanenitrile

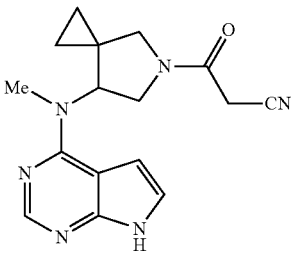 [SMILES: CN(c1ncnc2[nH]ccc12)C1CN(C(=O)CC#N)CC12CC2]

$^1$H NMR (400 MHz, CDCl$_3$) δ 9.55 (s, 1H), 8.27 (d, J=4.8 Hz, 1H), 7.15-7.03 (m, 1H), 6.61 (s, 1H), 5.58-5.35 (m, 1H), 4.26-4.03 (m, 1H), 4.02-3.91 (m, 1H), 3.89-3.72 (m, 1H), 3.72-3.51 (m, 2H), 3.48 (d, J=7.7 Hz, 2H), 3.45-3.32 (m, 2H), 1.19-0.99 (m, 1H), 0.95-0.68 (m, 3H). LRMS (ESI) calcd for (C$_{16}$H$_{18}$N$_6$O+H$^+$) 311.2, found 311.2.

EXAMPLE 56

N-(2-(7-(methyl(7H-pyrrolo[2,3-d]pyrimidin-4-yl)amino)-5-azaspiro[2.4]heptan-5-yl)-2-oxoethyl)acetamide

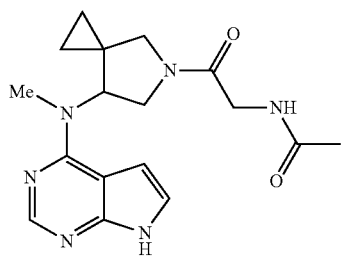 [SMILES: CC(=O)NCC(=O)N1CC(N(C)c2ncnc3[nH]ccc23)C2(CC2)C1]

$^1$H NMR (400 MHz, CDCl$_3$) δ 10.18 (d, J=14.5 Hz, 1H), 8.26 (d, J=5.3 Hz, 1H), 7.08 (dd, J=18.0, 14.6 Hz, 1H), 6.68 (d, J=17.3 Hz, 1H), 6.58 (d, J=3.1 Hz, 1H), 5.55-5.35 (m, 1H), 4.17-4.03 (m, 2H), 4.03-3.93 (m, 1H), 3.87 (dd, J=27.0, 11.3 Hz, 1H), 3.78-3.68 (m, 1H), 3.57-3.48 (m, 1H), 3.46-3.33 (m, 3H), 2.08 (d, J=4.2 Hz, 3H), 1.14-0.97 (m, 1H), 0.94-0.72 (m, 3H). LRMS (ESI) calcd for (C$_{17}$H$_{22}$N$_6$O$_2$+H$^+$) 343.2, found 343.2.

EXAMPLE 57

N-methyl-3-(7-(methyl(7H-pyrrolo[2,3-d]pyrimidin-4-yl)amino)-5-azaspiro[2.4]heptan-5-yl)-3-oxopropanamide

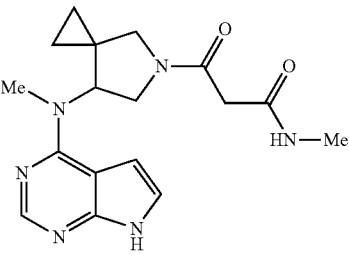

$^1$H NMR (400 MHz, CDCl$_3$) δ 11.89 (s, 1H), 8.24 (d, J=4.2 Hz, 1H), 8.08 (s, 1H), 7.17-7.05 (m, 1H), 6.54 (d, J=2.0 Hz, 1H), 5.43 (t, J=7.8 Hz, 1H), 5.30 (s, 1H), 4.13 (ddd, J=21.2, 12.7, 7.5 Hz, 1H), 3.91 (dd, J=46.8, 11.7 Hz, 1H), 3.99-3.81 (m, 1H), 3.49 (t, J=11.0 Hz, 1H), 3.42 (s, 1H), 3.37 (t, J=10.0 Hz, 3H), 2.84 (dd, J=4.7, 2.5 Hz, 3H), 1.10-0.95 (m, 1H), 0.89-0.72 (m, 3H). LRMS (ESI) calcd for (C$_{17}$H$_{22}$N$_6$O$_2$+H$^+$) 343.2, found 343.1.

EXAMPLE 58

3-amino-1-(7-(methyl(7H-pyrrolo[2,3-d]pyrimidin-4-yl)amino)-5-azaspiro[2.4]heptan-5-yl)propan-1-one

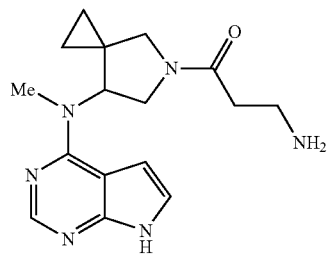 [SMILES: CN(c1ncnc2[nH]ccc12)C1CN(C(=O)CCN)CC12CC2]

¹H NMR (400 MHz, DMSO) δ 11.75 (s, 1H), 8.08 (d, J=3.1 Hz, 1H), 7.92 (s, 2H), 7.17 (d, J=2.4 Hz, 1H), 6.61 (s, 1H), 5.39-5.06 (m, 1H), 4.20-3.57 (m, 3H), 3.32-3.24 (m, 4H), 3.11-2.90 (m, 2H), 2.87-2.56 (m, 2H), 0.96-0.68 (m, 3H), 0.68-0.44 (m, 1H). LRMS (ESI) calcd for (C$_{16}$H$_{22}$N$_6$O+H$^+$) 315.2, found 315.2.

EXAMPLE 59

2-(1H-imidazol-1-yl)-1-(7-(methyl(7H-pyrrolo[2,3-d]pyrimidin-4-yl)amino)-5-azaspiro[2.4]heptan-5-yl)ethan-1-one

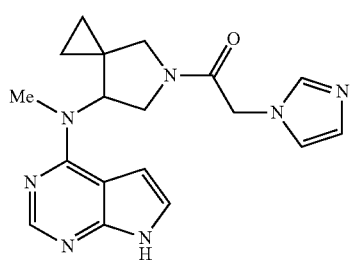 [SMILES: CN(c1ncnc2[nH]ccc12)C1CN(C(=O)Cn2ccnc2)CC12CC2]

¹H NMR (400 MHz, CDCl$_3$) δ 9.51 (s, 1H), 8.26 (d, J=10.0 Hz, 1H), 7.56 (d, J=5.7 Hz, 1H), 7.20-6.96 (m, 3H), 6.60 (d, J=10.0 Hz, 1H), 5.60-5.35 (m, 1H), 4.75 (d, J=6.7 Hz, 2H), 4.02-3.88 (m, 1H), 3.77 (dd, J=27.1, 10.8 Hz, 1H), 3.59-3.49 (m, 1H), 3.49-3.30 (m, 3H), 1.18-1.08 (m, 1H), 1.08-0.96 (m, J=9.5 Hz, 1H), 0.96-0.72 (m, 3H). LRMS (ESI) calcd for (C$_{18}$H$_{21}$N$_7$O+H$^+$) 352.2, found 352.1.

EXAMPLE 60

3-(7-(methyl(7H-pyrrolo[2,3-d]pyrimidin-4-yl)amino)-5-azaspiro[2.4]heptan-5-yl)-3-thioxopropanenitrile

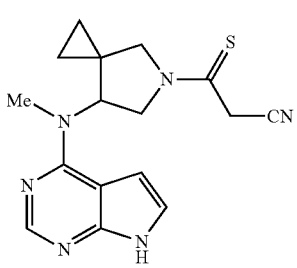

¹H NMR (400 MHz, CDCl$_3$) δ 11.35 (s, 1H), 8.26 (d, J=2.2 Hz, 1H), 7.16-7.07 (m, 1H), 6.58 (dd, J=5.6, 3.7 Hz, 1H), 5.52 (ddd, J=9.0, 7.3, 2.4 Hz, 1H), 4.44-4.20 (m, 2H), 4.11 (dd, J=55.2, 12.4 Hz, 1H), 3.91 (d, J=9.3 Hz, 2H), 3.73 (dd, J=68.2, 12.8 Hz, 1H), 3.42 (d, J=22.7 Hz, 3H), 1.18-1.01 (m, 1H), 0.98-0.75 (m, 3H). LRMS (ESI) calcd for (C$_{16}$H$_{18}$N$_6$S+H$^+$) 327.1, found 327.1.

EXAMPLE 61 isobutyl 7-(methyl(7H-pyrrolo[2,3-d]pyrimidin-4-yl)amino)-5-azaspiro[2.4]heptane-5-carboxylate

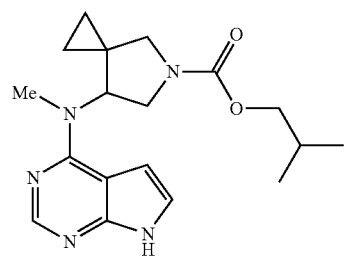 [SMILES: CC(C)COC(=O)N1CC(N(C)c2ncnc3[nH]ccc23)C2(CC2)C1]

¹H NMR (400 MHz, CDCl$_3$) δ 9.24 (s, 1H), 8.24 (s, 1H), 7.05 (s, 1H), 6.59 (s, 1H), 5.40 (s, 1H), 4.04 (dd, J=12.3, 7.5 Hz, 1H), 3.92 (d, J=5.3 Hz, 2H), 3.85-3.62 (m, 2H), 3.51-3.23 (m, 4H), 2.05-1.86 (m, 1H), 1.13-0.86 (m, 7H), 0.77 (d, J=8.0 Hz, 3H). LRMS (ESI) calcd for (C$_{18}$H$_{25}$N$_5$O$_2$+H$^+$) 344.2, found 344.1.

EXAMPLE 62

N-(5-(ethylsulfonyl)-5-azaspiro[2.4]heptan-7-yl)-N-methyl-7H-pyrrolo[2,3-d]pyrimidin-4-amine

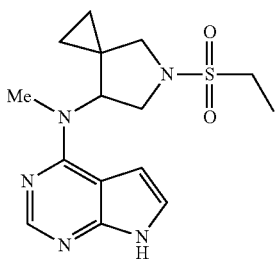 [SMILES: CCS(=O)(=O)N1CC(N(C)c2ncnc3[nH]ccc23)C2(CC2)C1]

$^1$H NMR (400 MHz, CDCl$_3$) δ 10.01 (s, 1H), 8.24 (s, 1H), 7.08 (d, J=2.2 Hz, 1H), 6.61 (d, J=3.0 Hz, 1H), 5.57 (dd, J=7.5, 3.1 Hz, 1H), 3.94 (dd, J=11.0, 7.5 Hz, 1H), 3.74-3.64 (m, 2H), 3.55-3.47 (m, 3H), 3.36 (d, J=9.8 Hz, 1H), 3.16-3.04 (m, 2H), 1.45 (t, J=7.4 Hz, 3H), 1.10-1.03 (m, 1H), 0.86-0.71 (m, 3H). LRMS (ESI) calcd for (C$_{15}$H$_{21}$N$_5$O$_2$S+H$^+$) 336.2, found 336.2.

EXAMPLE 63

N-(5-((2-aminoethyl)sulfonyl)-5-azaspiro[2.4]heptan-7-yl)-N-methyl-7H-pyrrolo[2,3-d]pyrimidin-4-amine

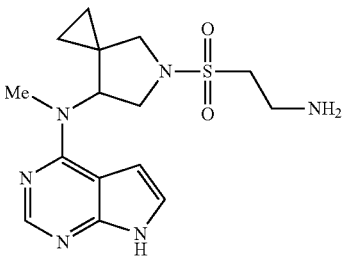 [SMILES: CN(c1ncnc2[nH]ccc12)C1CN(S(=O)(=O)CCN)CC12CC2]

$^1$H NMR (400 MHz, CDCl$_3$) δ 11.81 (s, 1H), 8.24 (s, 1H), 7.10 (d, J=3.6 Hz, 1H), 6.57 (d, J=3.6 Hz, 1H), 5.54 (dd, J=7.4, 2.9 Hz, 1H), 3.92 (dd, J=11.0, 7.6 Hz, 1H), 3.76-3.59 (m, 2H), 3.48 (s, 3H), 3.33 (d, J=9.9 Hz, 1H), 3.30-3.22 (m, 2H), 3.22-3.02 (m, 2H), 1.88 (s, 2H), 1.04 (dd, J=7.3, 4.2 Hz, 1H), 0.91-0.58 (m, 3H). LRMS (ESI) calcd for (C$_{15}$H$_{22}$N$_6$O$_2$S+H$^+$) 351.2, found 351.2.

EXAMPLE 64

(S)-1-(7-(methyl(7H-pyrrolo[2,3-d]pyrimidin-4-yl)amino)-5-azaspiro[2.4]heptan-5-yl)propan-1-one

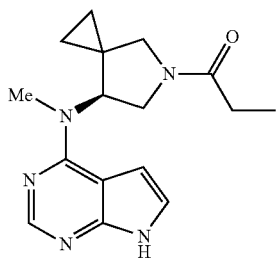 [SMILES: CCC(=O)N1C[C@@H](N(C)c2ncnc3[nH]ccc23)C2(CC2)C1]

$^1$H NMR (400 MHz, CDCl$_3$) δ 9.49 (s, 1H), 8.23 (d, J=5.8 Hz, 1H), 7.04 (s, 1H), 6.58 (s, 1H), 5.48-5.32 (m, 1H), 4.18-3.98 (m, 1H), 3.82 (ddd, J=47.3, 32.5, 11.5 Hz, 2H), 3.51-3.28 (m, 4H), 2.32 (td, J=14.9, 7.6 Hz, 2H), 1.27 (d, J=9.7 Hz, 1H), 1.22-1.11 (m, 2H), 1.11-0.93 (m, 1H), 0.93-0.61 (m, 3H). LRMS (ESI) calcd for (C$_{16}$H$_{21}$N$_5$O+H$^+$) 300.2, found 300.1.

EXAMPLE 65

(S)-2-azido-1-(7-(methyl(7H-pyrrolo[2,3-d]pyrimidin-4-yl)amino)-5-azaspiro[2.4]heptan-5-yl)ethan-1-one

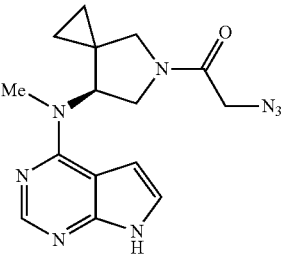 [SMILES: CN(c1ncnc2[nH]ccc12)[C@@H]1CN(C(=O)CN=[N+]=[N-])CC12CC2]

$^1$H NMR (400 MHz, CDCl$_3$) δ 9.58 (s, 1H), 8.23 (d, J=3.6 Hz, 1H), 7.03 (d, J=23.7 Hz, 1H), 6.66-6.45 (m, 1H), 5.43 (dd, J=47.4, 5.3 Hz, 1H), 4.15-4.01 (m, 1H), 3.99-3.74 (m, 3H), 3.58 (dd, J=58.3, 11.9 Hz, 1H), 3.46-3.31 (m, 4H), 1.13-0.94 (m, 1H), 0.92-0.66 (m, 3H). LRMS (ESI) calcd for (C$_{15}$H$_{18}$N$_8$O+H$^+$) 327.2, found 327.2.

EXAMPLE 66

(S)-3-(7-(methyl(7H-pyrrolo[2,3-d]pyrimidin-4-yl)amino)-5-azaspiro[2.4]heptan-5-yl)-3-oxopropanenitrile

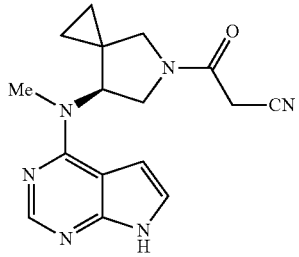 [SMILES: CN(c1ncnc2[nH]ccc12)[C@@H]1CN(C(=O)CC#N)CC12CC2]

¹H NMR (400 MHz, CDCl₃) δ 11.37 (s, 1H), 8.26 (d, J=4.5 Hz, 1H), 7.16-7.02 (m, 1H), 6.57 (dd, J=7.0, 3.5 Hz, 1H), 5.45 (ddd, J=38.6, 7.3, 2.3 Hz, 1H), 4.14 (ddd, J=21.4, 12.5, 7.5 Hz, 1H), 3.91 (t, J=11.5 Hz, 1H), 3.85 (ddd, J=13.7, 12.7, 2.6 Hz, 1H), 3.48 (q, J=13.5 Hz, 1H), 3.45 (s, 3H), 3.39 (s, 2H), 1.14-0.98 (m, 1H), 0.92-0.73 (m, 3H). LRMS (ESI) calcd for (C₁₆H₁₈N₆O+H⁺) 311.2, found 311.2.

EXAMPLE 67

(S)-N-methyl-3-(7-(methyl(7H-pyrrolo[2,3-d]pyrimidin-4-yl)amino)-5-azaspiro[2.4]heptan-5-yl)-3-oxopropanamide

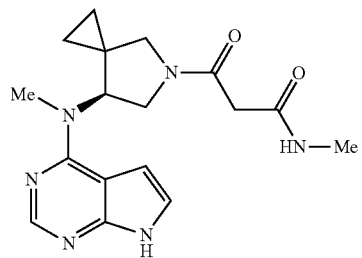 [SMILES: CNC(=O)CC(=O)N1C[C@@H](N(C)c2ncnc3[nH]ccc23)C2(CC2)C1]

¹H NMR (500 MHz, CDCl₃) δ 11.85 (d, J=9.2 Hz, 1H), 8.24 (d, J=8.8 Hz, 1H), 8.10 (d, J=11.0 Hz, 1H), 7.11 (d, J=3.0 Hz, 1H), 6.55 (s, 1H), 5.43 (dd, J=16.7, 6.3 Hz, 1H), 4.13 (ddd, J=21.1, 12.5, 7.5 Hz, 1H), 4.00-3.81 (m, 2H), 3.49 (t, J=11.4 Hz, 1H), 3.40 (d, J=18.6 Hz, 3H), 3.37 (d, J=29.0 Hz, 2H), 2.86 (t, J=11.0 Hz, 3H), 1.09-0.97 (m, 1H), 0.86-0.69 (m, 3H). LRMS (ESI) calcd for (C₁₇H₂₂N₆O₂+H⁺) 343.2, found 343.1.

EXAMPLE 68

(S)-4-(7-(methyl(7H-pyrrolo[2,3-d]pyrimidin-4-yl)amino)-5-azaspiro[2.4]heptane-5-carbonyl)benzonitrile

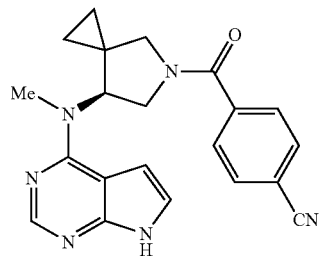 [SMILES: CN(c1ncnc2[nH]ccc12)[C@@H]1CN(C(=O)c2ccc(C#N)cc2)CC12CC2]

¹H NMR (400 MHz, CDCl₃) δ 9.48 (s, 1H), 8.24 (d, J=27.2 Hz, 1H), 7.85-7.55 (m, 4H), 7.07 (d, J=7.4 Hz, 1H), 6.59 (d, J=19.0 Hz, 1H), 5.64-5.34 (m, 1H), 4.37-4.03 (m, 2H), 3.84-3.27 (m, 5H), 1.16-1.00 (m, 1H), 0.98-0.60 (m, 3H). LRMS (ESI) calcd for (C₂₁H₂₀N₆O+H⁺) 373.2, found 373.2.

EXAMPLE 69

(S)-3-(7-(methyl(7H-pyrrolo[2,3-d]pyrimidin-4-yl)amino)-5-azaspiro[2.4]heptan-5-yl)-3-thioxopropanenitrile

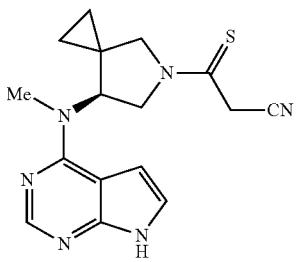 [SMILES: CN(c1ncnc2[nH]ccc12)[C@@H]1CN(C(=S)CC#N)CC12CC2]

¹H NMR (400 MHz, CDCl₃) δ 11.13 (s, 1H), 8.18 (s, 1H), 7.11-6.97 (m, 1H), 6.59-6.44 (m, 1H), 5.56-5.34 (m, 1H), 4.38-3.92 (m, 3H), 3.92-3.78 (m, 2H), 3.66 (dd, J=67.4, 13.0 Hz, 1H), 3.36 (d, J=22.9 Hz, 3H), 1.09-0.94 (m, 1H), 0.91-0.58 (m, 3H). LRMS (ESI) calcd for (C₁₆H₁₈N₆S+H⁺) 327.1, found 327.1.

EXAMPLE 70 isobutyl (S)-7-(methyl(7H-pyrrolo[2,3-d]pyrimidin-4-yl)amino)-5-azaspiro[2.4]heptane-5-carboxylate

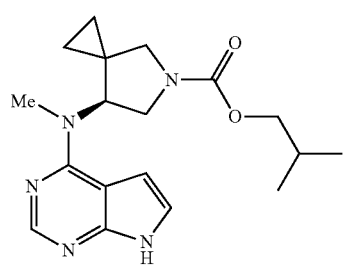 [SMILES: CC(C)COC(=O)N1C[C@@H](N(C)c2ncnc3[nH]ccc23)C2(CC2)C1]

$^1$H NMR (400 MHz, CDCl$_3$) δ 10.26 (s, 1H), 8.25 (s, 1H), 7.07 (d, J=3.2 Hz, 1H), 6.58 (d, J=2.8 Hz, 1H), 5.51-5.50 (m, 1H), 4.11-4.04 (m, 1H), 3.93 (d, J=1.2 Hz, 2H), 3.91-3.74 (m, 2H), 3.42-3.38 (m, 4H), 2.01-1.90 (m, 1H), 1.01-0.95 (m, 7H), 0.77-0.75 (d, J=10.0 Hz, 3H). LRMS (ESI) calcd for (C$_{18}$H$_{25}$N$_5$O$_2$+H$^+$) 344.2, found 344.3.

EXAMPLE 71

(S)-N-(5-(ethylsulfonyl)-5-azaspiro[2.4]heptan-7-yl)-N-methyl-7H-pyrrolo[2,3-d]pyrimidin-4-amine

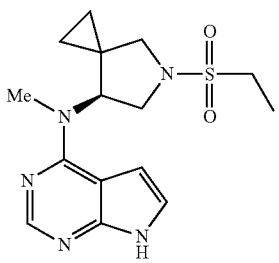 [SMILES: CCS(=O)(=O)N1C[C@@H](N(C)c2ncnc3[nH]ccc23)C2(CC2)C1]

$^1$H NMR (400 MHz, CDCl$_3$) δ 10.45 (s, 1H), 8.23 (s, 1H), 7.07 (d, J=3.1 Hz, 1H), 6.58 (d, J=3.4 Hz, 1H), 5.55 (dd, J=7.5, 3.0 Hz, 1H), 3.92 (dd, J=11.0, 7.6 Hz, 1H), 3.80-3.57 (m, 2H), 3.48 (s, 3H), 3.33 (d, J=9.8 Hz, 1H), 3.08 (q, J=7.4 Hz, 2H), 1.43 (t, J=7.4 Hz, 3H), 1.11-0.90 (m, 1H), 0.90-0.60 (m, 3H). LRMS (ESI) calcd for (C$_{15}$H$_{21}$N$_5$O$_2$S+H$^+$) 336.2, found 336.1.

EXAMPLE 72

(S)-N-methyl-N-(5-(phenylsulfonyl)-5-azaspiro[2.4]heptan-7-yl)-7H-pyrrolo[2,3-d]pyrimidin-4-amine

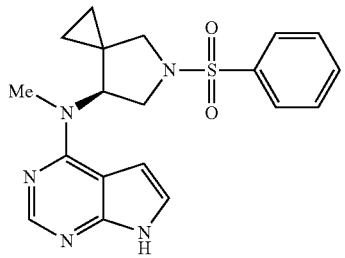 [SMILES: CN(c1ncnc2[nH]ccc12)[C@@H]1CN(S(=O)(=O)c2ccccc2)CC12CC2]

$^1$H NMR (400 MHz, CDCl$_3$) δ 9.97 (s, 1H), 8.16 (s, 1H), 7.85 (d, J=8.0 Hz, 2H), 7.65 (t, J=6.9 Hz, 1H), 7.57 (t, J=7.8 Hz, 2H), 7.04 (s, 1H), 6.53 (s, 1H), 5.46-5.36 (m, 1H), 3.68-3.56 (m, 2H), 3.52 (d, J=9.6 Hz, 1H), 3.34 (s, 3H), 3.07 (d, J=9.5 Hz, 1H), 0.93-0.83 (m, 1H), 0.78-0.68 (m, 1H), 0.65-0.55 (m, 2H). LRMS (ESI) calcd for (C$_{19}$H$_{21}$N$_5$O$_2$S+H$^+$) 384.2, found 384.0.

EXAMPLE 73

(R)-N-(5-ethyl-5-azaspiro[2.4]heptan-7-yl)-N-methyl-7H-pyrrolo[2,3-d]pyrimidin-4-amine

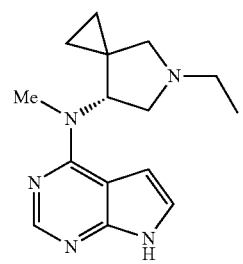 [SMILES: CCN1C[C@H](N(C)c2ncnc3[nH]ccc23)C2(CC2)C1]

$^1$H NMR (400 MHz, CDCl$_3$) δ 10.17 (s, 1H), 8.29 (s, 1H), 7.04 (d, J=3.6 Hz, 1H), 6.60 (d, J=3.6 Hz, 1H), 5.57 (s, 1H), 3.47 (s, 3H), 3.16 (s, 1H), 3.03 (s, 1H), 2.92 (d, J=7.6 Hz, 1H), 2.66 (d, J=9.2 Hz, 3H), 1.23 (t, J=7.2 Hz, 3H), 0.98-0.94 (m, 1H), 0.77-0.68 (m, 2H), 0.55-0.53 (m, 1H). LRMS (ESI) calcd for (C$_{15}$H$_{21}$N$_5$+H$^+$) 272.2, found 272.1.

EXAMPLE 74

Effectiveness of Compound of Formula 1 as JAK Inhibitor

1. In Vitro Kinase Inhibition Test
(1) Dilution of Kinase
Kinases used were human-derived JAK1, JAK2, JAK3, and TYK2 (Millipore, Germany). Each of these kinases was diluted with a suitable buffer solution as described below, and then mixed with reagents.
(1.1) Composition of JAK1 Dilution Buffer Solution
Tris(hydroxymethyl)aminomethane (TRIS) and ethylenediaminetetraacetic acid (EDTA) were dissolved in distilled water at a concentration of 20 mM and 0.2 mM, respectively, and 100 uL of β-mercaptoethanol, 10 uL of Brij-35™, and 5 mL of glycerol, each per 100 mL of the solution, were added to the solution, thereby preparing a JAK1 dilution buffer solution.

(1.2) Composition of JAK2, JAK3, and TYK2 Dilution Buffer Solution 3-morpholinopropane-1-sulfonic acid (MOPS) and EDTA were dissolved in distilled water at a concentration of 20 mM and 1 mM, respectively, and 100 uL of β-mercaptoethanol, 10 uL of Brij-35™, 5 mL of glycerol, and 100 mg of bovine serum albumin (BSA), each per 100 mL of the solution, were added to the solution, thereby preparing a JAK2, JAK3, and TYK2 dilution buffer solution.

(2) Compound Preparation and Experimental Method

Each compound was dissolved in a 100% DMSO solution at a 50 uM concentration. This solution was reacted with reagents in wells on a 96-well plate to reach a final concentration of 1 uM. Detailed experimental methods for each kinase are described below.

(2.1) JAK1

Final concentrations of materials included in 25 uL of the reaction solution are shown in Table 1.

TABLE 1

| Materials | Concentration |
| --- | --- |
| Human JAK1 | 1 unit |
| Tris HCl (pH 7.5) | 20 mM |
| EDTA | 0.2 mM |
| Peptide of SEQ ID NO: 1/ 100 mM HEPES | 1 mM |
| MgAcetate (available from BDH, Cat. # 101484T) | 10 mM |
| γ-$^{33}$P-ATP | 2 mM |
| Test compound | 1 uM |

γ-$^{33}$P-ATP prepared from non-radiolabelled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay. The methanol drying is a drying process using an azeotropic effect, wherein methanol is added into an aqueous solution for drying.

(2.2) JAK2

Final concentrations of materials included in 25 uL of the reaction solution are shown in Table 2.

TABLE 2

| Materials | Concentration |
| --- | --- |
| Human JAK2 | 1 unit |
| MOPS (pH 7.0) | 8 mM |
| EDTA | 0.2 mM |
| Peptide of SEQ ID NO: 2/ 50 mM Tris pH 8.0 | 100 uM |
| MgAcetate (available from BDH, Cat. # 101484T) | 10 mM |
| γ-$^{33}$P-ATP | 2 mM |
| Test compound | 1 uM |

γ-$^{33}$P-ATP prepared from non-radiolabelled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.3) JAK3

Final concentrations of materials included in 25 uL of the reaction solution are shown in Table 3.

TABLE 3

| Materials | Concentration |
| --- | --- |
| Human JAK3 | 1 unit |
| MOPS (pH 7.0) | 8 mM |
| EDTA | 0.2 mM |
| Peptide of SEQ ID NO: 3/ 20 mM MOPS pH 7.0 | 50 uM |
| MgAcetate (available from BDH, Cat. # 101484T) | 10 mM |
| γ-$^{33}$P-ATP | 2 mM |
| Test compound | 1 uM |

γ-$^{33}$P-ATP prepared from non-radiolabelled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.4) TYK2

Final concentrations of materials included in 25 uL of the reaction solution are shown in Table 4.

TABLE 4

| Materials | concentration |
| --- | --- |
| Human TYK2 | 1 unit |
| MOPS (pH 7.0) | 8 mM |
| EDTA | 0.2 mM |
| Peptide of SEQ ID NO: 4/water | 250 uM |
| MgAcetate (available from BDH, Cat. # 101484T) | 10 mM |
| γ-$^{33}$P-ATP | 2 mM |
| Test compound | 1 uM |

γ-$^{33}$P-ATP prepared from non-radiolabelled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.5) IC$_{50}$ Value Measurement

Kinase-activity inhibitory effects of some of the compounds of Examples 1 to 73 (for example, Examples 5, 55, and 66) for JAK1, JAK2, JAK3, and TYK2 were measured at various concentrations by the above-described method, and IC$_{50}$ values were determined. The IC$_{50}$ values of the test compounds were calculated from % inhibition values of the compounds, by the Cheng-Prusoff method (*Biochem. Pharmacol.* (1973) 22, 3099-3108).

(3) Test Results

Tables 5 and 6 show the results of measuring JAK1, JAK2, JAK3, and TYK2 phosphorylation inhibitory levels of the compounds synthesized in Examples 1 to 73, by the above-described method. In Tables 5 and 6, the numbers in the "Example" column, which are identification numbers of the examples, indicate the compounds synthesized in the corresponding examples, the values in the "JAK1", "JAK2", "JAK3", and "TYK2" columns represent kinase-phosphorylation inhibitory levels as a percentage (%) of the compounds synthesized in the corresponding examples at a 1 uM concentration. In Tables 5 and 6, negative values substantially indicate no inhibitory effect.

The inhibitory levels (% inhibition) represent a percentage of reduction in phosphorylation activity in each test group with respect to the phosphorylation activity of a corresponding kinase in a negative control group lacking any of the compounds synthesized in the examples.

% inhibition=[(Scintillation value of Test compound non-treatment group−Scintillation value of Test compound treatment group)/(Scintillation value of Test compound non-treatment group)]×100

As the control group, 1 uM of tofacitinib citrate (available from Hangzhou Tacon Co., Ltd.) was used. The % inhibition values of the control group for JAK1, JAK2, JAK3, and TYK2 were 99%, 98%, 99%, and 100%, respectively.

TABLE 5

| Example | JAK1 | JAK2 | JAK3 | TYK2 |
| --- | --- | --- | --- | --- |
| 1 | 79 | −14 | 8 | −4 |
| 2 | 77 | −19 | 7 | 3 |
| 3 | 83 | 25 | 16 | 49 |
| 4 | 95 | 72 | 57 | 78 |
| 5 | 95 | 79 | 50 | 82 |
| 6 | 90 | 21 | 18 | 46 |
| 7 | 70 | −17 | 8 | 8 |
| 8 | 61 | −7 | 3 | 11 |
| 9 | 90 | 10 | 13 | 70 |
| 10 | 88 | 2 | 23 | 52 |
| 11 | 93 | 10 | 15 | 61 |
| 12 | 80 | −11 | 2 | 26 |
| 13 | 81 | −11 | 13 | 30 |
| 14 | 84 | −14 | 12 | 15 |
| 15 | 76 | −15 | 13 | 43 |
| 16 | 79 | 13 | 15 | 23 |
| 17 | 65 | −14 | −1 | 39 |
| 18 | 71 | −17 | 5 | 37 |
| 19 | 98 | 80 | 82 | 91 |
| 20 | 93 | 27 | 27 | 43 |
| 21 | 94 | −3 | 31 | 30 |
| 22 | 90 | −5 | 16 | 15 |
| 23 | 98 | 52 | 50 | 78 |
| 24 | 94 | 6 | 48 | 47 |
| 25 | 88 | 5 | 25 | 48 |
| 26 | 94 | 13 | 51 | 42 |
| 27 | 91 | −1 | 17 | 27 |
| 28 | 91 | 23 | 40 | 39 |
| 29 | 92 | 19 | 39 | 43 |
| 30 | 80 | −11 | 14 | 27 |
| 31 | 62 | −26 | 13 | 1 |
| 32 | 97 | 68 | 59 | 86 |
| 33 | 98 | 84 | 70 | 88 |
| 34 | 97 | 76 | 56 | 72 |
| 35 | 99 | 78 | 77 | 89 |
| 36 | 97 | 90 | 52 | 91 |
| 37 | 98 | 84 | 61 | 90 |
| 38 | 100 | 97 | 84 | 97 |
| 39 | 99 | 95 | 65 | 93 |
| 40 | 94 | 64 | 47 | 72 |

TABLE 6

| | | | | |
| --- | --- | --- | --- | --- |
| 41 | 99 | 99 | 77 | 97 |
| 42 | 97 | 49 | 33 | 68 |
| 43 | 97 | 70 | 75 | 78 |
| 44 | 100 | 96 | 96 | 98 |
| 45 | 100 | 84 | 60 | 88 |
| 46 | 98 | 81 | 62 | 92 |
| 47 | 99 | 69 | 39 | 71 |
| 48 | 98 | 36 | 28 | 66 |
| 49 | 98 | 65 | 55 | 75 |
| 50 | 98 | 56 | 60 | 81 |
| 51 | 97 | 60 | 49 | 69 |
| 52 | 58 | −22 | 17 | 20 |
| 53 | 76 | −18 | 3 | 7 |
| 54 | 94 | 60 | 73 | 72 |
| 55 | 95 | 53 | 30 | 58 |
| 56 | 9 | −37 | 9 | −10 |
| 57 | 55 | 7 | −9 | 11 |
| 58 | 34 | 2 | −9 | −4 |
| 59 | 72 | −17 | 20 | −8 |
| 60 | 96 | −3 | −14 | 0 |
| 61 | 85 | −9 | 29 | 22 |
| 62 | 95 | 59 | 59 | 67 |
| 63 | 91 | 43 | 7 | 29 |
| 64 | 16 | −9 | −1 | 0 |
| 65 | 41 | 12 | −16 | 14 |
| 66 | 65 | −15 | 17 | −16 |
| 67 | 5 | −7 | 0 | −4 |
| 68 | 14 | −5 | −7 | 2 |
| 69 | 58 | 6 | 9 | 36 |
| 70 | 31 | 24 | −3 | 5 |
| 71 | 40 | 13 | −22 | 12 |
| 72 | 55 | 10 | −1 | 28 |
| 73 | 42 | −6 | 1 | −7 |

Table 7 represents $IC_{50}$ values of the compounds of Examples 5, 55, 66, 41, and 62 for JAK1, JAK2, JAK3, and TYK2 activity.

TABLE 7

| Example | Configuration | JAK1 $IC_{50}$ (nM) | JAK2 $IC_{50}$ (nM) | JAK3 $IC_{50}$ (nM) | TYK2 $IC_{50}$ (nM) |
| --- | --- | --- | --- | --- | --- |
| 5 | R | 8.5 | 412.3 | 1092 | 251.7 |
| 55 | Racemic | 29.3 | 148.5 | 694.5 | 40.4 |
| 66 | S | 787.4 | >1000 | >1000 | >1000 |
| 41 | R | 5.8 | 58.6 | 109.6 | 24.7 |
| 62 | Racemic | 2.8 | 421.8 | >1000 | 198.2 |

Referring to Table 7, the compound of Example 5 having an R-configuration had about 3.5-fold higher JAK1 inhibitory activity, as compared to the compound of Example 55 which is a racemic mixture of the compound of Example 5. Therefore, by isolating a specific stereoisomer having a high JAK inhibitory effect, for example, an enantiomer or a diastereomer, JAK-related diseases may be efficiently treated.

2. Collagen-induced Arthritis (CIA) Model (1) Animal

DBA/1J mice (6 weeks old, male) were purchased from Japan SLC, Inc., and maintained under controlled lighting in a 12-hour light/dark cycle (07:00-19:00). The temperature was maintained at about 22° C., and the mice were allowed to freely have feed and drinking water.

(2) CIA Model Generation Method

Type II collagen (dissolved in 0.05 M acetic acid (2 mg/mL)) was kept at 4° C. prior to induction. On the first day of induction, prior to a first immunization, a complete Freund's adjuvant and type II collagen in an equal ratio were homogenized in a cooled tube using a homogenizer to obtain an emulsion of the type II collagen and the Freund's adjuvant. 0.1 mL of the emulsion was injected into mouse tails for the first immunization. To enhance the immunoreaction, after 21 days of the first immunization, an emulsion was prepared by mixing an incomplete Freund's adjuvant and type II collagen in the same manner as described above, and then injected in the same manner as used for the first immunization. This CIA model generation method was implemented by partial modification of a method described in a published journal (David D Brand et al., Nature Protocols 2, 1269-1275 (2007)).

(3) Experimental Design

Therapeutic efficacy of the compounds according to embodiments was determined using a collagen-induced mouse animal model. The mice were randomly grouped with 8 to 9 mice per group. On the start day and $21^{st}$ day of the experiment, every mouse was subjected to immunization in the same manner as described in Section (2) to induce rheumatoid arthritis. To determine the therapeutic efficacy of test drugs (compounds), a negative control and each drug were orally administered once a day from the $22^{nd}$ day to the $50^{th}$ day of the experiment. As an excipient of the drugs administered, an aqueous solution of 0.45 v/v % carboxymethyl cellulose (CMC) (from Sigma Aldrich, Cat. No. C5678, 0.5 v/v % in distilled water) and 10 v/v % ethanol in distilled water was used. 1 mL of the excipient (per 100 g of weight) only was administered into the negative control group. For the positive control group, 1 mL of a solution of tofacitinib citrate in the excipient (50 mg/10 mL) was administrated per 100 g of weight (50 mg as tofacitinib citrate per 1 kg of weight). Each test compound was prepared at different concentrations (15 mg/10 mL and 50 mg/10 mL), and administered at 1 mL per 100 g of weight (15 mg as per 1 kg of weight, and 50 mg as per 1 kg of weight).

Tofacitinib citrate (available from Hangzhou Tacon Co., Ltd.) as a JAK inhibitor family drug is approved for the treatment of rheumatoid arthritis (RA) in the U.S.A and Russia, and is undergoing clinical testing for use in the treatment of psoriasis, inflammatory bowel disease (IBD) and other immune disorders, and the prevention of organ transplant rejection. Tofacitinib is considered to be effective in the treatment of RA through inhibitory action on JAK3 and JAK1.

(4) Evaluation of Arthritis Model Test

The degree of arthritic disease was determined based on the degree of paw edema obtained by measuring a volume of mouse hind paws of the experimental animals. A volume change in the hind paws was measured using a volume measuring flowmeter (Plethysmometer, Havard apparatus, USA, Cat no. 760220), wherein the volume was measured by putting the mouse hind legs into a measurement cell, from knee to paw. The volumes of both paws were measured, and a larger volume value between the two was used as a representative value. The first volume measurement was performed one day early, before oral administration, and the volumes were measured at an interval of 2-3 days and recorded.

FIG. 1 is a graph of hind paw volume (degree of edema) with respect to time (days) after the first immunization. In FIG. 1, the control group refers to the mouse group into which tofacitinib citrate was administered from the $21^{st}$ day after the first immunization, and the test group refers to the mouse group into which (R)-3-(7-(methyl(7H-pyrrolo[2,3-d]pyrimidin-4-yl)amino)-5-azaspiro[2.4]heptan-5-yl)-3-oxopropanenitrile synthesized in Example 5 was administered (50 mg/kg per body weight) from the $21^{st}$ day after the first immunization. Referring to FIG. 1, around the $34^{th}$ day after the first immunization, the hind paw edema volume of the control group sharply increased. On the other hand, in the test group, from the $31^{st}$ day after the first immunization and when edema had started to increase in the control group, edema caused from arthritis was significantly inhibited from the $31^{st}$ day onwards by about 60% or greater, as compared to the control group, even by about 64% on the $49^{th}$ day when the measurement ended. The results of FIG. 1 indicate that the compound of Example 5 inhibits edema which is known as a typical arthritic symptom, and thus is an effective therapeutic agent for arthritis.

INDUSTRIAL APPLICABILITY

In an aspect of the present disclosure, a compound of Formula 1 according to any of the embodiments, or a pharmaceutically acceptable salt, solvate, or stereoisomer thereof, may be used as a JAK inhibitor.

In another aspect of the present disclosure, a pharmaceutical composition including the compound of Formula 1 according to any of the embodiments, or a pharmaceutically acceptable salt, solvate, or stereoisomer thereof, may be used in treating JAK-related diseases.

In another aspect of the present disclosure, by a method of regulating the activity of a JAK by using the compound of Formula 1 according to the any of the embodiments, or a pharmaceutically acceptable salt, solvate, or stereoisomer thereof, the activity of the JAK may be efficiently regulated.

In another aspect of the present disclosure, by a method of treating a disease in a subject by administering a therapeutically effective amount of the compound of Formula 1 according to any of the embodiments, or a pharmaceutically acceptable salt, solvate, or stereoisomer thereof to a subject, the disease of the individual may be efficiently treated.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

The invention claimed is:

1. A compound of Formula 1, a pharmaceutically acceptable salt thereof, a solvate thereof, or a stereoisomer thereof,

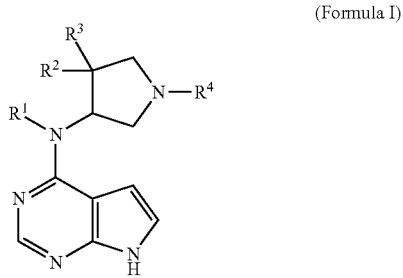

(Formula I)

wherein $R^1$ is $C_{1-6}$ alkyl, $C_{2-6}$ alkenyl, or $C_{2-6}$ alkynyl,
$R^2$ and $R^3$ taken together to form —($C_{2-6}$ alkyl)- or —($C_{2-6}$ alkenyl)-, thereby forms a ring with the carbon atom to which $R^2$ and $R^3$ are attached,
$R^4$ is —$W^1$—$R^6$;
$W^1$ is absent, or is —C(=O)—, —C(=S)—, —C(=O)O—, —C(=O)NR$^5$—, —C(=S)NR$^5$—, —S(=O)—, or —S(=O)$_2$—;

$R^5$ is H or $C_{1-6}$ alkyl;
$R^6$ is H; halo; CN; NO$_2$; N$_3$; $C_{1-10}$ alkyl; $C_{2-10}$ alkenyl; $C_{2-10}$ alkynyl; $C_{1-6}$ haloalkyl; $C_{5-20}$ aryl optionally substituted with at least one substituent selected from the group consisting of $C_{1-10}$ alkyl, $C_{1-6}$ haloalkyl, halo, CN, NO$_2$, and —O—($C_{1-10}$ alkyl); $C_{3-7}$ cycloalkyl; heterocycloalkyl having 3 to 7 ring atoms, optionally substituted with —C(C=O)($C_{1-6}$ alkyl); heteroaryl having 3 to 7 ring atoms; heteroaryl-($C_{1-10}$ alkyl) having 3 to 7 ring atoms; —($C_{1-10}$ alkyl)-CN; —($C_{1-10}$ alkyl)-N$_3$; —($C_{1-10}$ alkyl)-O—($C_{1-6}$ alkyl); —($C_{1-10}$ alkyl)-C(=O)NR$^a$R$^b$; or —($C_{1-10}$ alkyl)-NR$^a$C(=O) R$^b$ or —($C_{1-10}$ alkyl)-NR$^c$R$^d$, wherein R$^a$, R$^b$, R$^c$, and R$^d$ are each independently H or $C_{1-6}$ alkyl.

2. The compound of claim 1, wherein $R^1$ is $C_{1-6}$ alkyl, and $R^2$ and $R^3$ taken together form —($C_{2-6}$ alkyl)-.

3. The compound of claim 1, wherein $W^1$ is absent, or is —C(=O)—, —C(=S)—, —C(=O)O—, —C(=O) NR$^5$—, —C(=S)NR$^5$—, or —S(=O)$_2$—;
$R^5$ is H or $C_{1-6}$ alkyl; and
$R^6$ is $C_{1-10}$ alkyl; $C_{1-6}$ haloalkyl; $C_{5-20}$ aryl optionally substituted with at least one substituent selected from the group consisting of $C_{1-10}$ alkyl, $C_{1-6}$ haloalkyl, halo, CN, NO$_2$, and —O—($C_{1-10}$ alkyl); $C_{3-7}$ cycloalkyl; heterocycloalkyl having 3 to 7 ring atoms, optionally substituted with —C(=O)(C$_{1-6}$ alkyl); heteroaryl having 3 to 7 ring atoms; -heteroaryl-(C$_{1-10}$ alkyl) having 3 to 7 ring atoms; —(C$_{1-10}$ alkyl)-CN; —(C$_{1-10}$ alkyl)-N$_3$; —(C$_{1-10}$ alkyl)-O—(C$_{1-6}$ alkyl); —(C$_{1-10}$ alkyl)-C(=O)NR$^a$R$^b$; or —(C$_{1-10}$ alkyl)-NR$^a$C(=O) R$^b$ or —(C$_{1-10}$ alkyl)-NR$^c$R$^d$, wherein R$^a$, R$^b$, R$^c$, and R$^d$ are each independently H or C$_{1-6}$ alkyl.

4. The compound of claim 1, wherein the compound is a compound represented by Formula 2,

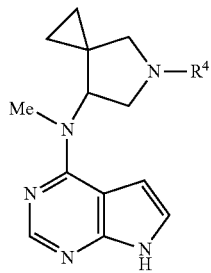

(Formula 2)

wherein
R$^4$ is —W$^1$—R$^6$,
W$^1$ is absent, or is —C(=O)—, —C(=S)—, —C(=O) O—, —C(=O)NR$^5$—, —C(=S)NR$^5$—, or —S(=O)$_2$—,
R$^5$ is H or C$_{1-6}$ alkyl,
R$^6$ is C$_{1-10}$ alkyl, when W$^1$ is absent;
C$_{1-10}$ alkyl; C$_{3-7}$ cycloalkyl; —(C$_{1-10}$ alkyl)-CN; —(C$_{1-10}$ alkyl)-N$_3$; —(C$_{1-10}$ alkyl)-NR$^a$C(=O)R$^b$, wherein R$^a$ and R$^b$ are each independently H or C$_{1-6}$ alkyl; —(C$_{1-10}$ alkyl)-C(=O)NR$^e$R$^f$, wherein R$^e$ and R$^f$ are each independently H or C$_{1-6}$ alkyl; phenyl; phenyl substituted with at least one substituent selected from the group consisting of —CF$_3$ and CN; piperidinyl substituted with —C(C=O)(C$_{1-6}$ alkyl); furanyl; pyridinyl; imidazolyl-(C$_{1-10}$ alkyl); —(C$_{1-10}$ alkyl)-O—(C$_{1-6}$ alkyl); or —(C$_{1-10}$ alkyl)-NR$^c$R$^d$, wherein R$^c$ and R$^d$ are each independently H or C$_{1-6}$ alkyl, when W$^1$ is —C(=O)—;
—(C$_{1-10}$ alkyl)-CN, when W$^1$ is —C(=S)—;
—(C$_{1-10}$ alkyl), when W$^1$ is —C(=O)O—;
—(C$_{1-10}$ alkyl); C$_{3-7}$ cycloalkyl; phenyl; phenyl substituted with at least one substituent selected from the group consisting of halo and C$_{1-10}$ alkyl; biphenyl; or biphenyl substituted with at least one substituent selected from the group consisting of halo and C$_{1-10}$ alkyl, when W$^1$ is —C(=O)NR$^5$;
phenyl substituted with at least one —CF$_3$, when W$^1$ is —C(=S)NR$^5$; or
—C$_{1-10}$ alkyl; —CF$_3$; piperidinyl; morpholinyl; —(C$_{1-10}$ alkyl)-NR$^c$R$^d$, wherein R$^c$ and R$^d$ are each independently H or C$_{1-6}$ alkyl; phenyl; phenyl substituted with at least one substituent selected from the group consisting of —(C$_{1-10}$ alkyl), —O—(C$_{1-6}$ alkyl), —CF$_3$, NO$_2$, CN, and halo; naphthalenyl; or naphthalenyl substituted with at least one substituent selected from the group consisting of —(C$_{1-10}$ alkyl), —O—(C$_{1-6}$ alkyl), —(C$_{1-6}$ haloalkyl), NO$_2$, CN, and halo, when W$^1$ is —S(=O)$_2$—.

5. The compound of claim 1, wherein the compound is (R)-N-(5-butyl-5-azaspiro[2.4]heptan-7-yl)-N-methyl-7H-pyrrolo[2,3-d]pyrimidin-4-amine;

(R)-N-methyl-N-(5-pentyl-5-azaspiro[2.4]heptan-7-yl)-7H-pyrrolo[2,3-d]pyrimidin-4-amine;
(R)-2-methyl-1-(7-(methyl(7H-pyrrolo[2,3-d]pyrimidin-4-yl)amino)-5-azaspiro[2.4]heptan-5-yl)propan-1-one;
(R)-2-azido-1-(7-(methyl(7H-pyrrolo[2,3-d]pyrimidin-4-yl)amino)-5-azaspiro[2.4]heptan-5-yl)ethan-1-one;
(R)-3-(7-(methyl(7H-pyrrolo[2,3-d]pyrimidin-4-yl) amino)-5-azaspiro[2.4]heptan-5-yl)-3-oxopropanenitrile;
(R)-3-methyl-1-(7-(methyl(7H-pyrrolo[2,3-d]pyrimidin-4-yl)amino)-5-azaspiro[2.4]heptan-5-yl)butan-1-one;
(R)-N-(2-(7-(methyl(7H-pyrrolo[2,3-d]pyrimidin-4-yl) amino)-5-azaspiro[2.4]heptan-5-yl)-2-oxoethyl)acetamide;
(R)-N-methyl-3-(7-(methyl(7H-pyrrolo[2,3-d]pyrimidin-4-yl)amino)-5-azaspiro[2.4]heptan-5-yl)-3-oxopropanamide;
(R)-cyclopropyl(7-(methyl(7H-pyrrolo[2,3-d]pyrimidin-4-yl)amino)-5-azaspiro[2.4]heptan-5-yl)methanone;
(R)-1-(4-(7-(methyl(7H-pyrrolo[2,3-d]pyrimidin-4-yl) amino)-5-azaspiro[2.4]heptane-5-carbonyl)piperidin-1-yl)ethan-1-one;
(R)-furan-2-yl(7-(methyl(7H-pyrrolo[-2,3-d]pyrimidin-4-yl)amino)-5-azaspiro[2.4]heptan-5-yl)methanone;
(R)-(7-(methyl(7H-pyrrolo[2,3-d]pyrimidin-4-yl)amino)-5-azaspiro[2.4]heptan-5-yl)(pyridin-3-yl)methanone;
(R)-(7-(methyl(7H-pyrrolo[2,3-d]pyrimidin-4-yl)amino)-5-azaspiro[2.4]heptan-5-yl)(phenyl)methanone;
(R)-(7-(methyl(7H-pyrrolo[2,3-d]pyrimidin-4-yl)amino)-5-azaspiro[2.4]heptan-5-yl)(pyridin-4-yl)methanone;
(R)-3-(7-(methyl(7H-pyrrolo[2,3-d]pyrimidin-4-yl) amino)-5-azaspiro[2.4]heptane-5-carbonyl)benzonitrile;
(R)-4-(7-(methyl(7H-pyrrolo[2,3-d]pyrimidin-4-yl) amino)-5-azaspiro[2.4]heptane-5-carbonyl)benzonitrile;
(R)-(7-(methyl(7H-pyrrolo[2,3-d]pyrimidin-4-yl)amino)-5-azaspiro[2.4]heptan-5-yl)(2-(trifluoromethyl)phenyl)methanone;
(R)-(7-(methyl(7H-pyrrolo[2,3-d]pyrimidin-4-yl)amino)-5-azaspiro[2.4]heptan-5-yl)(3-(trifluoromethyl)phenyl)methanone;
(R)-3-(7-(methyl(7H-pyrrolo[2,3-d]pyrimidin-4-yl) amino)-5-azaspiro[2.4]heptan-5-yl)-3-thioxopropanenitrile;
isobutyl (R)-7-(methyl(7H-pyrrolo[2,3-d]pyrimidin-4-yl) amino)-5-azaspiro[2.4]heptane-5-carboxylate;
(R)-N-butyl-7-(methyl(7H-pyrrolo[2,3-d]pyrimidin-4-yl) amino)-5-azaspiro[2.4]heptane-5-carboxamide;
(R)-N-cyclohexyl-7-(methyl(7H-pyrrolo[2,3-d]pyrimidin-4-yl)amino)-5-azaspiro[2.4]heptane-5-carboxamide;
(R)-7-(methyl(7H-pyrrolo[2,3-d]pyrimidin-4-yl)amino)-N-phenyl-5-azaspiro[2.4]heptane-5-carboxamide;
(R)-N-(4-fluorophenyl)-7-(methyl(7H-pyrrolo[2,3-d]pyrimidin-4-yl)amino)-5-azaspiro[2.4]heptane-5-carboxamide;
(R)-N-(2,4-dichlorophenyl)-7-(methyl(7H-pyrrolo[2,3-d] pyrimidin-4-yl)amino)-5-azaspiro[2.4]heptane-5-carboxamide;
(R)-N-(3,4-dichlorophenyl)-7-(methyl(7H-pyrrolo[2,3-d] pyrimidin-4-yl)amino)-5-azaspiro[2.4]heptane-5-carboxamide;
(R)-N-(2,5-dichlorophenyl)-7-(methyl(7H-pyrrolo[2,3-d] pyrimidin-4-yl)amino)-5-azaspiro[2.4]heptane-5-carboxamide;

(R)-N-(2,3-dichlorophenyl)-7-(methyl(7H-pyrrolo[2,3-d]pyrimidin-4-yl)amino)-5-azaspiro[2.4]heptane-5-carboxamide;
(R)-N-(3-chloro-4-methylphenyl)-7-(methyl(7H-pyrrolo[2,3-d]pyrimidin-4-yl)amino)-5-azaspiro[2.4]heptane-5-carboxamide;
(R)-N-([1,1'-biphenyl]-2-yl)-7-(methyl(7H-pyrrolo[2,3-d]pyrimidin-4-yl)amino)-5-azaspiro[2.4]heptane-5-carboxamide;
(R)-N-(3,5-bis(trifluoromethyl)phenyl)-7-(methyl(7H-pyrrolo[2,3-d]pyrimidin-4-yl)amino)-5-azaspiro[2.4]heptane-5-carbothioamide;
(R)-N-methyl-N-(5-((trifluoromethyl)sulfonyl)-5-azaspiro[2.4]heptan-7-yl)-7H-pyrrolo[2,3-d]pyrimidin-4-amine;
(R)-N-(5-(ethylsulfonyl)-5-azaspiro[2.4]heptan-7-yl)-N-methyl-7H-pyrrolo[2,3-d]pyrimidin-4-amine;
(R)-N-(5-(isopropylsulfonyl)-5-azaspiro[2.4]heptan-7-yl)-N-methyl-7H-pyrrolo[2,3-d]pyrimidin-4-amine;
(R)-N-methyl-N-(5-(propylsulfonyl)-5-azaspiro[2.4]heptan-7-yl)-7H-pyrrolo[2,3-d]pyrimidin-4-amine;
(R)-N-methyl-N-(5-(phenylsulfonyl)-5-azaspiro[2.4]heptan-7-yl)-7H-pyrrolo[2,3-d]pyrimidin-4-amine;
(R)-N-(5-((2-fluorophenyl)sulfonyl)-5-azaspiro[2.4]heptan-7-yl)-N-methyl-7H-pyrrolo[2,3-d]pyrimidin-4-amine;
(R)-N-(5-((3-fluorophenyl)sulfonyl)-5-azaspiro[2.4]heptan-7-yl)-N-methyl-7H-pyrrolo[2,3-d]pyrimidin-4-amine;
(R)-N-(5-((4-fluorophenyl)sulfonyl)-5-azaspiro[2.4]heptan-7-yl)-N-methyl-7H-pyrrolo[2,3-d]pyrimidin-4-amine;
(R)-2-((7-(methyl(7H-pyrrolo[2,3-d]pyrimidin-4-yl)amino)-5-azaspiro[2.4]heptan-5-yl)sulfonyl)benzonitrile;
(R)-3-((7-(methyl(7H-pyrrolo[2,3-d]pyrimidin-4-yl)amino)-5-azaspiro[2.4]heptan-5-yl)sulfonyl)benzonitrile;
(R)-4-((7-(methyl(7H-pyrrolo[2,3-d]pyrimidin-4-yl)amino)-5-azaspiro[2.4]heptan-5-yl)sulfonyl)benzonitrile;
(R)-N-methyl-N-(5-((2-nitrophenyl)sulfonyl)-5-azaspiro[2.4]heptan-7-yl)-7H-pyrrolo[2,3-d]pyrimidin-4-amine;
(R)-N-methyl-N-(5-((3-nitrophenyl)sulfonyl)-5-azaspiro[2.4]heptan-7-yl)-7H-pyrrolo[2,3-d]pyrimidin-4-amine;
(R)-N-methyl-N-(5-((4-nitrophenyl)sulfonyl)-5-azaspiro[2.4]heptan-7-yl)-7H-pyrrolo[2,3-d]pyrimidin-4-amine;
(R)-N-methyl-N-(5-(m-tolylsulfonyl)-5-azaspiro[2.4]heptan-7-yl)-7H-pyrrolo[2,3-d]pyrimidin-4-amine;
(R)-N-(5-((4-methoxyphenyl)sulfonyl)-5-azaspiro[2.4]heptan-7-yl)-N-methyl-7H-pyrrolo[2,3-d]pyrimidin-4-amine;
(R)-N-methyl-N-(5-((4-(trifluoromethyl)phenyl)sulfonyl)-5-azaspiro[2.4]heptan-7-yl)-7H-pyrrolo[2,3-d]pyrimidin-4-amine;
(R)-N-methyl-N-(5-(naphthalen-2-ylsulfonyl)-5-azaspiro[2.4]heptan-7-yl)-7H-pyrrolo[2,3-d]pyrimidin-4-amine;
(R)-N-methyl-N-(5-(piperidin-1-ylsulfonyl)-5-azaspiro[2.4]heptan-7-yl)-7H-pyrrolo[2,3-d]pyrimidin-4-amine;
(R)-N-methyl-N-(5-(morpholinosulfonyl)-5-azaspiro[2.4]heptan-7-yl)-7H-pyrrolo[2,3-d]pyrimidin-4-amine;
1-(7-(methyl(7H-pyrrolo[2,3-d]pyrimidin-4-yl)amino)-5-azaspiro[2.4]heptan-5-yl)propan-1-one;
2-methoxy-1-(7-(methyl(7H-pyrrolo[2,3-d]pyrimidin-4-yl)amino)-5-azaspiro[2.4]heptan-5-yl)ethan-1-one;
2-azido-1-(7-(methyl(7H-pyrrolo[2,3-d]pyrimidin-4-yl)amino)-5-azaspiro[2.4]heptan-5-yl)ethan-1-one;
3-(7-(methyl(7H-pyrrolo[2,3-d]pyrimidin-4-yl)amino)-5-azaspiro[2.4]heptan-5-yl)-3-oxopropanenitrile;
N-(2-(7-(methyl(7H-pyrrolo[2,3-d]pyrimidin-4-yl)amino)-5-azaspiro[2.4]heptan-5-yl)-2-oxoethyl)acetamide;
N-methyl-3-(7-(methyl(7H-pyrrolo[2,3-d]pyrimidin-4-yl)amino)-5-azaspiro[2.4]heptan-5-yl)-3-oxopropanamide;
3-amino-1-(7-(methyl(7H-pyrrolo[2,3-d]pyrimidin-4-yl)amino)-5-azaspiro[2.4]heptan-5-yl)propan-1-one;
2-(1H-imidazol-1-yl)-1-(7-(methyl(7H-pyrrolo[2,3-d]pyrimidin-4-yl)amino)-5-azaspiro[2.4]heptan-5-yl)ethan-1-one;
3-(7-(methyl(7H-pyrrolo[2,3-d]pyrimidin-4-yl)amino)-5-azaspiro[2.4]heptan-5-yl)-3-thioxopropanenitrile;
isobutyl 7-(methyl(7H-pyrrolo[2,3-d]pyrimidin-4-yl)amino)-5-azaspiro[2.4]heptane-5-carboxylate;
N-(5-(ethylsulfonyl)-5-azaspiro[2.4]heptan-7-yl)-N-methyl-7H-pyrrolo[2,3-d]pyrimidin-4-amine;
N-(5-((2-aminoethyl)sulfonyl)-5-azaspiro[2.4]heptan-7-yl)-N-methyl-7H-pyrrolo[2,3-d]pyrimidin-4-amine;
(S)-1-(7-(methyl(7H-pyrrolo[2,3-d]pyrimidin-4-yl)amino)-5-azaspiro[2.4]heptan-5-yl)propan-1-one;
(S)-2-azido-1-(7-(methyl(7H-pyrrolo[2,3-d]pyrimidin-4-yl)amino)-5-azaspiro[2.4]heptan-5-yl)ethan-1-one;
(S)-3-(7-(methyl(7H-pyrrolo[2,3-d]pyrimidin-4-yl)amino)-5-azaspiro[2.4]heptan-5-yl)-3-oxopropanenitrile;
(S)-N-methyl-3-(7-(methyl(7H-pyrrolo[2,3-d]pyrimidin-4-yl)amino)-5-azaspiro[2.4]heptan-5-yl)-3-oxopropanamide;
(S)-4-(7-(methyl(7H-pyrrolo[2,3-d]pyrimidin-4-yl)amino)-5-azaspiro[2.4]heptane-5-carbonyl)benzonitrile;
(S)-3-(7-(methyl(7H-pyrrolo[2,3-d]pyrimidin-4-yl)amino)-5-azaspiro[2.4]heptan-5-yl)-3-thioxopropanenitrile;
Isobutyl (S)-7-(methyl(7H-pyrrolo[2,3-d]pyrimidin-4-yl)amino)-5-azaspiro[2.4]heptane-5-carboxylate;
(S)-N-(5-(ethylsulfonyl)-5-azaspiro[2.4]heptan-7-yl)-N-methyl-7H-pyrrolo[2,3-d]pyrimidin-4-amine;
(S)-N-methyl-N-(5-(phenylsulfonyl)-5-azaspiro[2.4]heptan-7-yl)-7H-pyrrolo[2,3-d]pyrimidin-4-amine;
(R)-N-(5-ethyl-5-azaspiro[2.4]heptan-7-yl)-N-methyl-7H-pyrrolo[2,3-d]pyrimidin-4-amine; or
a pharmaceutically acceptable salt, solvate, or stereoisomer thereof.

6. A pharmaceutical composition comprising the compound of claim 1, a pharmaceutically acceptable salt thereof, a solvate thereof, or a stereoisomer thereof, and a pharmaceutically acceptable carrier.

7. A method of inhibiting the activity of a Janus kinase (JAK), the method comprising contacting the compound of claim 1, or a pharmaceutically acceptable salt, solvate or stereoisomer thereof, with the JAK to inhibit the activity of the JAK.

8. A method of:
(i) alleviating or suppressing a disease in a subject, the method comprising administering a therapeutically effective amount of the compound of claim 1 or a pharmaceutically acceptable salt, solvate, or stereoisomer thereof to a subject, wherein the disease is rheumatoid arthritis, osteoarthritis, allograft rejection, graft-versus-host disease, prostate cancer, lymphoma, leukemia, multiple myeloma, multiple sclerosis, type I diabetes, lupus, psoriasis, inflammatory bowel disease, Crohn's disease, or autoimmune thyroid disease; or (ii) preventing a disease in a subject, the method comprising administering a therapeutically effective amount of the compound of claim 1 or a pharmaceutically acceptable salt, solvate, or stereoisomer thereof to a subject, wherein the disease is allograft rejection or graft-versus-host disease.

9. A method of preparing a compound of Formula 2, the method comprising generating the compound of Formula 2 by reacting a compound of Formula 9 or a salt thereof with a compound of a formula $R^4$-$L^2$:

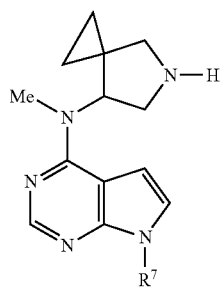

(Formula 9)

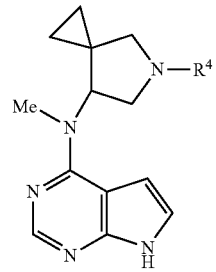

(Formula 2)

wherein $R^7$ in Formula 9 is H or an amino-protecting group, and Formula 2 is the same as defined in claim 4, and $R^4$ in Formula $R^4$-$L^2$ is the same as defined in claim 4 and $L^2$ is a leaving group.

10. The method of claim 8, wherein the leukemia is acute myelogenous leukemia (AML), or acute lymphoblastic leukemia (ALL).

* * * * *

SEQUENCE LISTING

<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: JAK1 substrate

<400> SEQUENCE: 1

```
<210> SEQ ID NO 2
<211> LENGTH: 39
<212> TYPE: PRT
<213> ORGANISM: Artificial Sequence
<220> FEATURE:
<223> OTHER INFORMATION: JAK2 substrate

<400> SEQUENCE: 2

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp Cys
        35

<210> SEQ ID NO 3
<211> LENGTH: 15
<212> TYPE: PRT
<213> ORGANISM: Artificial Sequence
<220> FEATURE:
<223> OTHER INFORMATION: JAK3 substrate

<400> SEQUENCE: 3

Gly Gly Glu Glu Glu Glu Tyr Phe Glu Leu Val Lys Lys Lys Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: TYK substrate

<400> SEQUENCE: 4

Gly Gly Met Glu Asp Ile Tyr Phe Glu Phe Met Gly Gly Lys Lys Lys
1               5                   10                  15
```